US012758285B2

(12) United States Patent
Slater

(10) Patent No.: US 12,758,285 B2
(45) Date of Patent: Oct. 13, 2026

(54) FRACTURE PLATING SYSTEMS AND METHODS

(71) Applicant: Costa Surgical Inc., Chandler, AZ (US)

(72) Inventor: Nicholas Slater, Chandler, AZ (US)

(73) Assignee: Costa Surgical Inc., Chandler, AZ (US)

( * ) Notice: Subject to any disclaimer, the term of this patent is extended or adjusted under 35 U.S.C. 154(b) by 0 days.

(21) Appl. No.: 19/067,944

(22) Filed: Mar. 2, 2025

(65) Prior Publication Data

US 2025/0275796 A1 Sep. 4, 2025

Related U.S. Application Data

(60) Provisional application No. 63/748,317, filed on Jan. 22, 2025, provisional application No. 63/693,769, (Continued)

(51) Int. Cl.

*A61B 17/80* (2006.01)
*A61B 17/17* (2006.01)
(Continued)

(52) U.S. Cl.

CPC ...... *A61B 17/8076* (2013.01); *A61B 17/1728* (2013.01); *A61B 17/683* (2013.01); (Continued)

(58) Field of Classification Search

CPC ............................ A61B 17/80; A61B 17/8076
See application file for complete search history.

(56) References Cited

U.S. PATENT DOCUMENTS 5,722,976 A 3/1998 Brown
7,468,064 B2 12/2008 Bruneau
(Continued)

FOREIGN PATENT DOCUMENTS

CN 219814451 U 10/2023
WO 2024129310 A1 6/2024

OTHER PUBLICATIONS

International Search Report and Written Opinion dated Jul. 8, 2025 for corresponding PCT Application No. PCT/US2025/018054.
(Continued)

*Primary Examiner* — Larry E Waggle, Jr.
(74) *Attorney, Agent, or Firm* — David Meibos; Maywood IP Law

(57) ABSTRACT

A fracture plating system may be configured to stabilize a first fracture of a bone of a patient, the bone may include an interior surface facing toward an interior body cavity of the patient, and an exterior surface facing away from the interior body cavity. The fracture plating system may include a plate having one or more slots and configured to span the first fracture, a first fastener configured to be received in one of the one or more slots and secure the plate to the interior surface, a second fastener configured to be received in one of the one or more slots and secure the plate to the interior surface, and a first tether configured to apply a force directly to the first and second fasteners to guide the plate, the first and second fasteners through the interior body cavity to the interior surface of the bone.

26 Claims, 46 Drawing Sheets

Related U.S. Application Data filed on Sep. 12, 2024, provisional application No. 63/572,491, filed on Apr. 1, 2024, provisional application No. 63/560,219, filed on Mar. 1, 2024.

(51) Int. Cl.

| | |
|---|---|
| ***A61B 17/68*** | (2006.01) |
| ***A61B 17/86*** | (2006.01) |
| ***A61B 17/90*** | (2006.01) |

(52) U.S. Cl.

CPC ...... *A61B 17/8047* (2013.01); *A61B 17/8665* (2013.01); *A61B 17/90* (2021.08); *A61B 2017/867* (2013.01)

(56) References Cited

U.S. PATENT DOCUMENTS

| | | | | |
|---|---|---|---|---|
| 7,608,096 | B2 * | 10/2009 | Foley | A61B 17/7007 606/280 |
| 7,785,355 | B2 | 8/2010 | Mohr | |
| 7,857,839 | B2 * | 12/2010 | Duong | A61B 17/8047 606/280 |
| 8,262,706 | B2 | 9/2012 | Olms | |
| 8,313,517 | B2 | 11/2012 | Mohr | |
| 8,728,133 | B2 * | 5/2014 | Fell | A61B 17/3472 606/328 |
| 8,734,492 | B2 | 5/2014 | Mohr | |
| 8,740,903 | B2 | 6/2014 | Bottlang | |
| 9,265,543 | B2 | 2/2016 | Gephart | |
| 9,603,642 | B2 | 3/2017 | Fell et al. | |
| 9,801,661 | B2 | 10/2017 | Olms | |
| 9,808,297 | B2 * | 11/2017 | Bernstein | A61B 17/808 |
| 10,231,767 | B2 * | 3/2019 | Campbell | A61B 17/809 |
| 10,537,372 | B2 | 1/2020 | Fell | |
| 10,918,428 | B2 | 2/2021 | Garcia | |
| 11,076,900 | B2 | 8/2021 | Campbell | |
| 11,439,446 | B2 | 9/2022 | Garcia | |
| 11,559,340 | B2 | 1/2023 | Fell | |
| 11,737,799 | B2 | 8/2023 | Campbell | |
| 12,089,882 | B2 | 9/2024 | Gregory, II | |
| 2005/0192578 | A1 | 9/2005 | Horst | |
| 2009/0171399 | A1 | 7/2009 | White | |
| 2014/0277175 | A1 | 9/2014 | Campbell | |
| 2018/0049782 | A1 | 2/2018 | Gahman et al. | |
| 2020/0188001 | A1 * | 6/2020 | Davison | A61B 17/8875 |
| 2022/0233221 | A1 * | 7/2022 | Kay | A61B 17/864 |
| 2023/0285060 | A1 | 9/2023 | DeMedici | |
| 2023/0338071 | A1 | 10/2023 | Garcia | |
| 2024/0206928 | A1 * | 6/2024 | Hansen | A61B 17/8023 |

OTHER PUBLICATIONS

Musculoskeletal Key "Current Concepts in Fractures of the Distal Humerus" Aug. 2016, 5 pages.

* cited by examiner

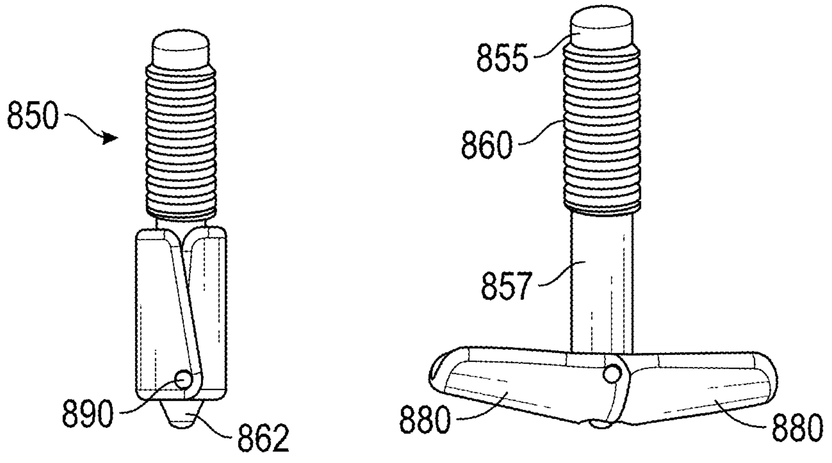
FIG. 64A
FIG. 64B
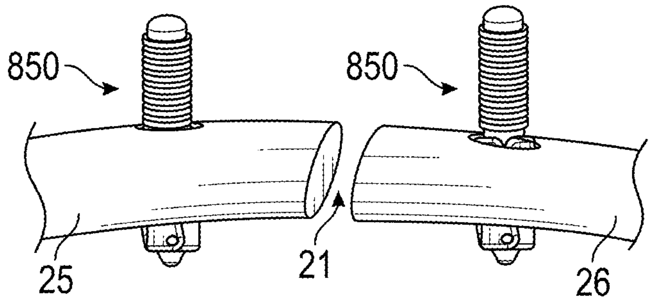
FIG. 65
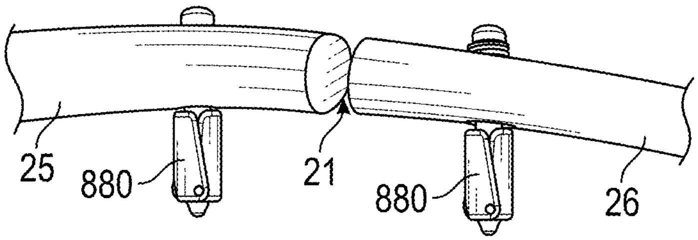
FIG. 66
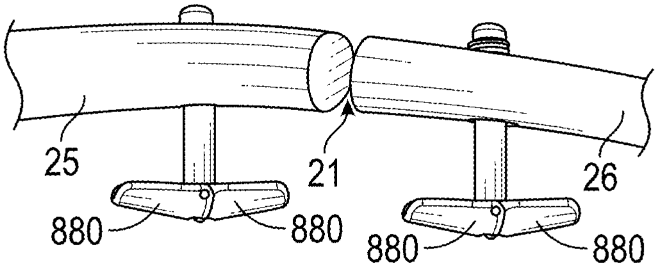
FIG. 67

FRACTURE PLATING SYSTEMS AND METHODS

CROSS-REFERENCE TO RELATED APPLICATIONS

The present application claims the benefit of U.S. Provisional Application No. 63/560,219 filed on Mar. 1, 2024, entitled "FRACTURE PLATING SYSTEMS AND METHODS"; U.S. Provisional Application No. 63/572,491 filed on Apr. 1, 2024, entitled "FRACTURE PLATING SYSTEMS AND METHODS"; U.S. Provisional Application No. 63/693,769 filed on Sep. 12, 2024, entitled "INTERNAL RIB PLATING SYSTEMS AND METHODS"; and U.S. Provisional Application No. 63/748,317 filed on Jan. 22, 2025, entitled "RIB FIXATION SYSTEMS AND METHODS". The foregoing documents are hereby incorporated by reference in their entirety.

TECHNICAL FIELD

The present disclosure relates generally to surgical systems and methods, and more particularly, to systems and methods for fracture plating and stabilization.

BACKGROUND

Bone fractures, particularly in anatomical regions such as the ribs, can present significant challenges in treatment due to their anatomical complexity, constant motion during respiration, and the difficulty of achieving stable fixation. Rib fractures, flail chest, and other thoracic injuries often result from trauma and can lead to severe pain, respiratory complications, and impaired pulmonary function. Proper stabilization of fractured rib segments is crucial to facilitate healing, reduce pain, and restore respiratory mechanics.

Conventional methods of treating rib fractures often involve conservative management, including pain control and respiratory therapy. However, in cases of severe fractures, such as flail chest or displaced rib fractures, surgical intervention may be necessary. Traditional open surgical approaches for rib fixation typically require large incisions, displacement of muscle tissue, and exposure of the fracture site, which can result in increased morbidity, prolonged recovery times, and additional complications such as infection and tissue damage.

Percutaneous fixation techniques have emerged as a less invasive alternative, offering potential advantages such as reduced surgical trauma, shorter recovery times, and lower complication rates. However, existing percutaneous bone fixation systems are often limited in their ability to securely stabilize bone segments, particularly in regions like the ribs where anatomical curvature and constant mechanical forces present additional challenges. Many current devices and methods lack the necessary adaptability and stability to accommodate complex fracture patterns and ensure proper alignment and fixation of bone segments. There is a need for an improved bone repair system designed specifically for percutaneous fixation of bone segments, such as rib bones.

SUMMARY

The various systems and methods of the present disclosure have been developed in response to the present state of the art, and in particular, in response to the problems and needs in the art that have not yet been fully solved by currently available fracture plating systems and methods.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a plate having one or more slots and configured to span the first fracture, a first fastener configured to be received in one of the one or more slots and secure the plate to the interior surface of the bone, a second fastener configured to be received in one of the one or more slots and secure the plate to the interior surface of the bone, and a first tether configured to apply a force directly to the first fastener and the second fastener to guide the plate, the first fastener, and the second fastener through the interior body cavity to the interior surface of the bone.

In the fracture plating system of any preceding paragraph, the first tether may be further configured to facilitate reduction of the first fracture by, with the first fastener and the second fastener secured to the interior surface on opposite sides of the first fracture, urging the first fastener and the second fastener towards each other.

In the fracture plating system of any preceding paragraph, the first tether may be further configured to guide the first fastener through a first hole in the bone and to guide the second fastener through a second hole in the bone, wherein the first hole and the second hole may be on opposite sides of the first fracture.

In the fracture plating system of any preceding paragraph, the bone may further include a second fracture. The plate may be further configured to stabilize the second fracture via attachment of the plate to the bone such that the plate may span the first fracture and the second fracture, and the fracture plating system may further include a third fastener configured to be received in one of the one or more slots and secure the plate to the interior surface of the bone, a fourth fastener configured to be received in one of the one or more slots and secure the plate to the interior surface of the bone; and a second tether configured to guide the third fastener and the fourth fastener to the interior surface of the bone.

In the fracture plating system of any preceding paragraph, the second tether may be further configured to guide the third fastener to a first slot of the one or more slots and to guide the fourth fastener to a second slot of the one or more slots.

In the fracture plating system of any preceding paragraph, the fracture plating system may further be configured to stabilize three or more fractures of the bone, wherein the plate may be further configured to span the three or more fractures and the fracture plating system may further include multiple tethers each configured to guide two fasteners to the interior surface of the bone and to one of the one or more slots.

In the fracture plating system of any preceding paragraph, the bone may include a rib, and the first tether may be further configured to draw the plate, the first fastener, and the second fastener through a VATS portal to the interior surface of the bone.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a plate having one or more slots and configured to span the first fracture, a first fastener configured to be received in one of the one or more slots and secure the plate to the interior surface of the bone, and a first tether configured to apply a force directly to the first fastener and the second fastener to guide the plate, the first fastener, and the second fastener through the interior body cavity to the interior surface of the bone.

In the fracture plating system of any preceding paragraph, the first tether may be further configured to facilitate reduction of the first fracture by, with the first fastener and the second fastener secured to the interior surface on opposite sides of the first fracture, urging the first fastener and the second fastener towards each other.

In the fracture plating system of any preceding paragraph, the bone may include a rib, and the first tether may be further configured to draw the plate, the first fastener, and the second fastener through a VATS portal to the interior surface of the bone.

In the fracture plating system of any preceding paragraph, the bone may further include a second fracture, and the plate may be further configured to stabilize the second fracture via attachment of the plate to the bone such that the plate spans the first fracture and the second fracture. The fracture plating system may further include a third fastener configured to be received in one of the one or more slots and secure the plate to the interior surface of the bone, a fourth fastener configured to be received in one of the one or more slots and secure the plate to the interior surface of the bone, and a second tether configured to guide the third fastener and the fourth fastener to the interior surface of the bone.

In the fracture plating system of any preceding paragraph, the first fastener may include a first cannulation configured to receive a first end of the first tether, and the second fastener may include a second cannulation configured to receive a second end of the first tether.

In the fracture plating system of any preceding paragraph, the fracture plating system may further include a first locking nut configured to receive the first fastener and to cooperate with the first fastener to secure the plate to the interior surface of the bone, and a second locking nut configured to receive the second fastener and to cooperate with the second fastener to secure the plate to the interior surface of the bone.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a plate assembly having a plate including one or more slots and configured to span the first fracture, a first fastener coupled to one of the one or more slots and configured to secure the plate to the interior surface of the bone, and a second fastener coupled to one of the one or more slots and configured to secure the plate to the interior surface of the bone. The fracture plating system may also include a first tether configured to apply a force directly to the first fastener and the second fastener to guide the plate assembly through the interior body cavity to the interior surface of the bone.

In the fracture plating system of any preceding paragraph, the first tether may be further configured to draw the first fastener through a first hole in a first portion of the bone proximate a first side of the first fracture; and draw the second fastener through a second hole in a second portion of the bone proximate a second side of the first fracture.

In the fracture plating system of any preceding paragraph, the bone may further include a second fracture, and the plate may be further configured to stabilize the second fracture via attachment of the plate to the bone such that the plate spans the first fracture and the second fracture. The fracture plating system may further include a third fastener configured to be received in one of the one or more slots and secure the plate to the interior surface of the bone, a fourth fastener configured to be received in one of the one or more slots and secure the plate to the interior surface of the bone, and a second tether configured to guide the third fastener and the fourth fastener to the interior surface of the bone.

In the fracture plating system of any preceding paragraph, the first tether may be further configured to facilitate reduction of the first fracture by, with the first fastener and the second fastener secured to the interior surface on opposite sides of the first fracture, urging the first fastener and the second fastener towards each other.

In the fracture plating system of any preceding paragraph, the bone may include a rib, and the first tether may be further configured to draw the plate assembly through a VATS portal to the interior surface of the bone.

In the fracture plating system of any preceding paragraph, the first fastener may include a first cannulation configured to receive a first end of the first tether, and the second fastener may include a second cannulation configured to receive a second end of the first tether.

In the fracture plating system of any preceding paragraph, the fracture plating system may further include a first locking nut configured to receive the first fastener and to cooperate with the first fastener to secure the plate to the interior surface of the bone, and a second locking nut configured to receive the second fastener and to cooperate with the second fastener to secure the plate to the interior surface of the bone.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a first plate having a first slot having a first slot width, a first slot length, a first longitudinal axis, and a first threaded portion, wherein the first plate may be configured to span the first fracture, and a first fastener having a first head portion and a second threaded portion, wherein the first fastener may be configured to be received in the first slot and secure the first plate to the interior surface of the bone. The first slot width and the first head portion may be sized to prevent the first head portion from passing through the first slot, and the first threaded portion may be configured to threadably engage the second threaded portion to allow the second threaded portion to threadably pass through the first threaded portion, thereby positioning the first slot between the first head portion and the second threaded portion, resulting in the first fastener being captive in the first slot.

In the fracture plating system of any preceding paragraph, the first fastener and the first slot may be configured to allow translation of the first fastener along the first longitudinal axis, with the first fastener captively received in the first slot, and the first fastener may be further configured so that, with the first fastener captively received in the first slot, the first fastener may be moveable relative to the first plate along a third longitudinal axis of the first fastener.

In the fracture plating system of any preceding paragraph, the first fastener may be configured to reside captive within the first slot independently of engagement of any protruding feature of the first head portion with the first plate.

In the fracture plating system of any preceding paragraph, the fracture plating system may further include a second plate having a second plate length and a second slot, wherein the second plate may be configured to span the first fracture, a second fastener configured to be captively received in the first slot to secure the first plate to the interior surface of the bone or captively received in the second slot to secure the second plate to the interior surface of the bone. One of the first plate and the second plate may be selected based on patient anatomy and a location of the first fracture, two of the first fastener and the second fastener may be selected based on patient anatomy and the location of the first fracture, and the fracture plating system may be configured to be assembled during a surgical procedure prior to implantation within the patient.

In the fracture plating system of any preceding paragraph, the bone may include a rib, and the fracture plating system may further include a tether configured to draw the first plate and two of the first fastener and the second fastener through a VATS portal to the interior surface of the bone.

In the fracture plating system of any preceding paragraph, the first fastener may include a first fastener length, and the second fastener may include a second fastener length, different than the first fastener length.

In the fracture plating system of any preceding paragraph, the fracture plating system may further include a first locking nut having a first body length, and a second locking nut having a second body length, different than the first body length, wherein the first locking nut and the second locking nut may be interchangeably securable to the first fastener and the second fastener.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a first plate having a first slot extending along a first longitudinal axis of the first plate, wherein the first plate may be configured to span the first fracture, a first fastener configured to be captively received in the first slot and secure the first plate to the interior surface of the bone, and a first tether configured to guide the first plate and the first fastener to the interior surface of the bone. The first fastener may be configured so that, with the first fastener captively received in the first slot, the first fastener may be moveable relative to the first plate along a second longitudinal axis of the first fastener.

In the fracture plating system of any preceding paragraph, the first slot may include a first threaded portion and the first fastener may include a second threaded portion and a first head portion, wherein the first threaded portion may be configured to threadably engage the second threaded portion to allow the second threaded portion to pass through the first threaded portion, thereby positioning the first slot between the first head portion and the second threaded portion, resulting in the first fastener being captively received in the first slot.

In the fracture plating system of any preceding paragraph, the first fastener may include a first head portion, and the first fastener may be configured to reside captive within the first slot independently of engagement of any protruding feature of the first head portion with the first plate.

In the fracture plating system of any preceding paragraph, the bone may include a rib, and the first tether may be further configured to draw the first plate and the first fastener through a VATS portal to the interior surface of the bone.

In the fracture plating system of any preceding paragraph, the fracture plating system may further include a second plate having a second plate length and a second slot extending along a third longitudinal axis of the second plate, wherein the second plate may be configured to span the first fracture, a second fastener having a second fastener length and configured to be captively received in the first slot to secure the first plate to the interior surface of the bone or captively received in the second slot to secure the second plate to the interior surface of the bone. The first fastener may include a first fastener length, different than the second fastener length, one of the first plate and the second plate may be selected based on patient anatomy and a location of the first fracture, two of the first fastener and the second fastener may be selected based on patient anatomy and the location of the first fracture, and the fracture plating system may be configured to be assembled during a surgical procedure prior to implantation within the patient.

In the fracture plating system of any preceding paragraph, the fracture plating system may further include a first locking nut having a first body length, and a second locking nut having a second body length, different than the first body length, wherein the first locking nut and the second locking nut may be interchangeably securable to the first fastener and the second fastener.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a first plate having a first plate length and a first slot extending along a first longitudinal axis of the first plate, wherein the first plate may be configured to span the first fracture, a second plate having a second plate length, different from the first plate length, and a second slot extending along a second longitudinal axis of the second plate, wherein the second plate may be configured to span the first fracture, a first fastener configured to be captively receivable in either of the first slot and the second slot to secure either of the first plate and the second plate to the interior surface of the bone, and a second fastener configured to be captively receivable in either of the first slot and the second slot to secure either of the first plate and the second plate to the interior surface of the bone.

In the fracture plating system of any preceding paragraph, the first slot may include a first threaded portion and a first slot width, and the first fastener may include a second threaded portion and a head portion. The first slot width and the head portion may be sized to prevent the head portion from passing through the first slot, and the first threaded portion may be configured to threadably engage the second threaded portion to allow the second threaded portion to threadably pass through the first threaded portion, thereby positioning the first slot between the head portion and the second threaded portion, resulting in the first fastener being captively received in the first slot.

In the fracture plating system of any preceding paragraph, the first fastener and the first slot may be configured to allow translation of the first fastener along the first longitudinal axis, with the first fastener captively received in the first slot, and the first fastener may be further configured so that, with the first fastener captively received in the first slot, the first fastener may be moveable relative to the first plate along a third longitudinal axis of the first fastener.

In the fracture plating system of any preceding paragraph, the fracture plating system may further include a first locking nut having a first body length, and a second locking nut having a second body length, different than the first body length, wherein the first locking nut and the second locking nut may be interchangeably securable to the first fastener and the second fastener.

In the fracture plating system of any preceding paragraph, the first fastener may include a first fastener length, and the second fastener may include a second fastener length, different than the first fastener length.

In the fracture plating system of any preceding paragraph, the bone may include a rib, and the fracture plating system may further include a tether configured to draw the first plate and two of the first fastener and the second fastener through a VATS portal to the interior surface of the bone.

In the fracture plating system of any preceding paragraph, the first fastener may include a first head portion, and the first fastener may be configured to reside captive within the first slot independently of engagement of any protruding feature of the first head portion with the first plate.

In some embodiments, a fracture plating system may be configured to stabilize a first fracture and a second fracture of a bone of a patient, the bone may include an interior surface facing toward an interior body cavity of the patient, and an exterior surface facing away from the interior body cavity. The fracture plating system may include a plate configured to be placed on the interior surface, the plate having one or more slots and configured to span the first fracture and the second fracture, and four fasteners each configured to be received in the bone and in one of the one or more slots to secure the plate to the interior surface of the bone. The four fasteners may be configured to be received in the bone on opposite sides of each of the first fracture and the second fracture.

In the fracture plating system of any preceding paragraph, the fracture plating system may further include a first tether configured to guide a first two of the four fasteners to the interior surface of the bone, and a second tether configured to guide a second two of the four fasteners to the interior surface of the bone.

In the fracture plating system of any preceding paragraph, the bone may include a rib, the first tether may be further configured to draw the plate and a first two of the four fasteners through a VATS portal to the interior surface of the bone, and the second tether may be further configured to draw a second two of the four fasteners through the VATS portal to the interior surface of the bone.

In the fracture plating system of any preceding paragraph, the first tether may be further configured to draw a first one of the four fasteners through a first hole in a first portion of the bone proximate a first side of one of the first fracture and the second fracture, and draw a second one of the four fasteners through a second hole in a second portion of the bone proximate a second side of one of the first fracture and the second fracture.

In the fracture plating system of any preceding paragraph, each of the one or more slots may be configured to span at least one of the first fracture and the second fracture.

In the fracture plating system of any preceding paragraph, each of the one or more slots may be configured to receive at least two of the four fasteners.

In the fracture plating system of any preceding paragraph, the fracture plating system may further include four locking nuts each configured to receive one of the four fasteners and cooperate with one of the four fasteners to secure the plate to the interior surface of the bone.

In some embodiments, a fracture plating system may be configured to stabilize a first fracture and a second fracture of a bone of a patient, wherein the first fracture and the second fracture may define a flail segment of the bone, the bone may include an interior surface facing toward an interior body cavity of the patient, and an exterior surface facing away from the interior body cavity. The fracture plating system may include a plate having one or more slots extending along a longitudinal axis of the plate and configured to span the first fracture and the second fracture, and at least three fasteners configured to be captively received in the one or more slots. A first fastener and a second fastener may be configured to be received in the bone on opposite sides of the first fracture and the second fracture to secure the plate to the interior surface of the bone, and a third fastener may be configured to be received in the flail segment to secure the plate to the flail segment.

In the fracture plating system of any preceding paragraph, the fracture plating system may further include a tether configured to guide two of the at least three fasteners to the interior surface of the bone.

In the fracture plating system of any preceding paragraph, the tether may be further configured to guide the plate to the interior surface of the bone.

In the fracture plating system of any preceding paragraph, the bone may include a rib, and the tether may be further configured to draw the plate and two of the at least three fasteners through a VATS portal to the interior surface of the bone.

In the fracture plating system of any preceding paragraph, each of the one or more slots may be configured to span at least one of the first fracture and the second fracture.

In the fracture plating system of any preceding paragraph, the fracture plating system may further include at least three locking nuts configured to receive one of the at least three fasteners and cooperate with one of the at least three fasteners to secure the plate to the interior surface of the bone.

In some embodiments, a fracture plating system may be configured to stabilize multiple fractures of a bone of a patient, wherein the multiple fractures may define one or more flail segments, the bone may include an interior surface facing toward an interior body cavity of the patient, and an exterior surface facing away from the interior body cavity. The fracture plating system may include a plate having one or more slots extending along a longitudinal axis of the plate and configured to span the first fracture and the second fracture, and at least three fasteners configured to be captively received in the one or more slots. A first fastener and a second fastener may be configured to be received in the bone on opposite sides of the first fracture and the second fracture to secure the plate to the interior surface of the bone, and a third fastener may be configured to be received in the flail segment to secure the plate to the flail segment.

In the fracture plating system of any preceding paragraph, one of the one or more tethers may be further configured to guide the plate to the interior surface of the bone.

In the fracture plating system of any preceding paragraph, each of the one or more slots may be configured to span at least one of the multiple fractures.

In the fracture plating system of any preceding paragraph, the plurality of fasteners may be configured to be received in the bone on opposite sides of the multiple fractures to secure the plate to the interior surface of the bone.

In the fracture plating system of any preceding paragraph, the bone may include a rib, and one of the one or more tethers may be further configured to draw the plate and two of the plurality of fasteners through a VATS portal to the interior surface of the bone.

In the fracture plating system of any preceding paragraph, the fracture plating system may further include a plurality of locking nuts configured to receive one of the plurality of fasteners and cooperate with one of the plurality of fasteners to secure the plate to the interior surface of the bone.

In the fracture plating system of any preceding paragraph, each of the one or more slots may be configured to receive at least two of the plurality of fasteners.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a plate having one or more slots and configured to span the first fracture, two or more fasteners configured to be received in the one or more slots, and one or more tethers configured to guide the two or more fasteners to the interior surface of the bone. Each of the two or more fasteners may be configured to be received in a hole in the bone, and the two or more fasteners may be configured to secure the plate to the exterior surface of the bone.

In the fracture plating system of any preceding paragraph, the fracture plating system may further include two or more locking nuts configured to receive the two or more fasteners, wherein the two or more locking nuts may be configured to cooperate with the two or more fasteners to secure the plate to the exterior surface of the bone.

In the fracture plating system of any preceding paragraph, the two or more fasteners may each include a proximal end comprising a head portion, and a distal end opposite the proximal end, and, with the plate secured to the exterior surface of the bone, the two or more locking nuts may engage the plate and the head portion may contact the interior surface of the bone.

In the fracture plating system of any preceding paragraph, the bone may include a rib, and the one or more tethers may be further configured to draw the two or more fasteners through a VATS portal to the interior surface of the bone.

In the fracture plating system of any preceding paragraph, the two or more fasteners may each include a proximal end comprising a head portion, and a distal end opposite the proximal end, and, with the plate secured to the exterior surface of the bone, the head portion may not contact the plate.

In the fracture plating system of any preceding paragraph, the head portion may contact the interior surface and the distal end may extend from the exterior surface of the bone.

In the fracture plating system of any preceding paragraph, the one or more tethers may be further configured to guide the two or more fasteners to the one or more slots.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a plate having one or more slots and configured to span the first fracture, and two or more fasteners configured to secure the plate to the exterior surface of the bone. Each of the two or more fasteners may include a proximal end having a head portion, and a distal end opposite the proximal end, the distal end may be configured to be received in a hole in the bone, the distal end may be further configured to be received in one of the one or more slots, and, with the plate secured to the exterior surface of the bone, the head portion may not contact the plate.

In the fracture plating system of any preceding paragraph, the fracture plating system may further include two or more locking nuts configured to receive the two or more fasteners, wherein the two or more locking nuts may be configured to cooperate with the two or more fasteners to secure the plate to the exterior surface of the bone.

In the fracture plating system of any preceding paragraph, with the plate secured to the exterior surface of the bone, the two or more locking nuts may engage the plate.

In the fracture plating system of any preceding paragraph, with the plate secured to the exterior surface of the bone, the head portion may contact the interior surface of the bone.

In the fracture plating system of any preceding paragraph, the fracture plating system may further include a tether configured to guide the two or more fasteners to the one or more slots.

In the fracture plating system of any preceding paragraph, the bone may include a rib, and the tether may be further configured to draw the two or more fasteners through a VATS portal to the interior surface of the bone.

In the fracture plating system of any preceding paragraph, the head portion may contact the interior surface and the distal end may extend from the exterior surface of the bone.

In some embodiments, a fracture plating system may be configured to stabilize a first fracture of a bone of a patient, the bone may include an interior surface facing toward an interior body cavity of the patient, and an exterior surface facing away from the interior body cavity. The fracture plating system may include a plate having one or more slots and configured to span the first fracture, two or more fasteners each having a proximal end having a head portion, and a distal end opposite the proximal end, and two or more locking nuts configured to be received on the distal end. Each of the two or more fasteners may be configured to be received in a hole in the bone so that the head portion may contact the interior surface and the distal end may extend from the exterior surface of the bone, and the two or more locking nuts may be configured to cooperate with the two or more fasteners to secure the plate to the exterior surface of the bone.

In the fracture plating system of any preceding paragraph, the fracture plating system may further include a tether configured to guide the two or more fasteners to the interior surface of the bone.

In the fracture plating system of any preceding paragraph, the bone may include a rib, and the tether may be further configured to draw the two or more fasteners through a VATS portal to the interior surface of the bone.

In the fracture plating system of any preceding paragraph, the tether may be further configured to guide the two or more fasteners to the one or more slots.

In the fracture plating system of any preceding paragraph, each of the two or more fasteners may be configured to be received in a hole in the bone.

In the fracture plating system of any preceding paragraph, with the plate secured to the exterior surface of the bone, the head portion may not contact the plate.

These and other features and advantages of the present disclosure will become more fully apparent from the following description and appended claims or may be learned by the practice of the implants, systems, and methods set forth hereinafter.

BRIEF DESCRIPTION OF THE DRA WINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings.

FIG. 64A front view of a toggle fastener in an insertion configuration of a fracture plating system according to an embodiment of the present disclosure.

FIG. 64B is a front view of the toggle fastener of FIG. 64A in a deployed configuration.

FIG. 65 is a perspective view of a pair of toggle fasteners of FIG. 64A in a partially deployed configuration spanning an exemplary bone fracture.

FIG. 66 is a perspective view of a pair of toggle fasteners of FIG. 64A in a partially deployed configuration spanning an exemplary bone fracture.

FIG. 67 is a perspective view of a pair of toggle fasteners of FIG. 64A in a partially deployed configuration spanning an exemplary bone fracture.

Figure 68:
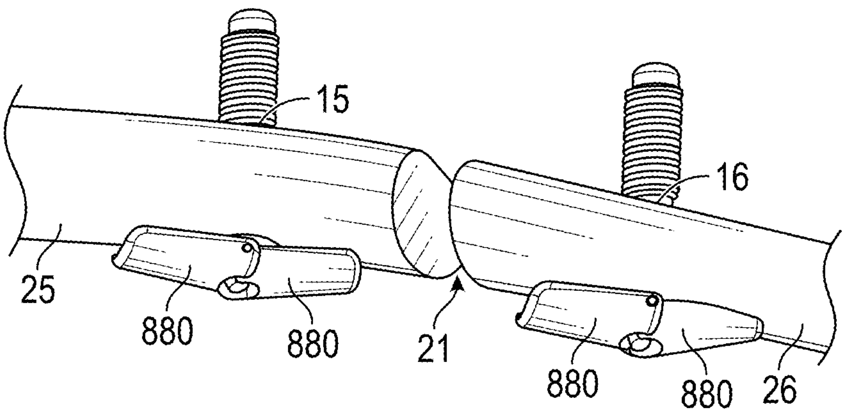

FIG. 68 is a perspective view of a pair of toggle fasteners of FIG. 64A in a partially deployed configuration spanning an exemplary bone fracture.

Figure 69:
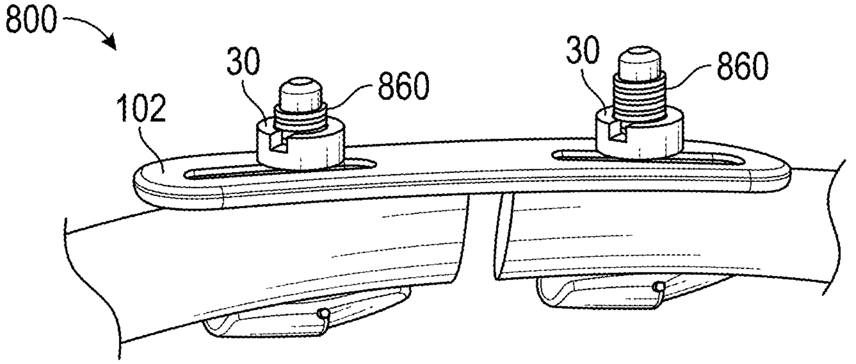

FIG. 69 is a perspective view of a fracture plating system including the toggle fastener of FIG. 64A according to an embodiment of the present disclosure spanning an exemplary bone fracture.

Figure 70:
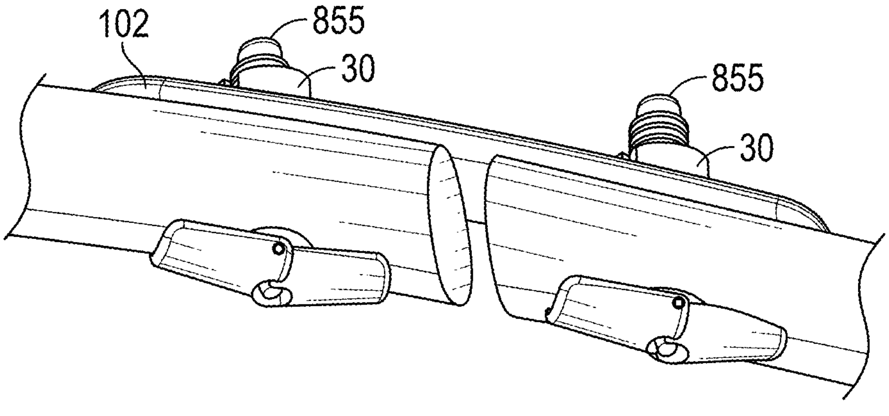

FIG. 70 is a bottom perspective view of the fracture plating system of FIG. 69 spanning an exemplary bone fracture.

Figure 2A:
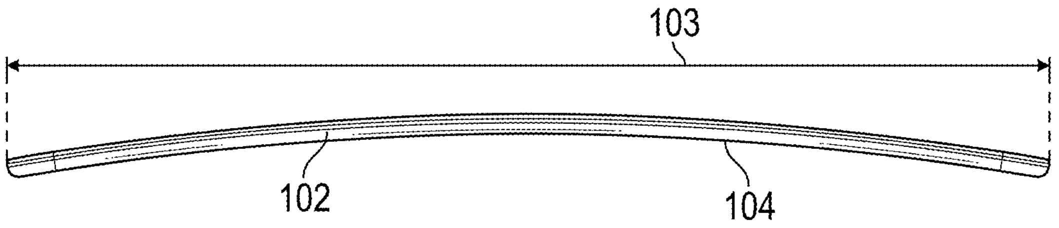
FIG. 2A is a front view of a plate of the fracture plating system of FIG. 1 according to an embodiment of the present disclosure.
Figure 71:
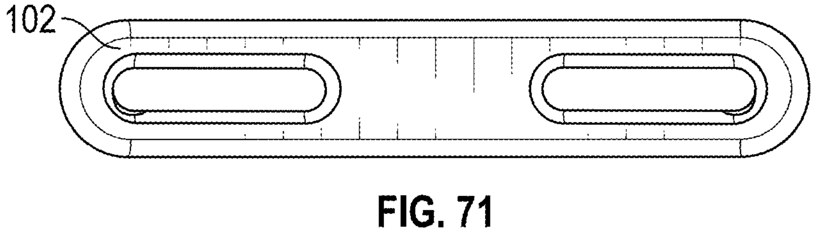

FIG. 71 is a bottom view of the plate of FIG. 2A.

Figure 72:
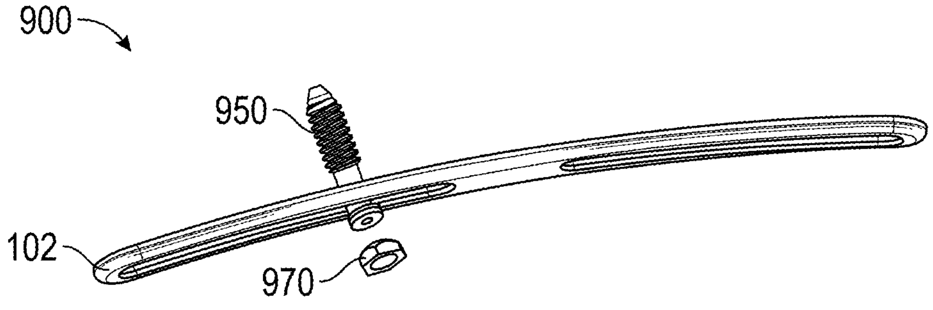

FIG. 72 is a perspective view of a fracture plating system according to an embodiment of the present disclosure in a partially assembled configuration.

Figure 73:
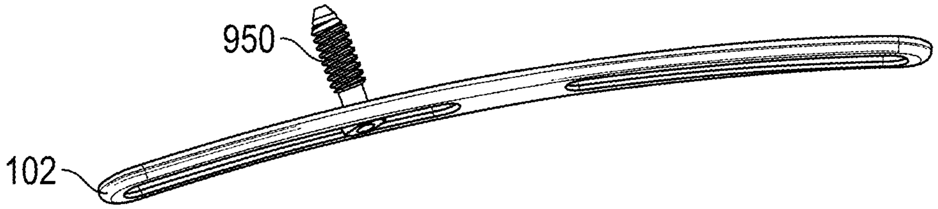

FIG. 73 is a perspective view of the fracture plating system of FIG. 72 in a partially assembled configuration.

Figure 74A:
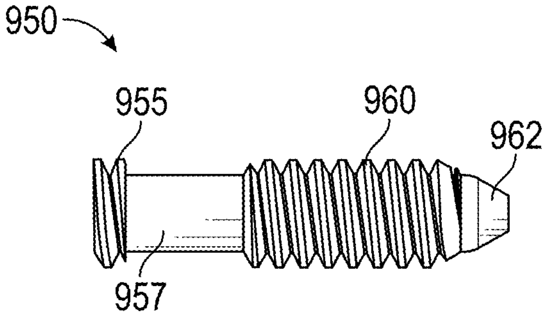

FIG. 74A is a front view of a post fastener of the fracture plating system of FIG. 72 according to an embodiment of the present disclosure.

Figure 74B:
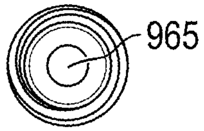

FIG. 74B is a side view of the post fastener of FIG. 74A.

Figure 75A:
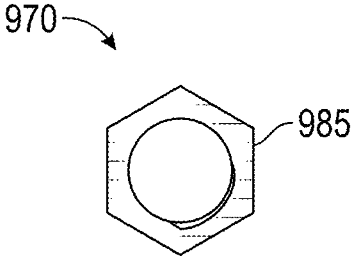

FIG. 75A is a front view of a nut of the fracture plating system of FIG. 72 according to an embodiment of the present disclosure.

Figure 75B:
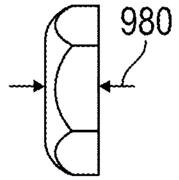

FIG. 75B is a side view of the nut of FIG. 75A.

Figure 75C:
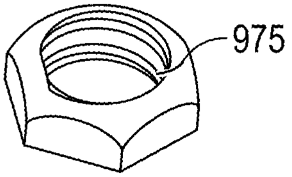

FIG. 75C is a perspective view of the nut of FIG. 75A.

Figure 76A:
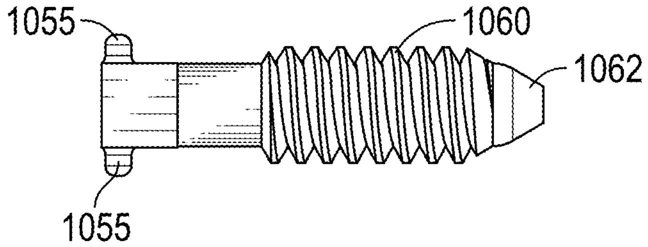
Figure 81:
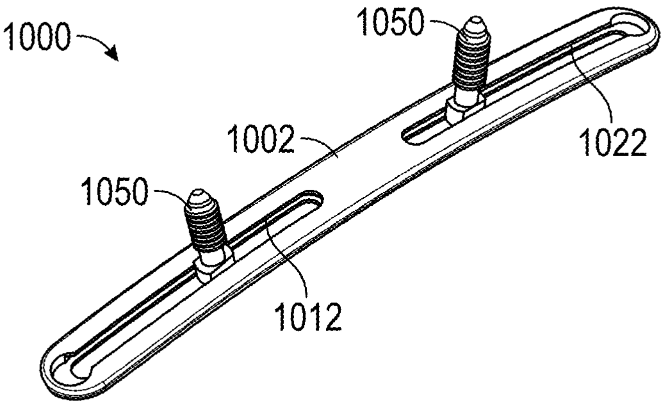

FIG. 76A is top view of a pin fastener of a fracture plating system of FIG. 81 according to an embodiment of the present disclosure.

Figure 76B:
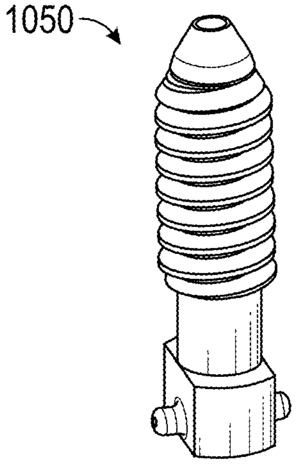

FIG. 76B is a perspective view of the pin fastener of FIG. 76A.

Figure 76C:
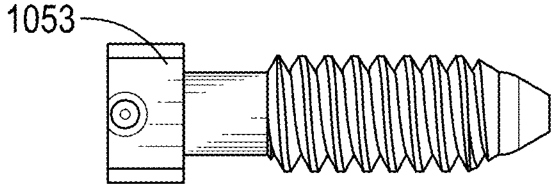

FIG. 76C is a front view of the pin fastener of FIG. 76A.

Figure 76D:
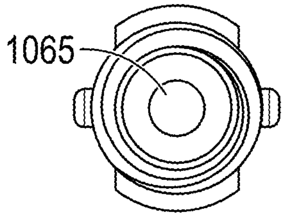

FIG. 76D is a side view of the pin fastener of FIG. 76A.

Figure 77A:
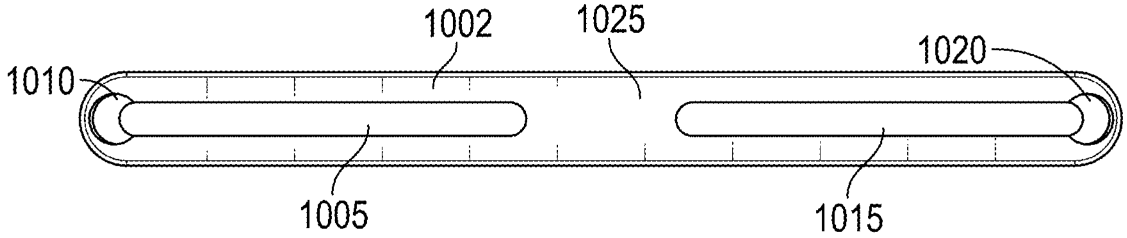

FIG. 77A is a top view of a plate of the fracture plating system of FIG. 81 according to an embodiment of the present disclosure.

Figure 77B:
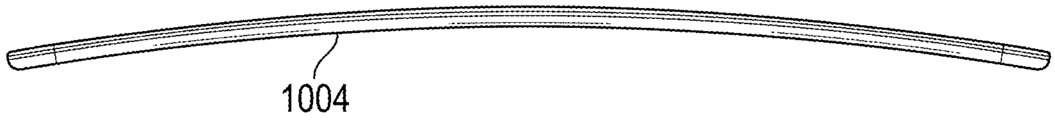

FIG. 77B is a front view of the plate of FIG. 77A.

Figure 78:
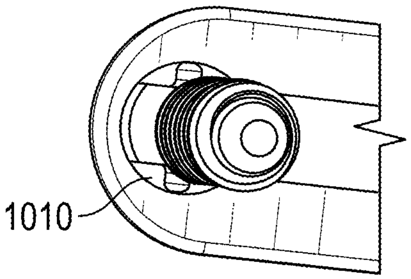

FIG. 78 is a partial top view of the fracture plating system of FIG. 81 in a partially assembled configuration.

Figure 79:
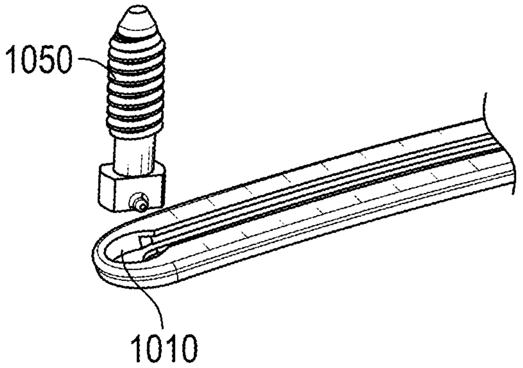

FIG. 79 is a partial perspective view of the fracture plating system of FIG. 81 in a partially assembled configuration.

Figure 80:
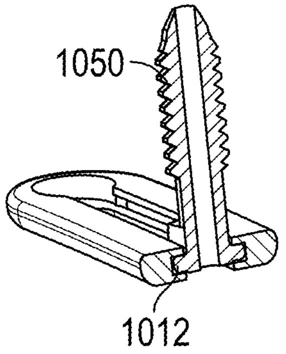

FIG. 80 is a perspective section view of the fracture plating system of FIG. 81.

FIG. 81 is a perspective view of a fracture plating system according to an embodiment of the present disclosure.

Figure 82:
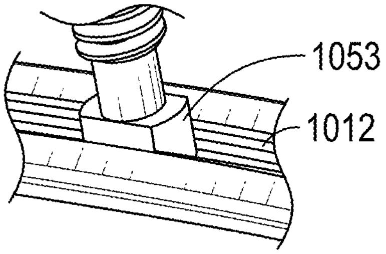

FIG. 82 is a partial perspective view of the fracture plating system of FIG. 81.

Figure 83:
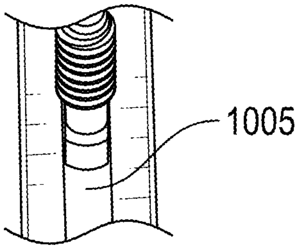

FIG. 83 is a partial perspective view of the fracture plating system of FIG. 81.

Figure 84:
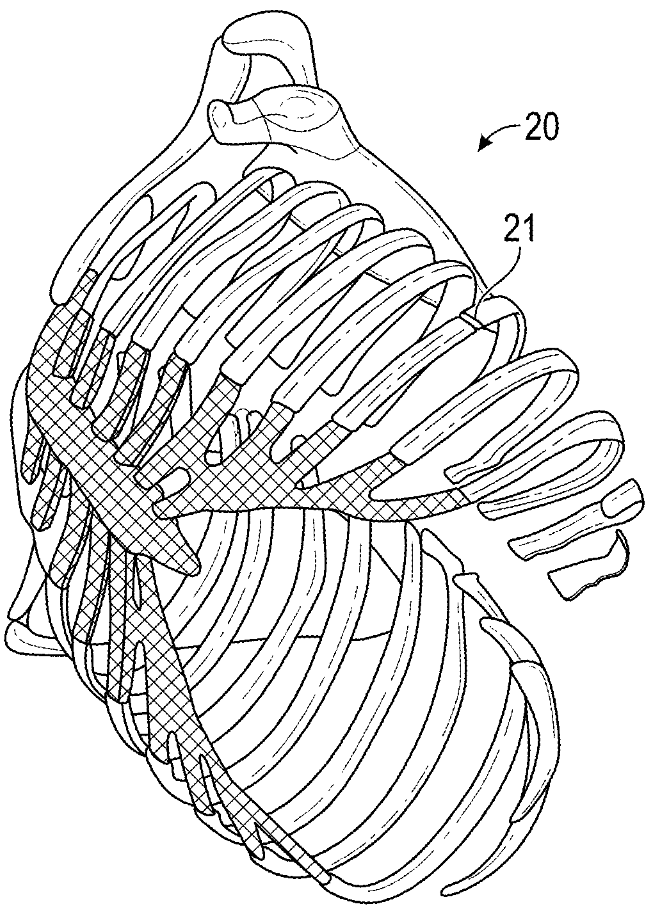

FIG. 84 is a perspective view of an exemplary rig cage with an exemplary bone fracture.

Figure 85:
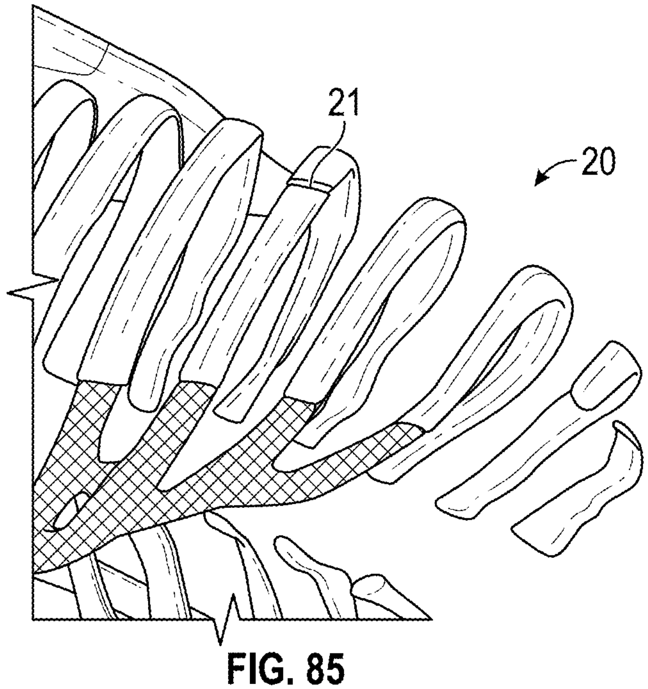

FIG. 85 is a partial perspective view of the exemplary rib cage of FIG. 84.

Figure 86:
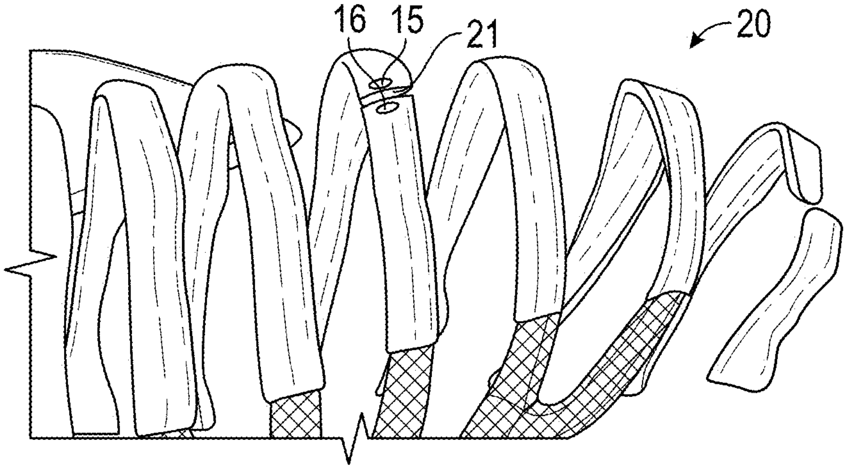

FIG. 86 is a partial perspective view of the exemplary rib cage of FIG. 84 illustrating a step in a method of deploying a fracture plating system according to an embodiment of the present disclosure.

Figure 87:
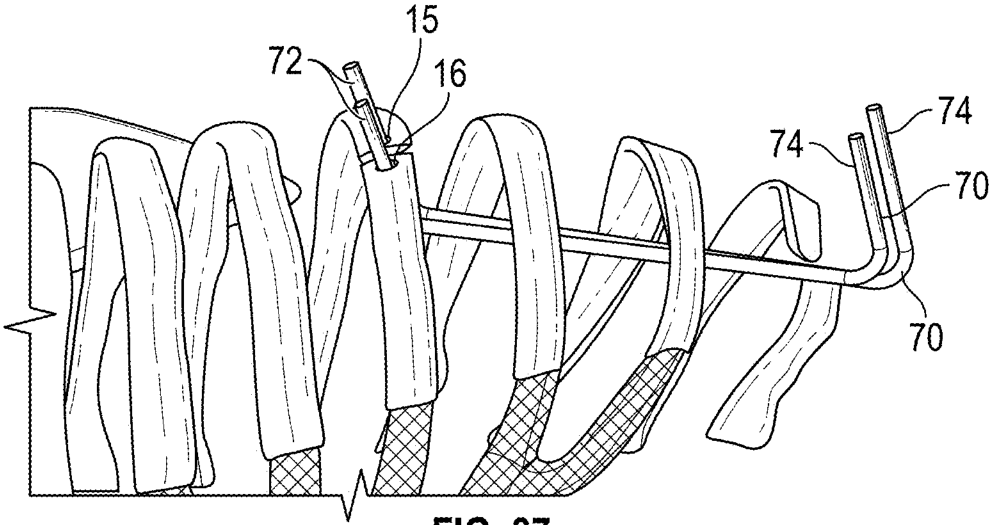

FIG. 87 is a partial perspective view of the exemplary rib cage of FIG. 84 illustrating a step in a method of deploying a fracture plating system according to an embodiment of the present disclosure.

Figure 88:
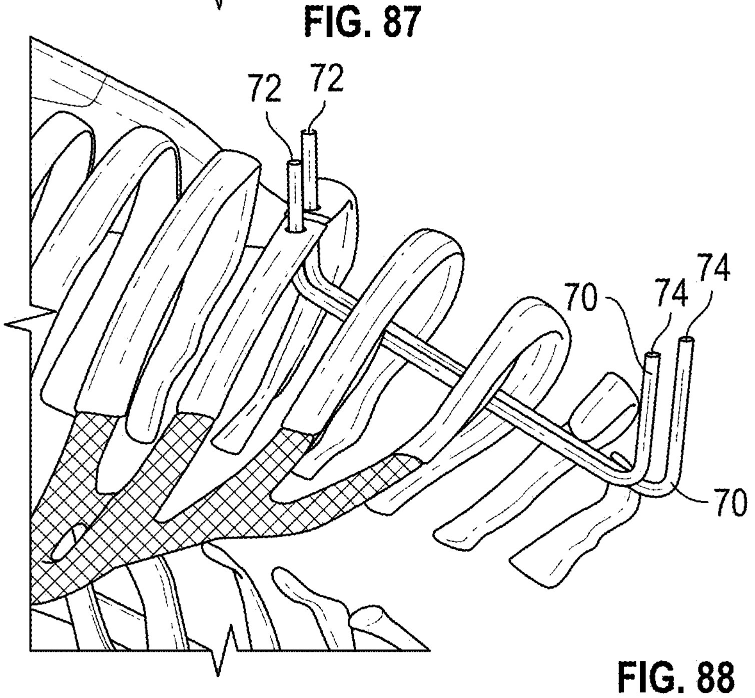

FIG. 88 is a partial perspective view of the exemplary rib cage of FIG. 84 illustrating a step in a method of deploying a fracture plating system according to an embodiment of the present disclosure.

Figure 89A:
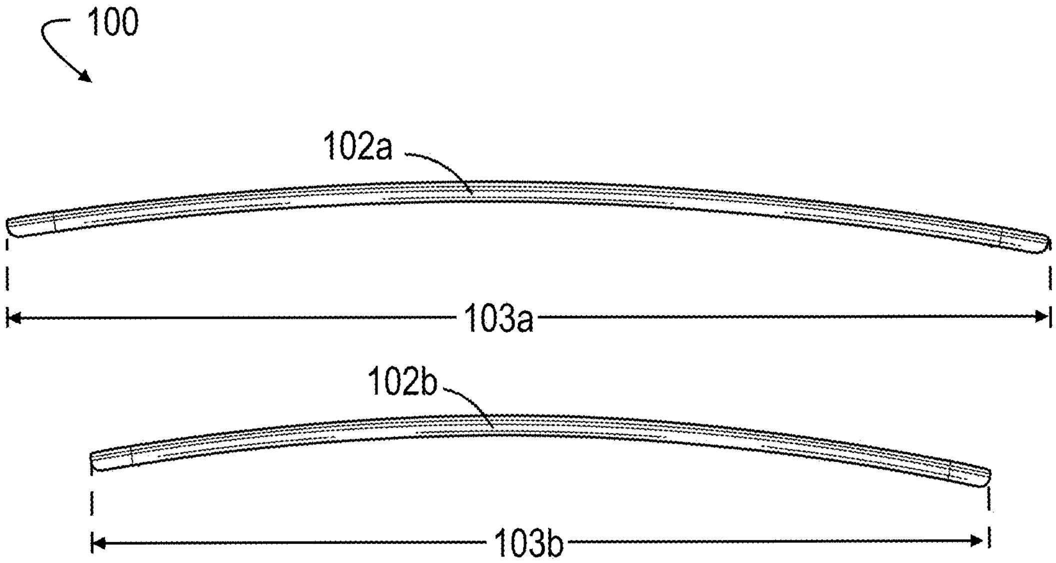

FIG. 89A is a front view of a set of differently sized plates according to an embodiment of the present disclosure.

Figure 89B:
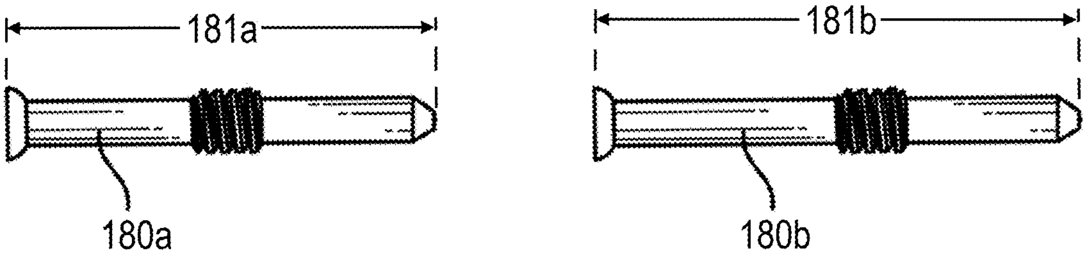

FIG. 89B is a front view of a set of differently sized fasteners according to an embodiment of the present disclosure.

Figure 89C:
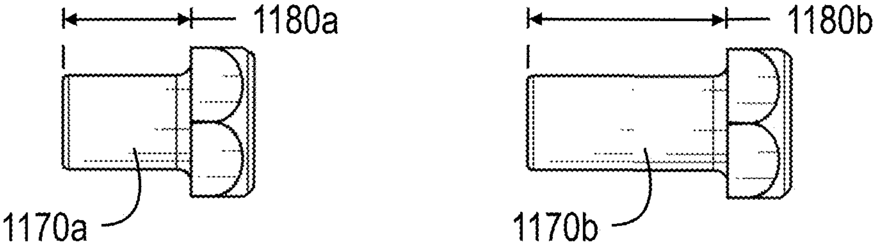

FIG. 89C is a front view of a set of differently sized locking nuts according to an embodiment of the present disclosure.

Figure 89D:
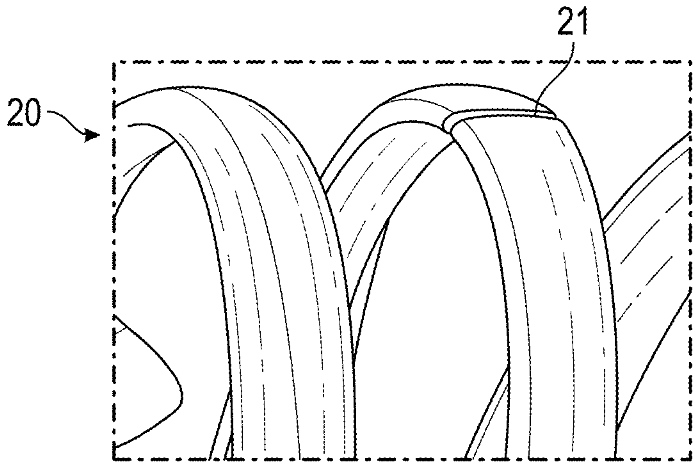

FIG. 89D Is a partial perspective view of an exemplary rib cage showing an exemplary fracture.

Figure 90:
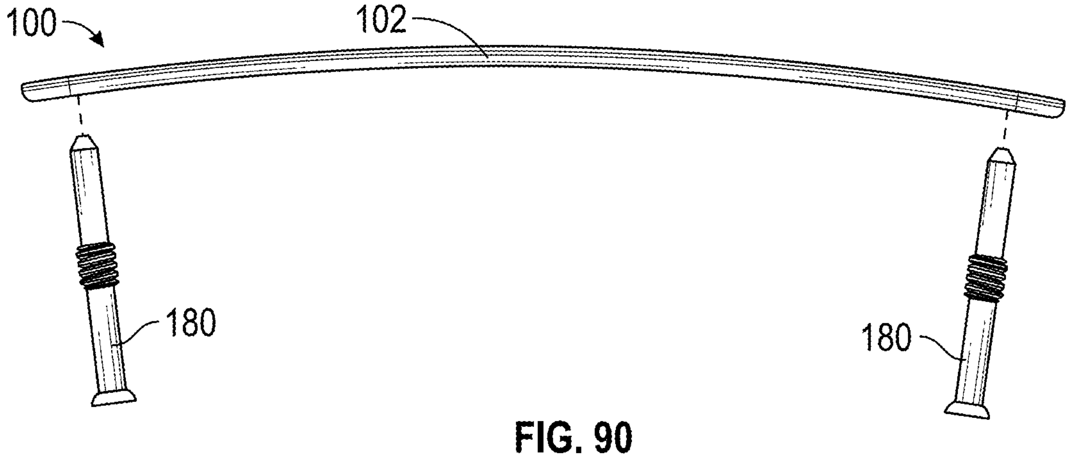

FIG. 90 is a front view of a fracture plating system illustrating a step in a method of deploying the fracture plating system according to an embodiment of the present disclosure.

Figure 91:
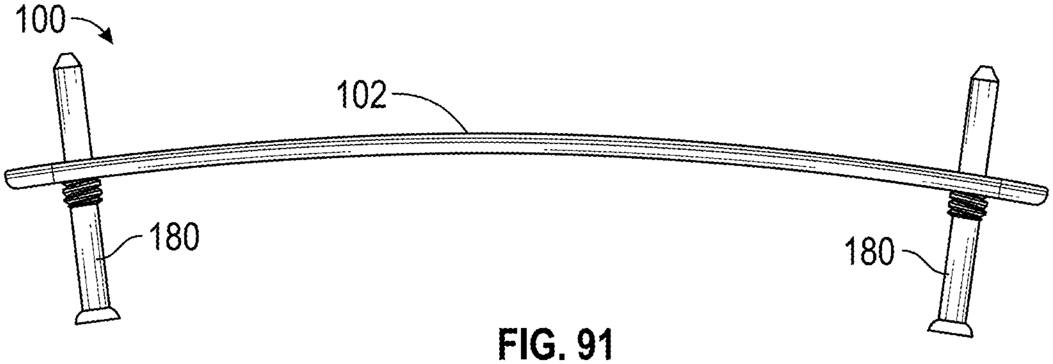

FIG. 91 is a front view of the fracture plating system of FIG. 90 illustrating a step in a method of deploying the fracture plating system according to an embodiment of the present disclosure.

Figure 92:
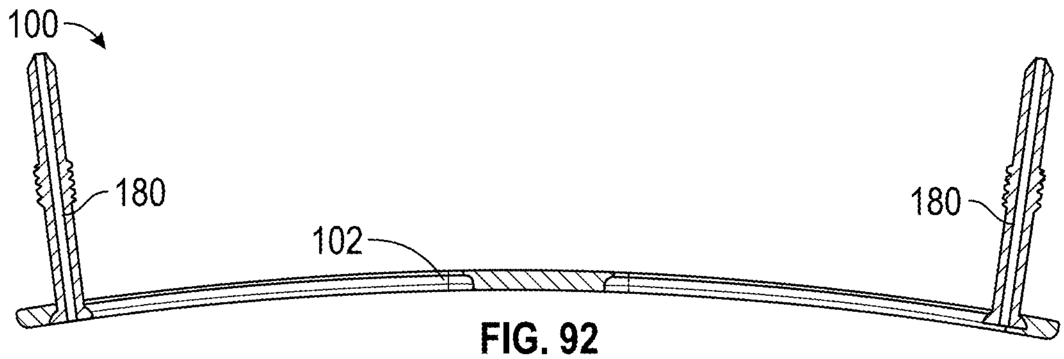

FIG. 92 is a front view of the fracture plating system of FIG. 90 illustrating a step in a method of deploying the fracture plating system according to an embodiment of the present disclosure.

Figure 93:
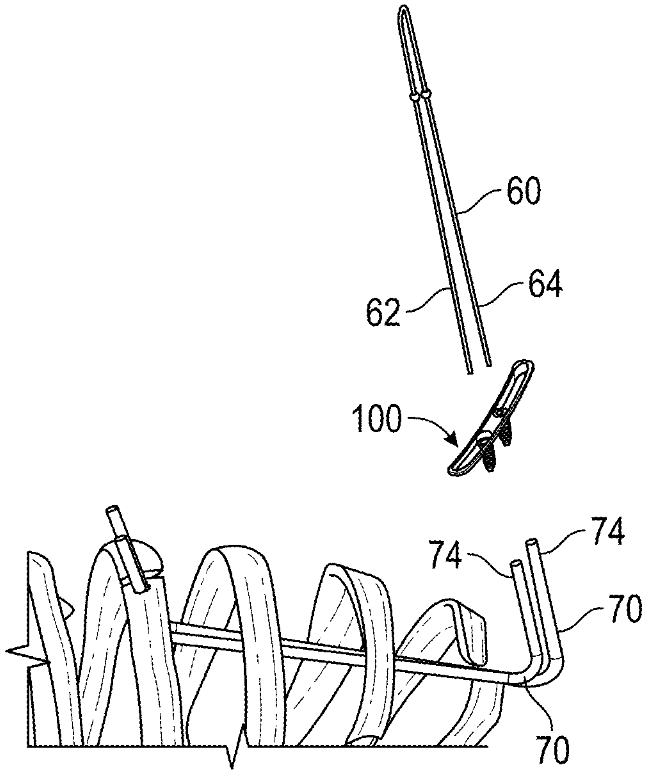

FIG. 93 is a partial perspective view of the exemplary rib cage of FIG. 84 illustrating a step in a method of deploying a fracture plating system according to an embodiment of the present disclosure.

Figure 94:
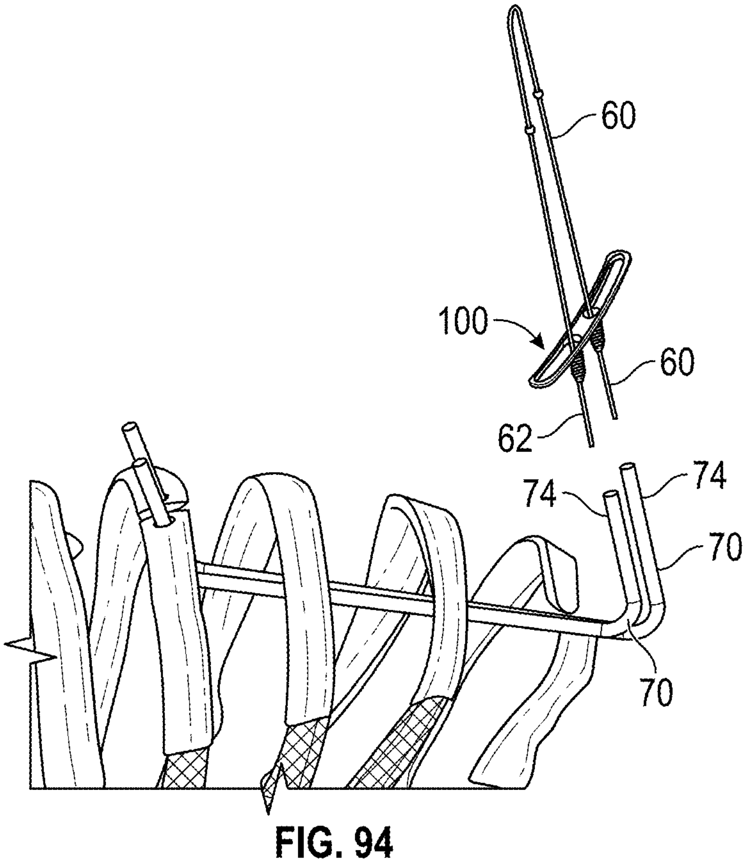

FIG. 94 is a partial perspective view of the exemplary rib cage of FIG. 84 illustrating a step in a method of deploying a fracture plating system according to an embodiment of the present disclosure.

Figure 95:
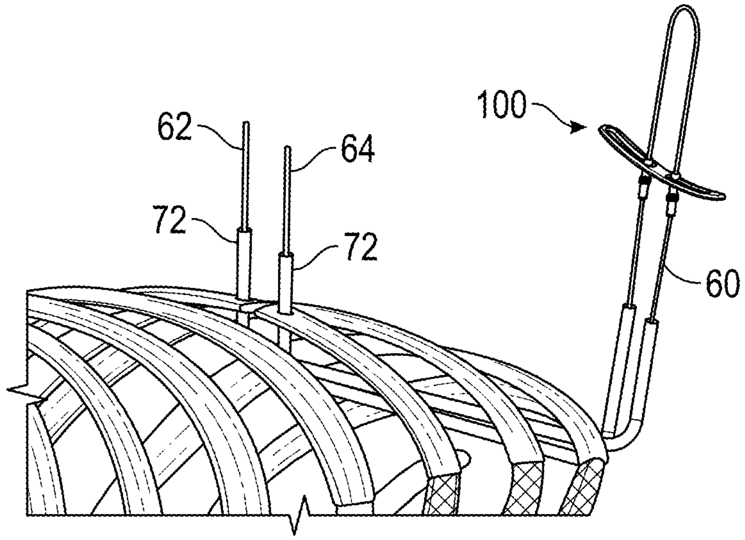

FIG. 95 is a partial perspective view of the exemplary rib cage of FIG. 84 illustrating a step in a method of deploying a fracture plating system according to an embodiment of the present disclosure.

Figure 96:
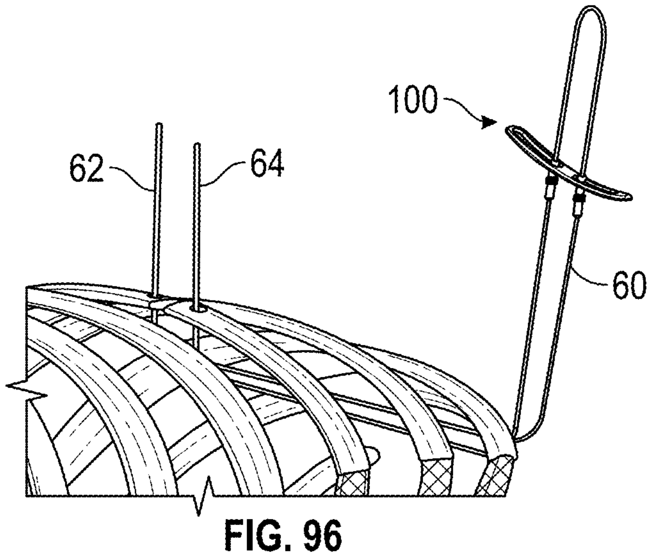

FIG. 96 is a partial perspective view of the exemplary rib cage of FIG. 84 illustrating a step in a method of deploying a fracture plating system according to an embodiment of the present disclosure.

Figure 97:
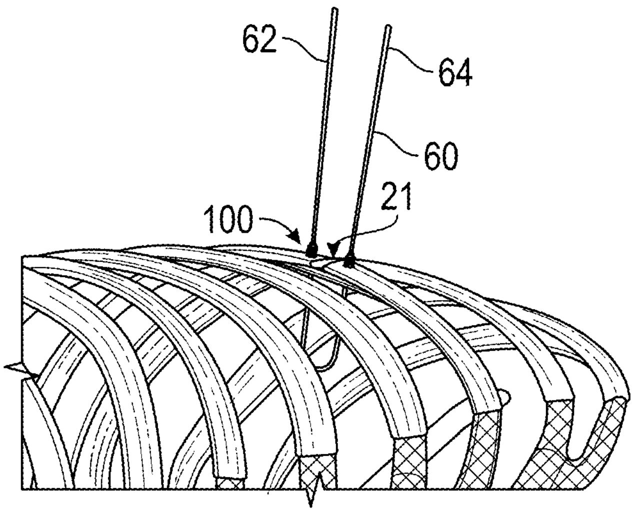

FIG. 97 is a partial perspective view of the exemplary rib cage of FIG. 84 illustrating a step in a method of deploying a fracture plating system according to an embodiment of the present disclosure.

Figure 98:
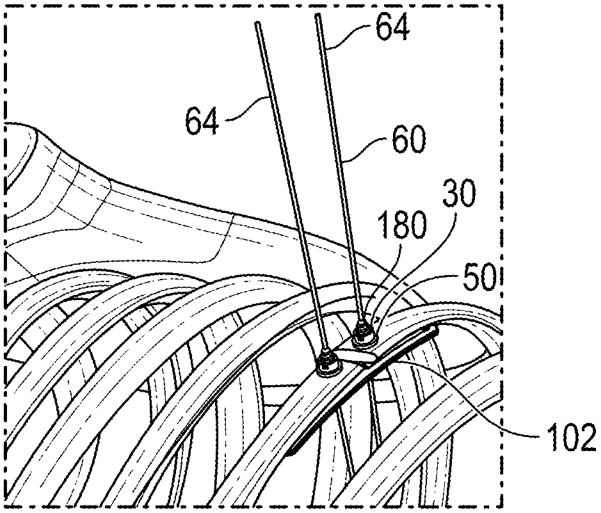

FIG. 98 is a partial perspective view of the exemplary rib cage of FIG. 84 illustrating a step in a method of deploying a fracture plating system according to an embodiment of the present disclosure.

Figure 99:
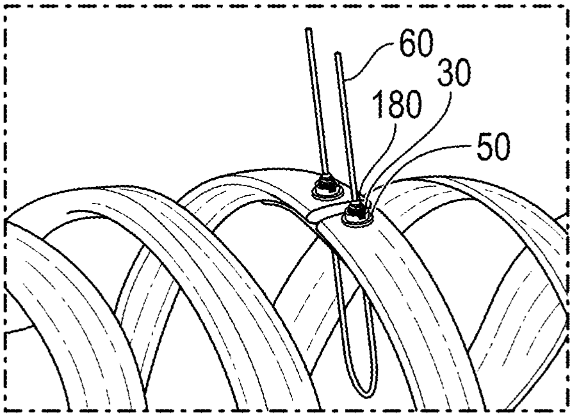

FIG. 99 is a partial perspective view of the exemplary rib cage of FIG. 84 illustrating a step in a method of deploying a fracture plating system according to an embodiment of the present disclosure.

Figure 100:
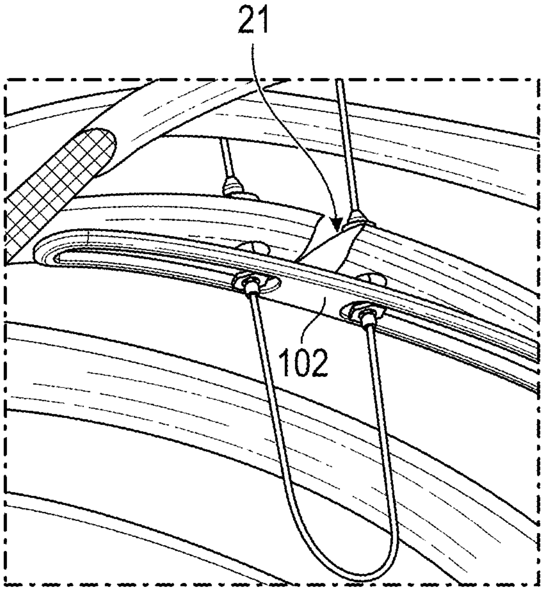

FIG. 100 is a partial perspective view of the exemplary rib cage of FIG. 84 illustrating a step in a method of deploying a fracture plating system according to an embodiment of the present disclosure.

Figure 101:
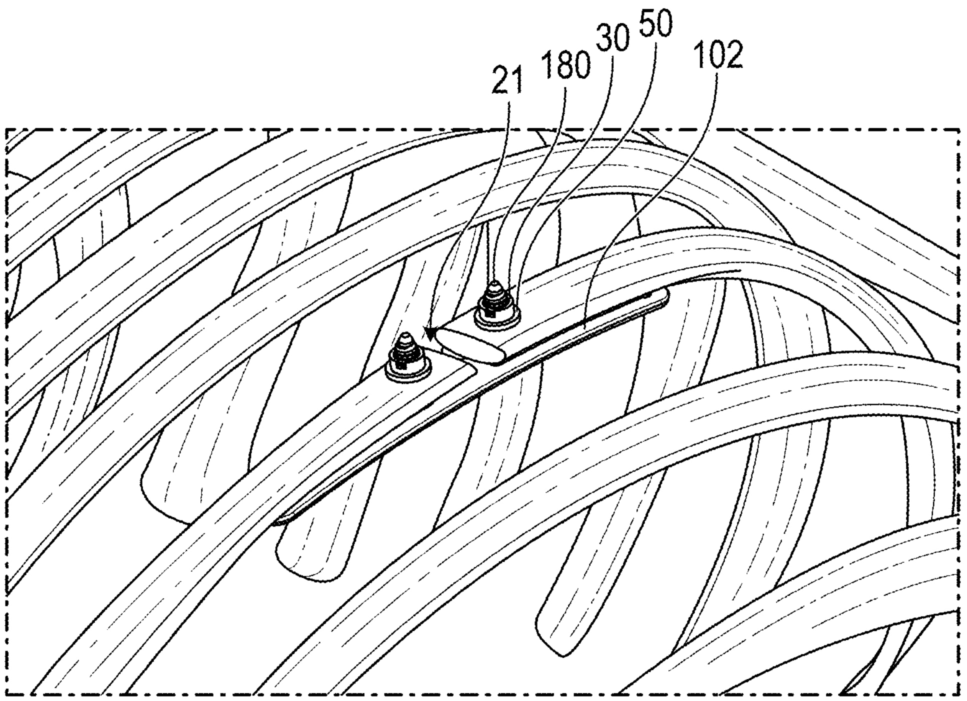

FIG. 101 is a partial perspective view of the exemplary rib cage of FIG. 84 illustrating a step in a method of deploying a fracture plating system according to an embodiment of the present disclosure.

Figure 102:
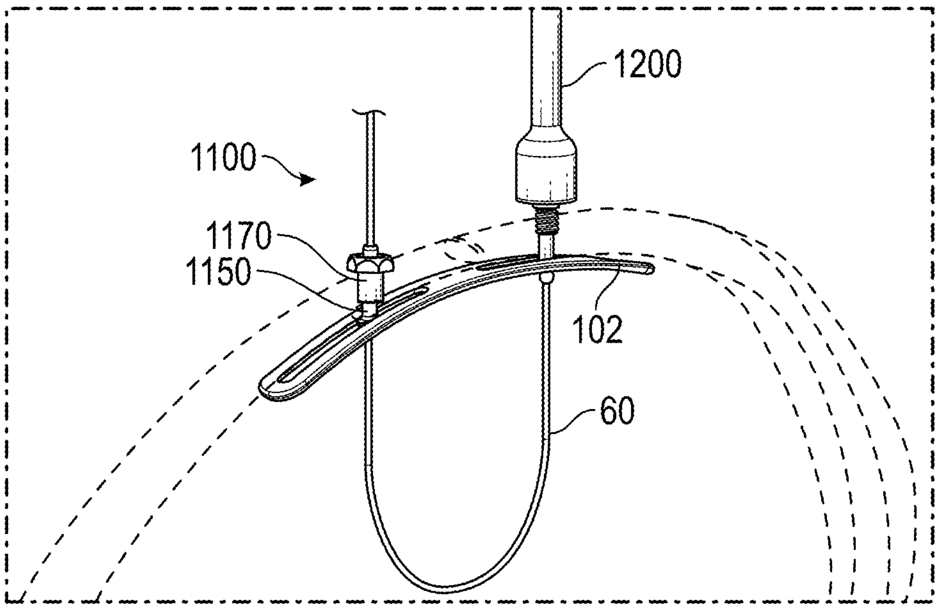

FIG. 102 is a perspective view of a fracture plating system according to an embodiment of the present disclosure spanning an exemplary bone fracture.

Figure 103:
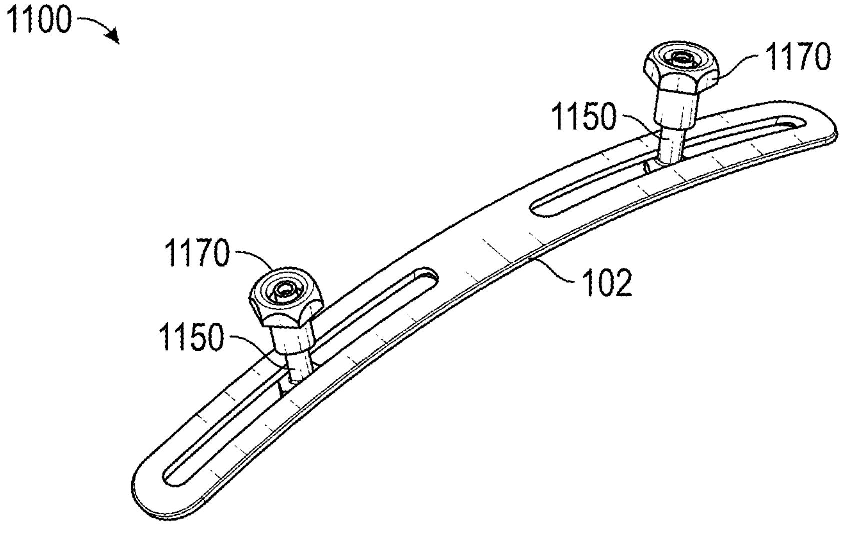

FIG. 103 is a perspective view of a fracture plating system of FIG. 102.

Figure 104A:
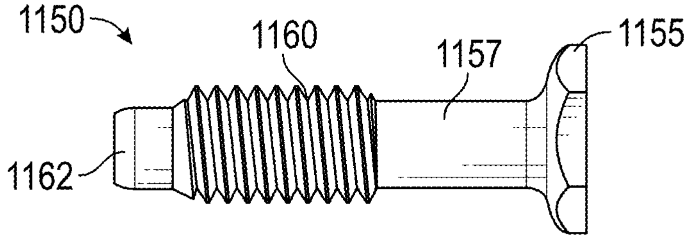

FIG. 104A is a front view of an anti-rotation fastener of the fracture plating system of FIG. 102 according to an embodiment of the present disclosure.

Figure 104B:
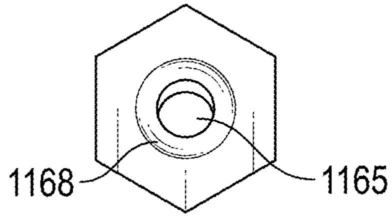

FIG. 104B is a side view of the anti-rotation fastener of FIG. 104A.

Figure 105A:
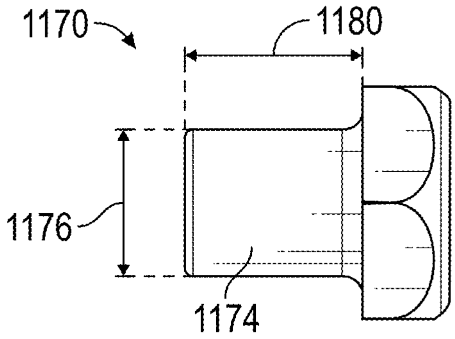

FIG. 105A is a front view of a locking nut of the fracture plating system of FIG. 102 according to an embodiment of the present disclosure.

Figure 105B:
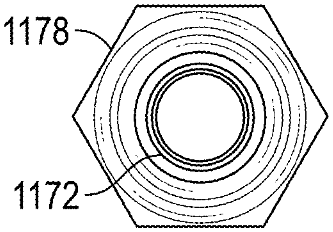

FIG. 105B is a side view of the locking nut of FIG. 105A.

Figure 106B:
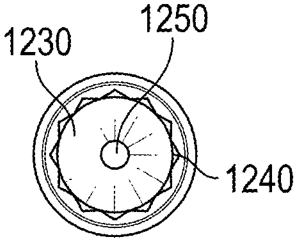
Figure 106A:
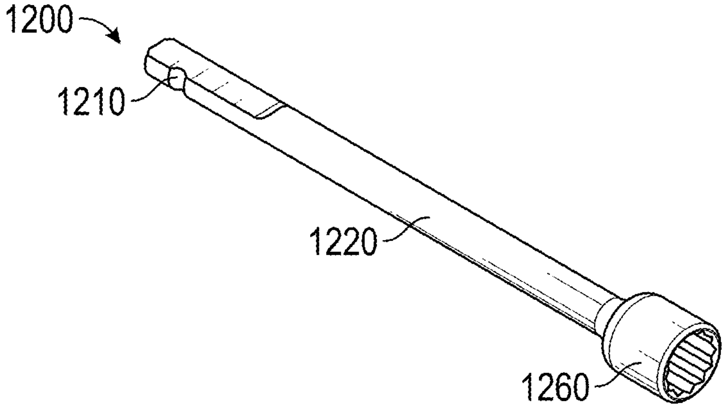

FIG. 106A is a perspective view of a driver of the fracture plating system of FIG. 102 according to an embodiment of the present disclosure.

FIG. 106B is a side view of the driver of FIG. 106A.

Figure 106C:
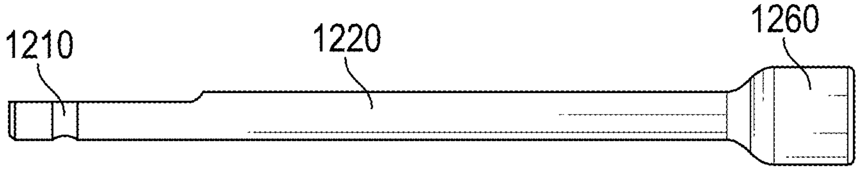

FIG. 106C is a front view of the driver of FIG. 106A.

Figure 107:
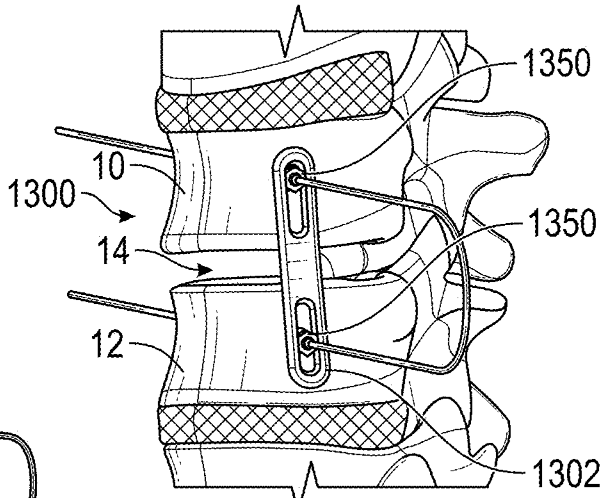

FIG. 107 is a front perspective view of a spinal fixation plating system, secured to an exemplary portion of a spine, according to an embodiment of the present disclosure.

Figure 108:
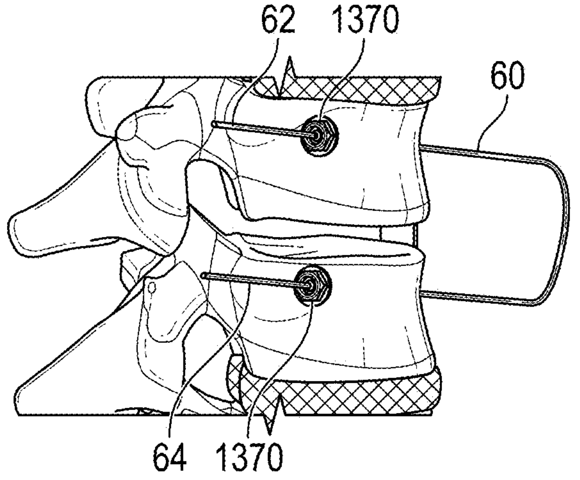

FIG. 108 is a rear perspective view of the spinal fixation plating system of FIG. 107 secured to an exemplary portion of a spine.

Figure 109:
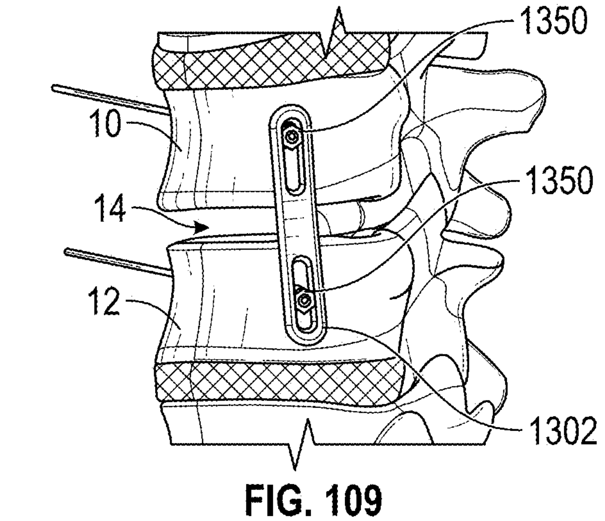

FIG. 109 is a front perspective view of the spinal fixation plating system of FIG. 107 secured to an exemplary portion of a spine.

Figure 110:
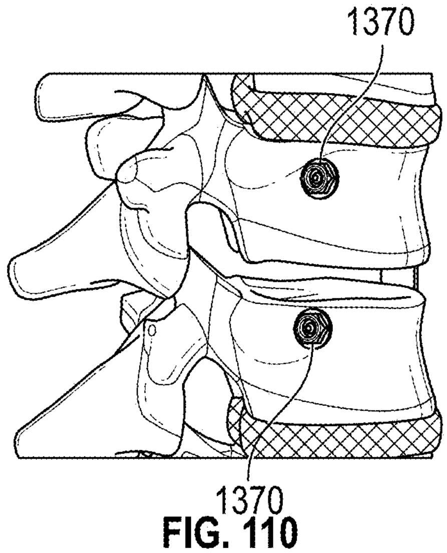

FIG. 110 is a rear perspective view of the spinal fixation plating system of FIG. 107 secured to an exemplary portion of a spine.

Figure 111A:
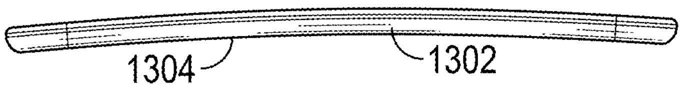

FIG. 111A is a front view of a plate of the spinal fixation plating system of FIG. 107 according to an embodiment of the present disclosure.

Figure 111B:
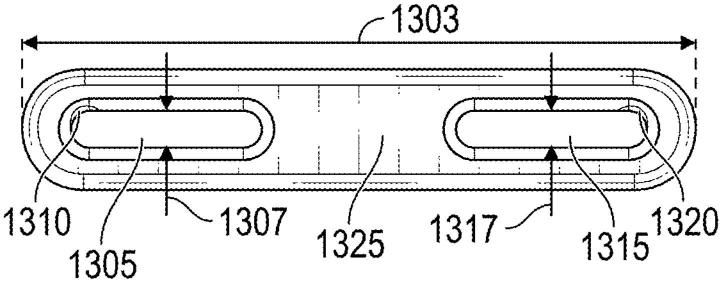

FIG. 111B is a bottom view of the plate of FIG. 111A.

Figure 112A:
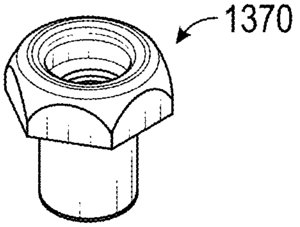

FIG. 112A is a perspective view of a locking nut of the spinal fixation plating system of FIG. 107 according to an embodiment of the present disclosure.

Figure 112B:
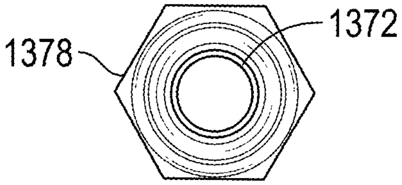

FIG. 112B is a front view of the locking nut of FIG. 112A.

Figure 112C:
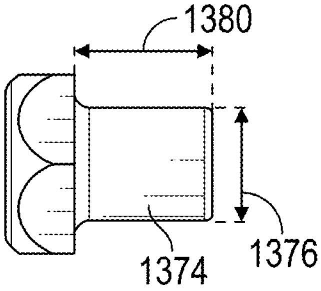

FIG. 112C is a side view of the locking nut of FIG. 112A.

Figure 113A:
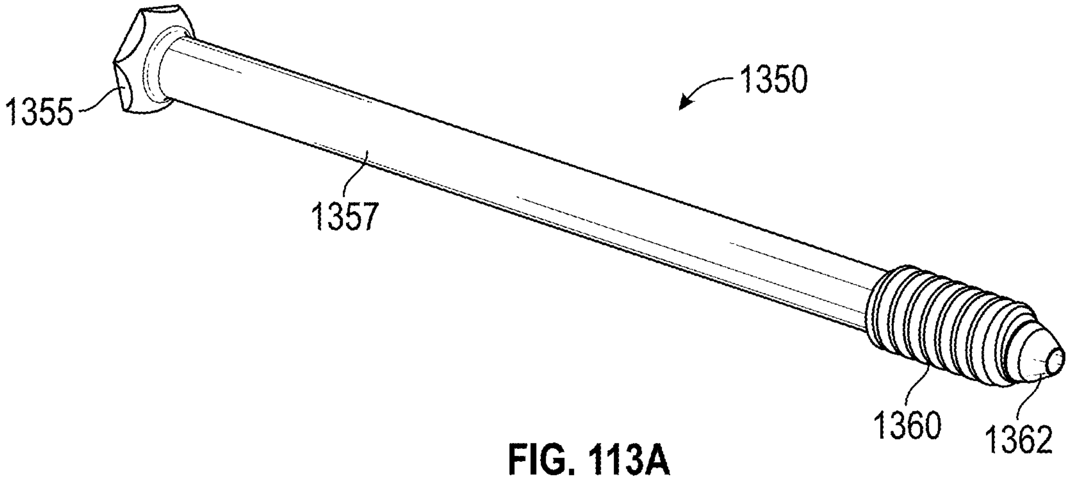

FIG. 113A is a perspective view of an anti-rotation fastener of the spinal fixation plating system of FIG. 107 according to an embodiment of the present disclosure.

Figure 113B:
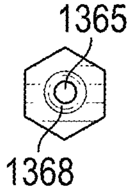

FIG. 113B is a front view of the anti-rotation fastener of FIG. 113A.

Figure 113C:
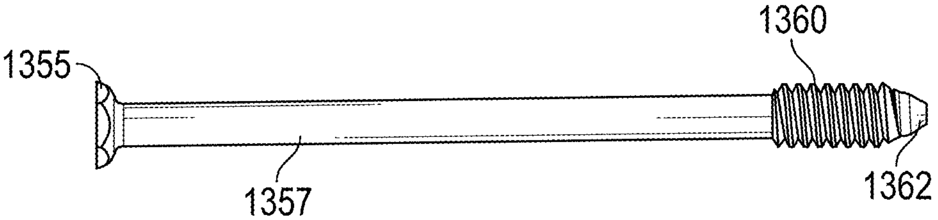

FIG. 113C is a side view of the anti-rotation fastener of FIG. 113A.

Figure 114:
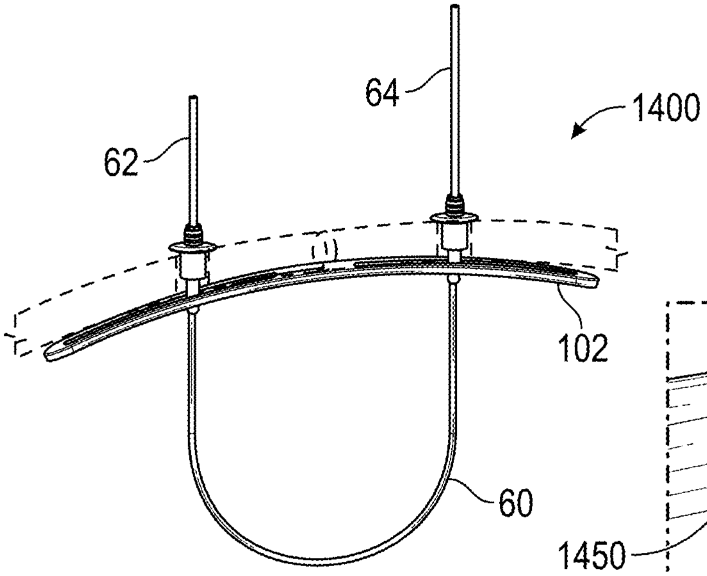

FIG. 114 is a front view of a fracture plating system according to an embodiment of the present disclosure spanning an exemplary bone fracture.

Figure 115:
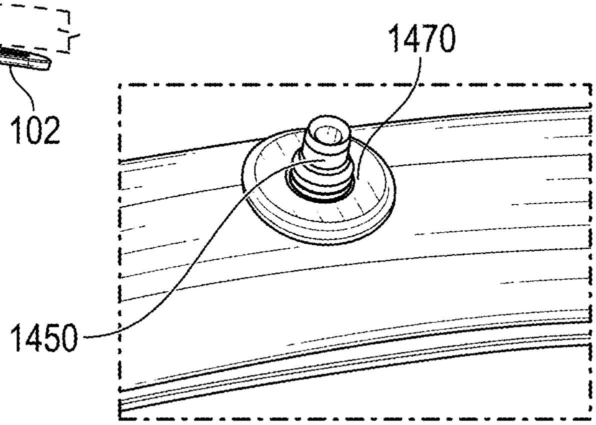

FIG. 115 is a partial perspective view of the fracture plating system of FIG. 114.

Figure 116:
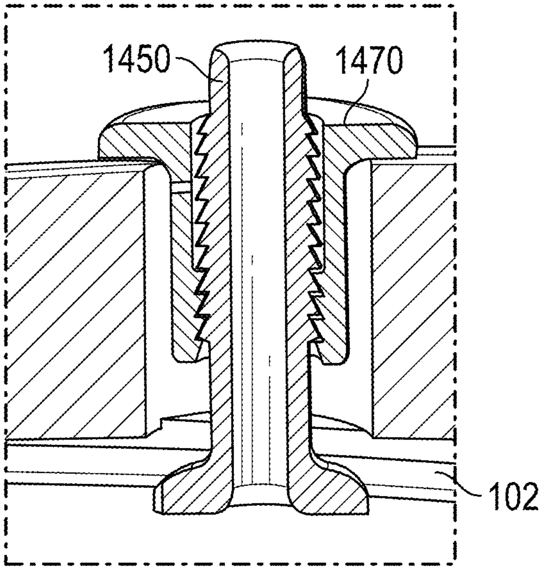

FIG. 116 is a partial section view of the fracture plating system of FIG. 114.

Figure 117:
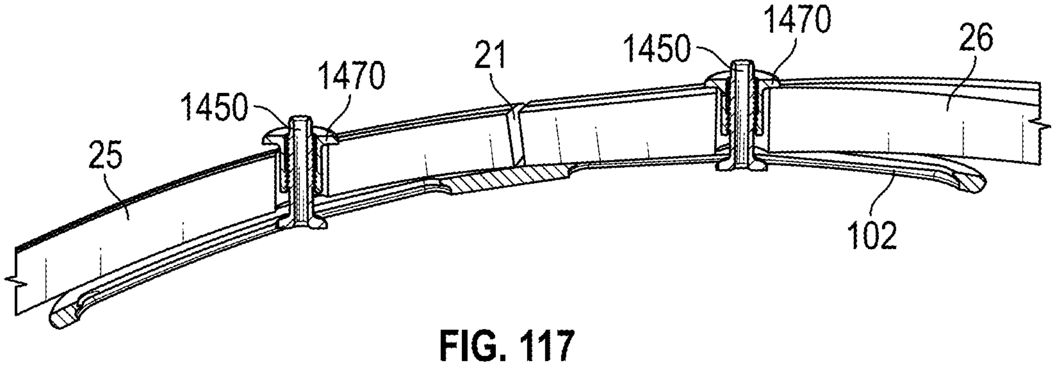

FIG. 117 is a front section view of the fracture plating system of FIG. 114.

Figure 118A:
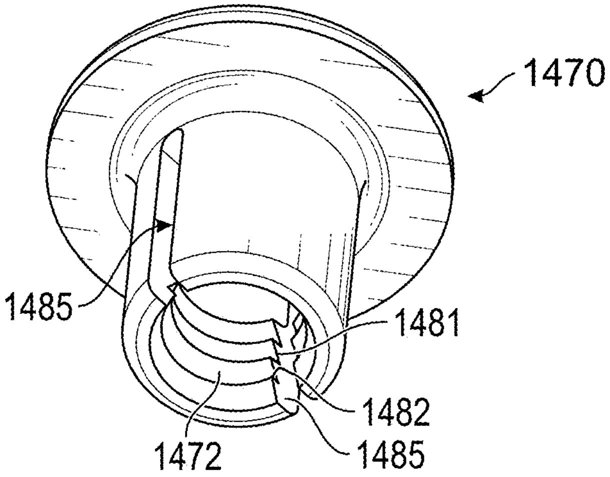

FIG. 118A is a bottom perspective view of a ratchet cap of the fracture plating system of FIG. 114 according to an embodiment of the present disclosure.

Figure 118B:
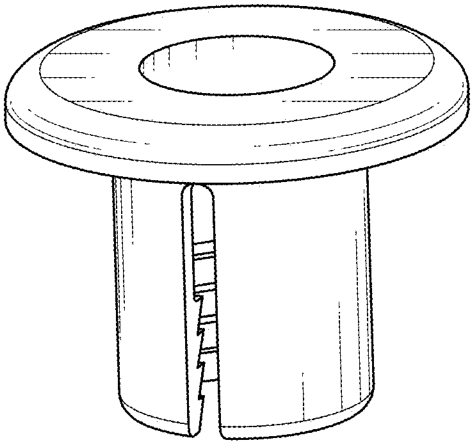

FIG. 118B is front perspective view of the ratchet cap of FIG. 118A.

Figure 118C:
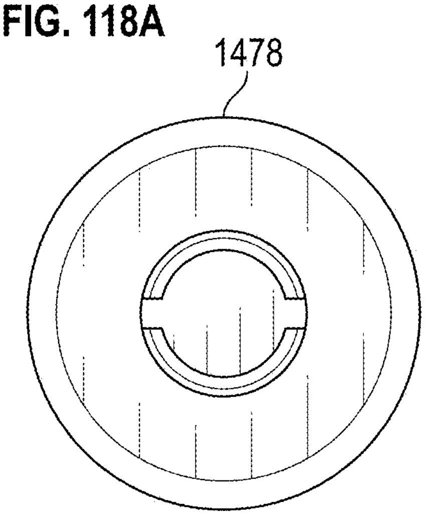

FIG. 118C is a front view of the ratchet cap of FIG. 118A.

Figure 118D:
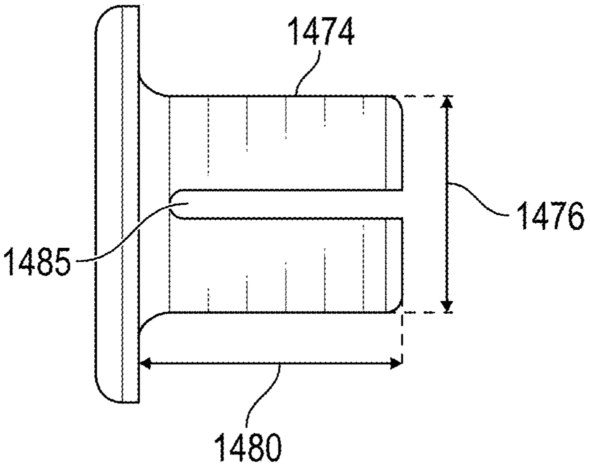

FIG. 118D is a side view of the ratchet cap of FIG. 118A.

Figure 119A:
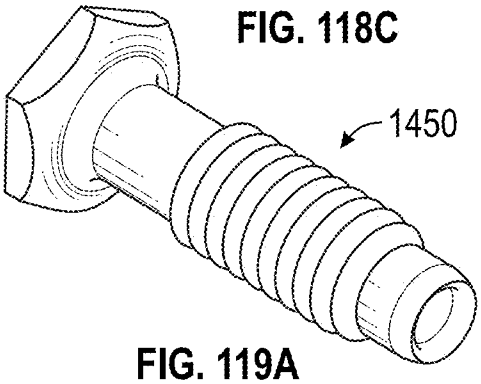

FIG. 119A is a perspective view of a ratchet fastener of the fracture plating system of FIG. 114 according to an embodiment of the present disclosure.

Figure 119B:
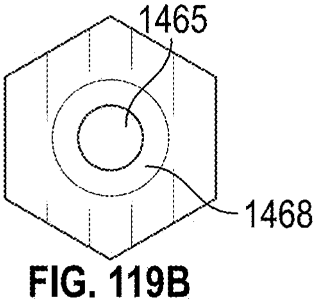

FIG. 119B is a front view of the ratchet fastener of FIG. 119A.

Figure 119C:
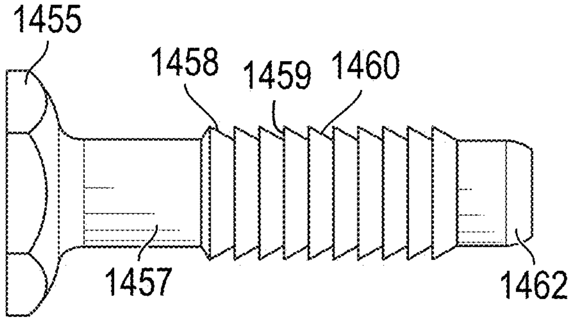

FIG. 119C is a side view of the ratchet fastener of FIG. 119A.

Figure 120A:
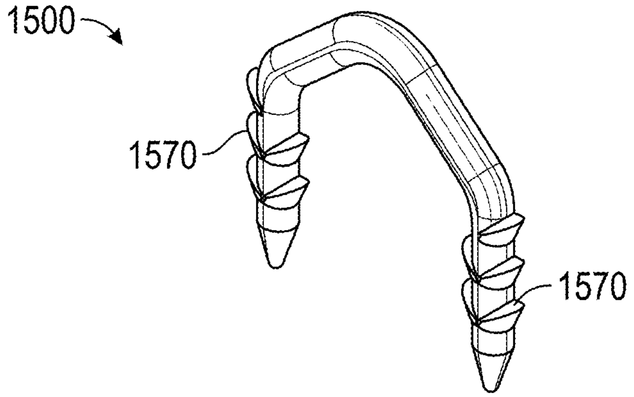

FIG. 120A is a perspective view of a fracture repair system in an undeformed configuration according to an embodiment of the present disclosure.

Figure 120B:
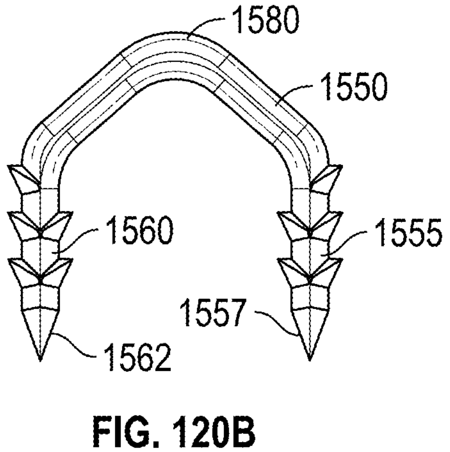

FIG. 120B is a front view of the fracture repair system of FIG. 120A in an undeformed configuration.

Figure 120C:
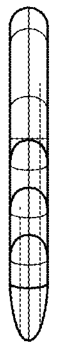

FIG. 120C is a side view of the fracture repair system of FIG. 120A in an undeformed configuration.

Figure 121:
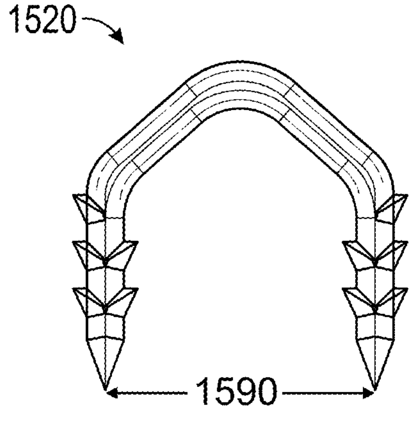

FIG. 121 is a front view of the fracture repair system of FIG. 120A in an undeformed configuration.

Figure 122:
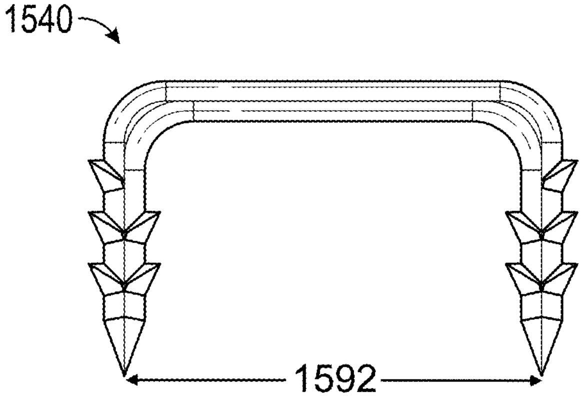

FIG. 122 is a front view of the fracture repair system of FIG. 120A in an expanded configuration according to an embodiment of the present disclosure.

Figure 123:
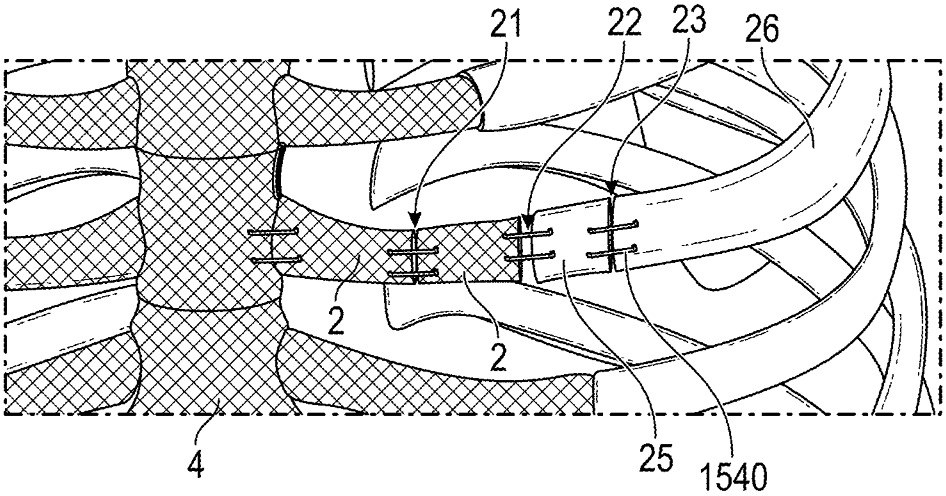

FIG. 123 is a front section view of an exemplary rib cage with the fracture repair system of FIG. 122 spanning exemplary fractures.

Figure 124:
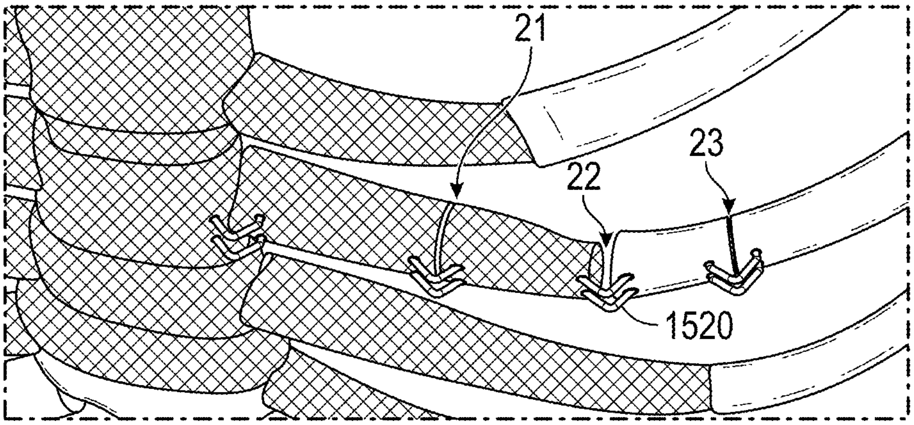

FIG. 124 is a front section view of an exemplary rib cage with the fracture repair system of FIG. 120A compressing exemplary fractures.

Figure 125:
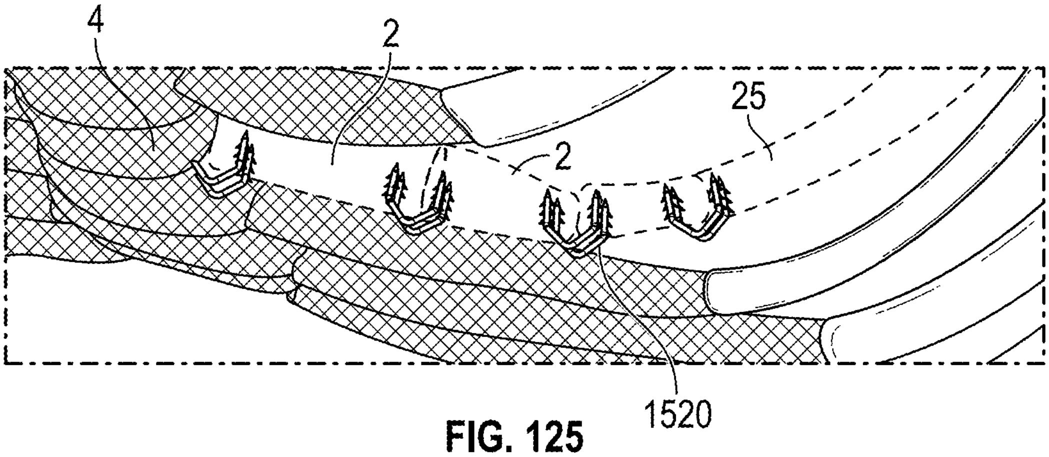

FIG. 125 is a front section view of an exemplary rib cage with the fracture repair system of FIG. 120A compressing exemplary fractures.

Figure 126A:
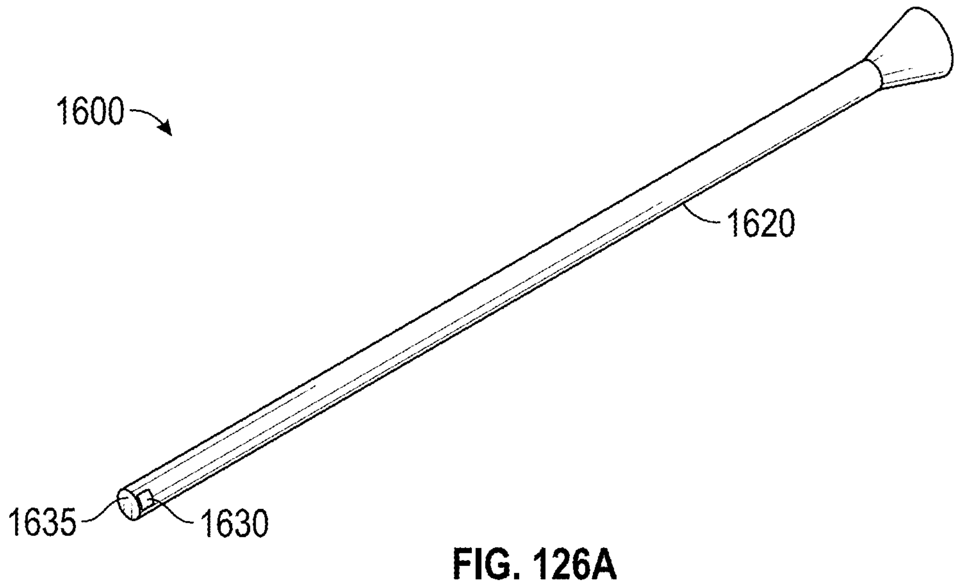

FIG. 126A is a perspective view of an application instrument of a fracture repair system according to an embodiment of the present disclosure.

Figure 126B:
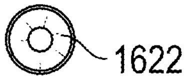

FIG. 126B is a side view of the application instrument of FIG. 126A.

Figure 126C:
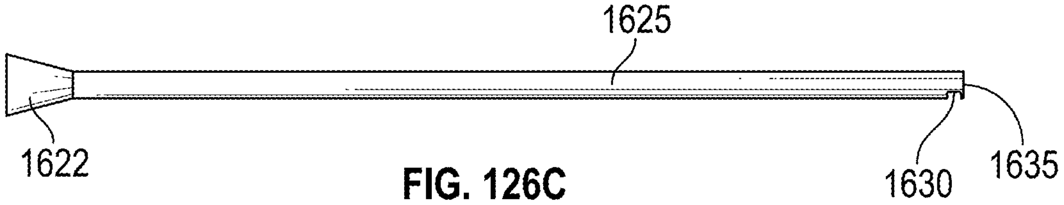

FIG. 126C is a front view of the application instrument of FIG. 126A.

Figure 127:
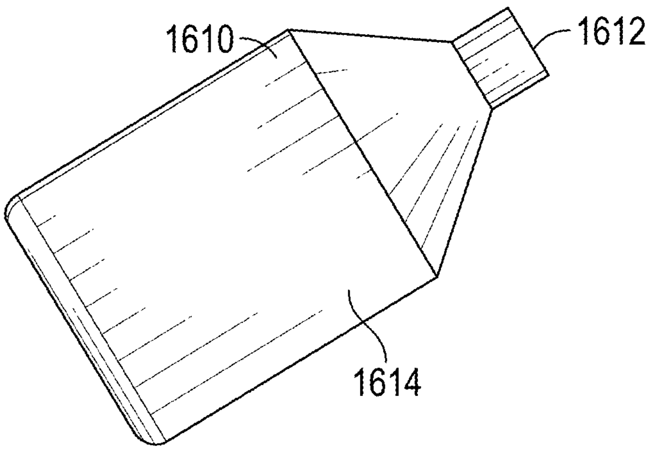

FIG. 127 is a balloon of a fracture repair system according to an embodiment of the present disclosure.

Figure 128:
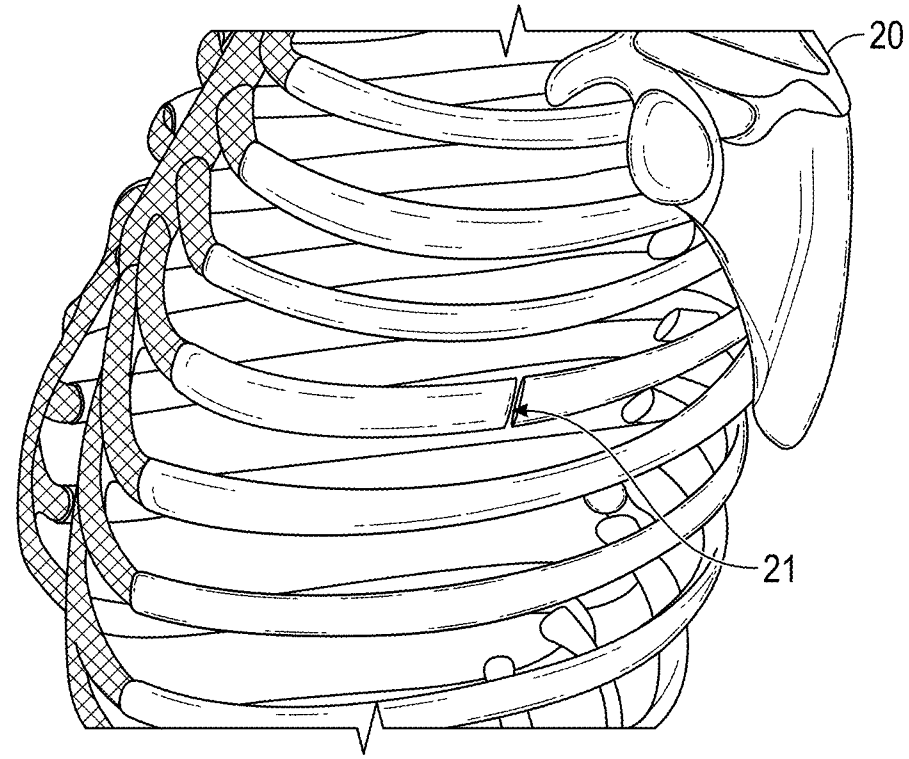

FIG. 128 is a partial perspective view of an exemplary rib cage with an exemplary bone fracture.

Figure 129:
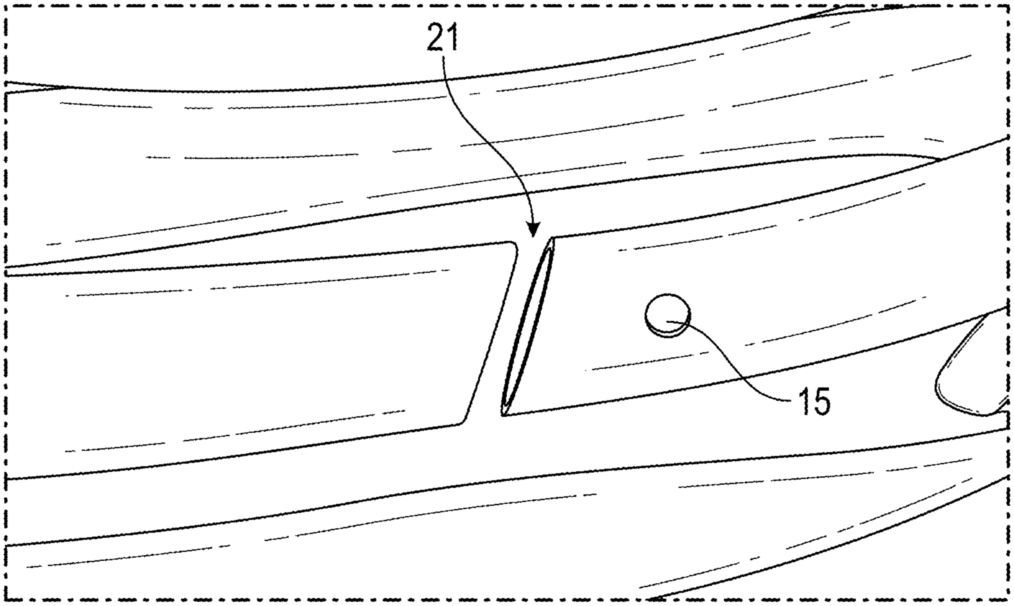

FIG. 129 is a partial perspective view of the exemplary rib cage of FIG. 128 illustrating a step in a method of deploying a fracture repair system according to an embodiment of the present disclosure.

Figure 130:
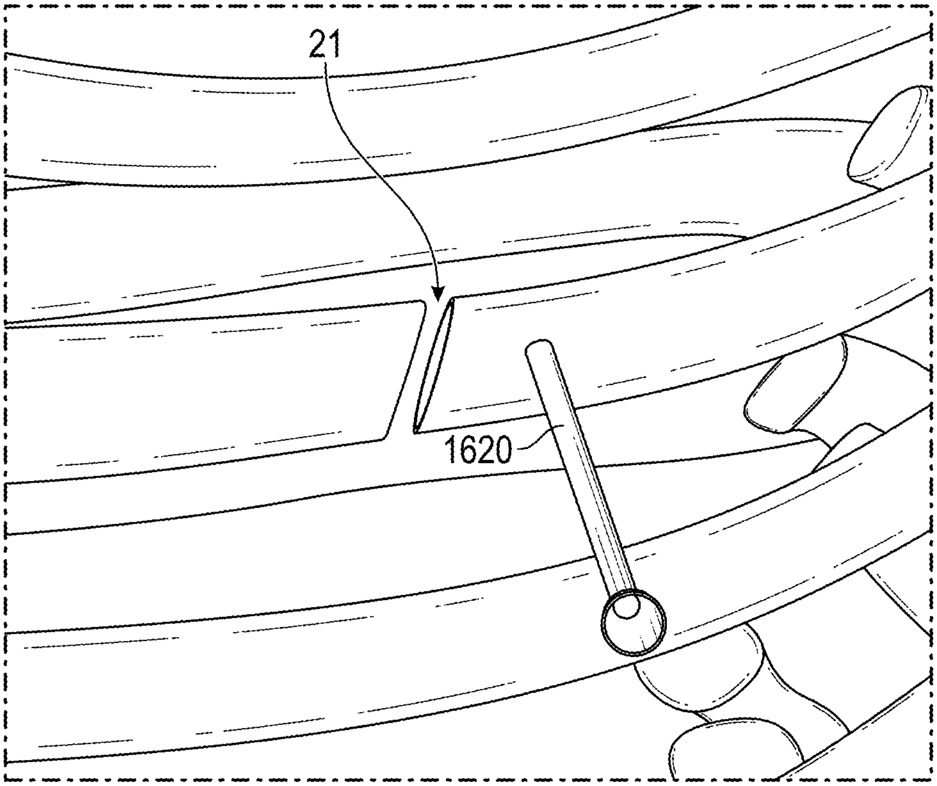

FIG. 130 is a partial perspective view of the exemplary rib cage of FIG. 128 illustrating a step in a method of deploying a fracture repair system according to an embodiment of the present disclosure.

Figure 131:
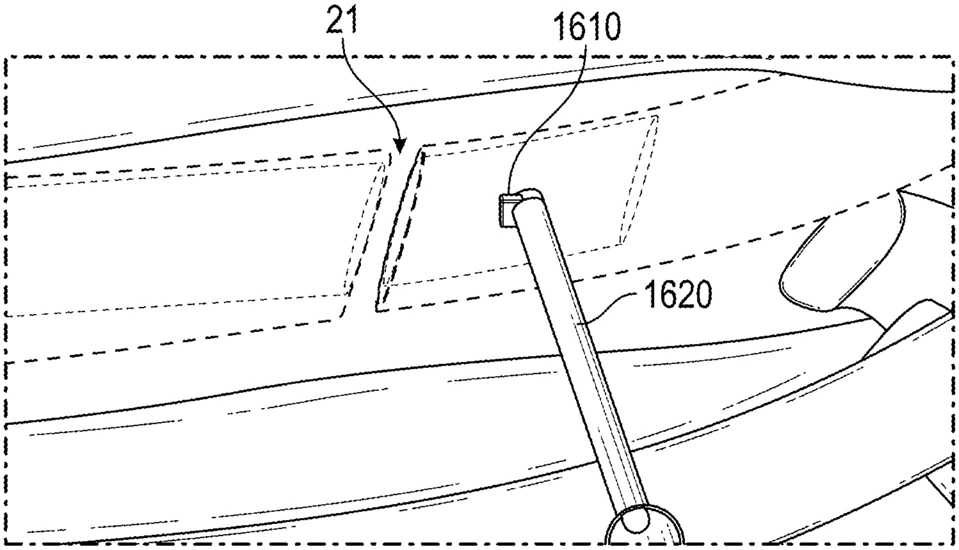

FIG. 131 is a partial perspective view of the exemplary rib cage of FIG. 128 illustrating a step in a method of deploying a fracture repair system according to an embodiment of the present disclosure.

Figure 132:
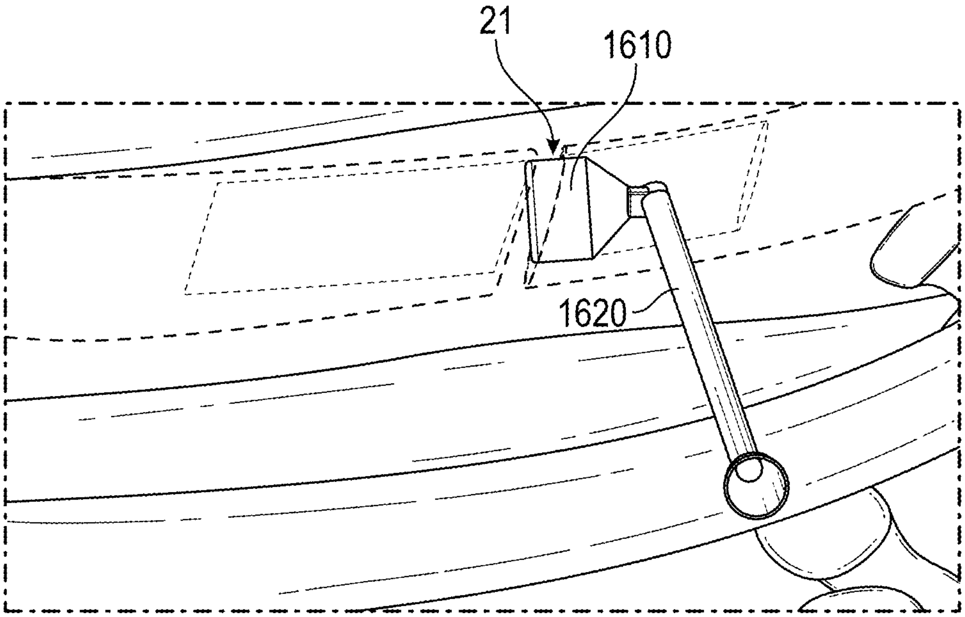

FIG. 132 is a partial perspective view of the exemplary rib cage of FIG. 128 illustrating a step in a method of deploying a fracture repair system according to an embodiment of the present disclosure.

Figure 133:
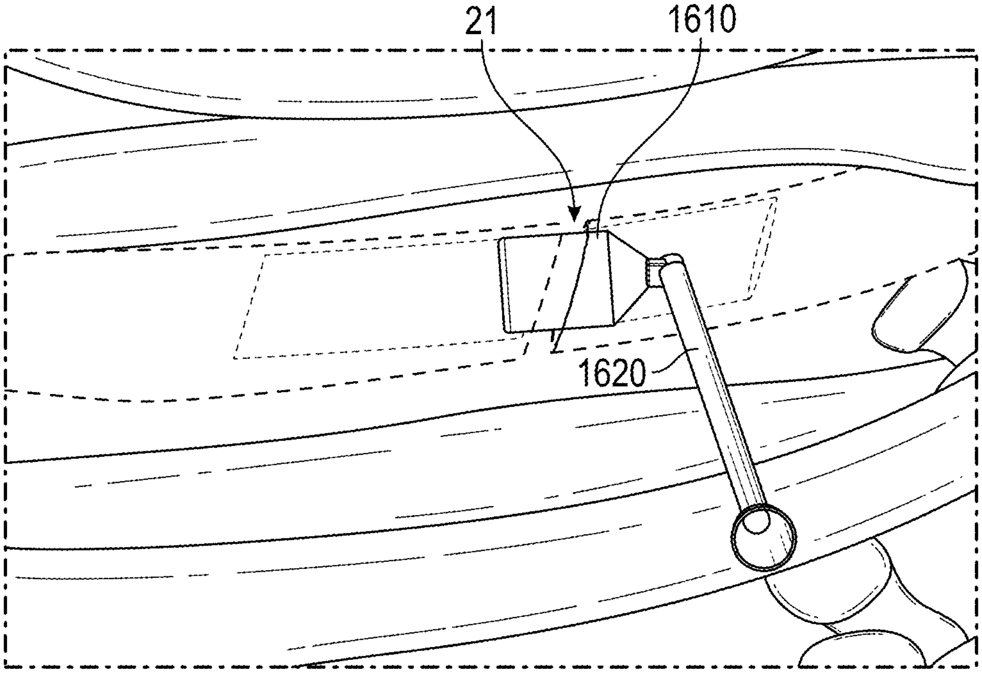

FIG. 133 is a partial perspective view of the exemplary rib cage of FIG. 128 illustrating a step in a method of deploying a fracture repair system according to an embodiment of the present disclosure.

Figure 134:
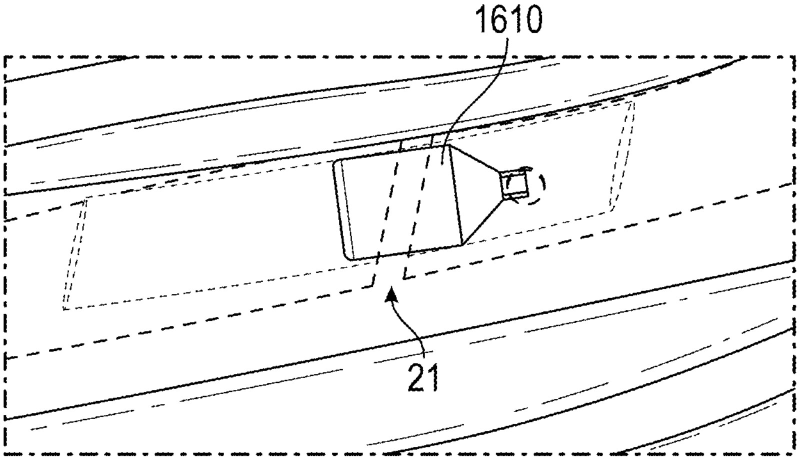

FIG. 134 is a partial perspective view of the exemplary rib cage of FIG. 128 illustrating a step in a method of deploying a fracture repair system according to an embodiment of the present disclosure.

Figure 135:
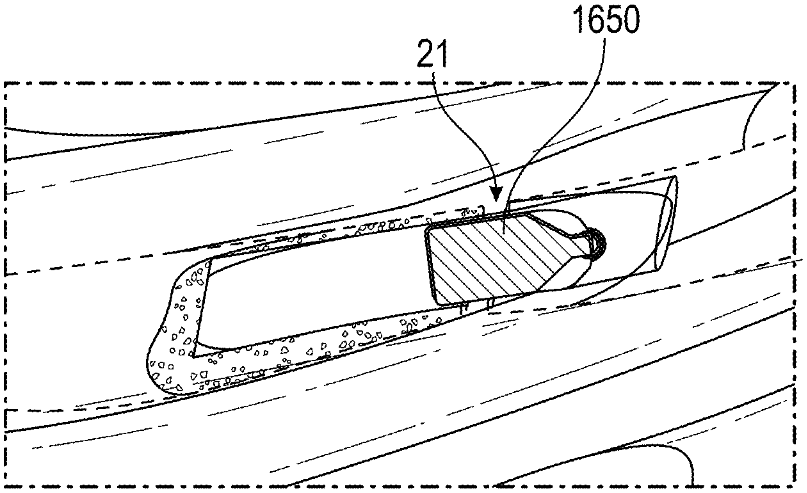

FIG. 135 is a partial perspective section view of the exemplary rib cage of FIG. 128 illustrating a step in a method of deploying a fracture repair system according to an embodiment of the present disclosure.

Figure 136:
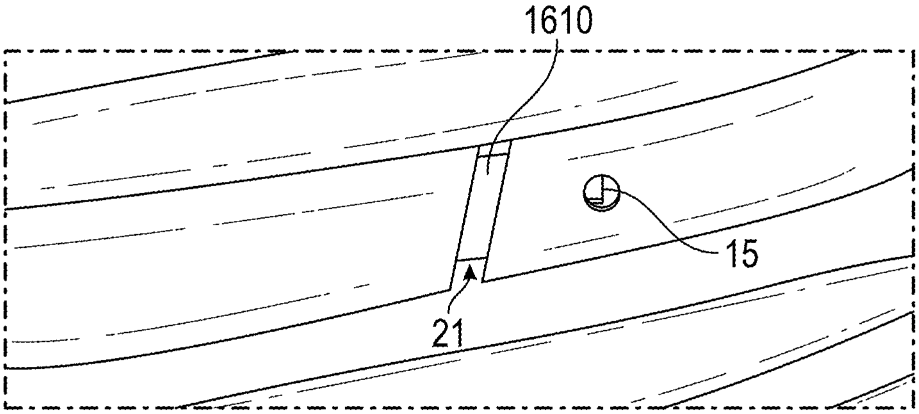

FIG. 136 is a partial perspective view of the exemplary rib cage of FIG. 128 illustrating a step in a method of deploying a fracture repair system according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word “exemplary” is used herein to mean “serving as an example, instance, or illustration.” Any embodiment described herein as “exemplary” is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

The present disclosure relates to fracture plating devices, systems, and methods. Those skilled in the art will recognize that the following description is merely illustrative of the principles of the technology, which may be applied in various ways to provide many alternative embodiments. The present disclosure illustrates devices for plating systems for one or more fractures of a rib for the purposes of illustrating the concepts of the present design. However, it will be understood that other variations and uses are contemplated including, but not limited to, fractures of metatarsals, fractures of phalanges, metacarpals, and carpals, fractures of a fibula, fractures of an ulna, and other bone fractures.

Figure 1:
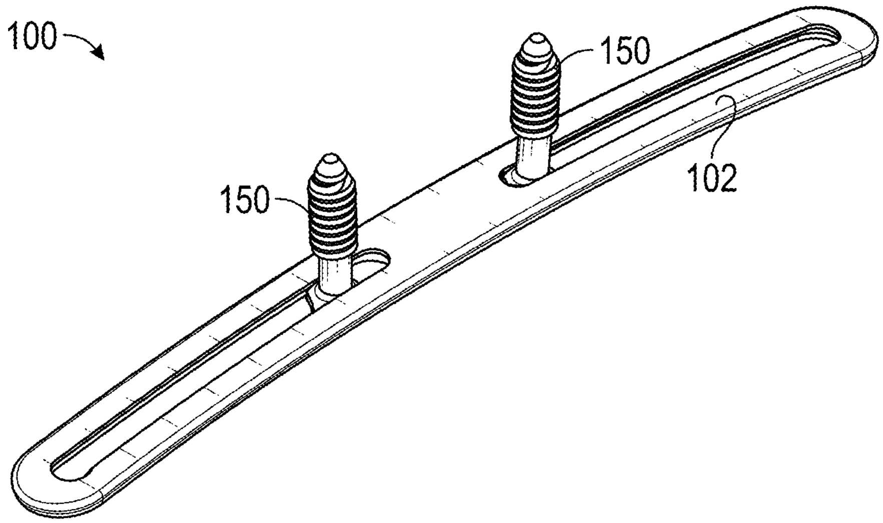
FIG. 1 is a perspective view of a fracture plating system according to an embodiment of the present disclosure.

FIG. 1 is a perspective view of a fracture plating system 100 according to an embodiment of the present disclosure. The fracture plating system 100 may be configured to stabilize bone fractures through intra-thoracic plating. The fracture plating system 100 may be configured to be secured to an interior surface of a bone, an exterior surface of a bone, or both an interior surface of a bone and an exterior surface of a bone. The fracture plating system 100 may beneficially require a smaller incision in the chest of a patient as compared to a plating system that is only configured to be secured to an exterior surface of a bone. The fracture plating system 100 may be configured to be introduced into an intra-thoracic cavity, or interior cavity, through one or more portals, commonly used for Video-assisted Thoracic Surgery (VATS) and/or a thoracoscopic procedure. Additionally, or alternatively, the fracture plating system 100 may be configured to be introduced into an intra-thoracic cavity, or interior body cavity, using a trans-intercostal approach. The trans-intercostal approach may include a surgical technique that involves making incisions between two adjacent ribs to access the thoracic cavity, or interior cavity.

The fracture plating system 100 may include a plate and a plurality of fasteners. The plates may be one of a set of differently sized implants. The fasteners may be of a set of differently sized implants. The fracture plating system 100 may be modular in that a specific sized plate may be chosen by a user based on patient anatomy and quantity and location of fractures. Additionally, a plurality of fasteners may be selected by a user based on patient anatomy and quantity and location of fractures. The selection of fasteners may include fasteners of the same or different lengths and/or diameters. After a selection is made, the plate and plurality of fasteners may be assembled by a user, for example, during a surgical procedure, to best address a specific patient's indications. The fracture plating system 100 may be configured to achieve the fixation of a fracture plate to a portion of bone using a single tether to pull the plate against the bone.

Figure 2B:
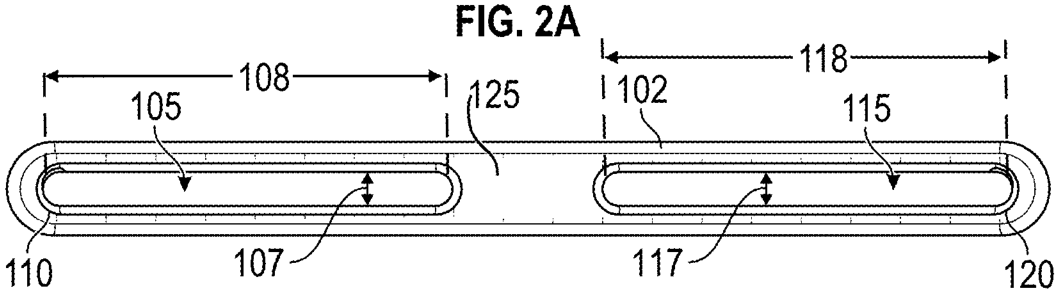
FIG. 2B is a bottom view of the plate of FIG. 2A.

The fracture plating system 100 may include a plate 102, an anti-rotation fastener 150 and/or a circular head fastener 180, a locking nut 30, and a washer 50. FIG. 2A is a front view of a plate 102 of the fracture plating system 100 according to an embodiment of the present disclosure. FIG. 2B is a bottom view of the plate 102. The plate 102 may be configured to stabilize and/or facilitate reduction of a fracture as a component of the fracture plating system 100. The plate 102 may include a plate length 103 and a plate radius 104. The plate length 103 may be configured to span one or more fractures.

The plate 102 may be configured such that the plate length 103 is within a range of lengths from 30 mm to 300 mm. The plate 102 may be one of a set of differently-sized implants, each having a different plate length 103. The plate radius 104 may generally match a contour of an interior surface of a rib. The plate 102 may further be one of a set of differently-sized implants, each having a different plate radius 104.

The plate 102 may further include a central portion 125 and a first slot 105 extending along a longitudinal axis of the plate 102 and having a first slot width 107, a first slot length 108, and a first threaded feature 110. The plate 102 may also include a second slot 115 extending along a longitudinal axis of the plate 102 and having a second slot width 117, a second slot length 118, and a second threaded feature 120. The central portion 125 may be generally in the center of the plate 102 and may separate the first slot 105 and the second slot 115.

The plate 102 may be fabricated from titanium alloy, titanium, stainless steel, cobalt-chrome, PEEK, PEAK, UHMWPE, a resorbable polymer, or any other biocompatible material with sufficient tensile strength.

The first slot width 107 and the second slot width 117 may each be configured to receive an anti-rotation fastener 150 and/or a circular head fastener 180. The first slot width 107 and the second slot width 117 may further be configured to allow translation of the anti-rotation fastener 150 and/or circular head fastener 180 along the length of the first slot and the second slot respectively.

Figure 3A:
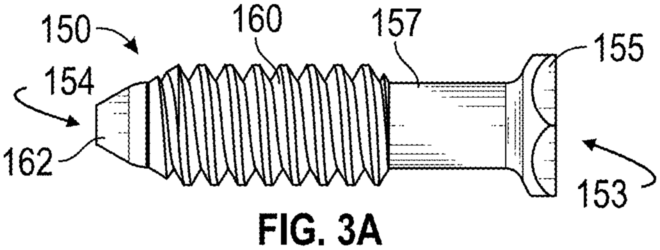
FIG. 3A is a front view of an anti-rotation fastener of the fracture plating system of FIG. 1 according to an embodiment of the present disclosure.
Figure 3B:
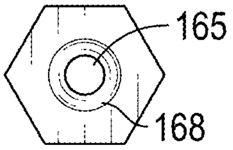
FIG. 3B is a side view of the anti-rotation fastener of FIG. 3A.

FIG. 3A is a front view of an anti-rotation fastener 150 of the fracture plating system 100 according to an embodiment of the present disclosure. FIG. 3B is a side view of the anti-rotation fastener 150. The anti-rotation fastener 150 may be configured to secure the plate 102 to a bone portion. The anti-rotation fastener 150 may also be configured to be captively received within the plate 102 while still being allow to translate along the length of the first slot 105 and/or the second slot 115. The anti-rotation fastener 150 may be configured so that, when a head portion 155 engages the first slot 105 and/or the second slot 115, the anti-rotation fastener 150 is prevented from rotating in relation to the plate 102.

The anti-rotation fastener 150 may include a shank portion 157, a threaded portion 160, a tip portion 162, a cannulation 165, and a rounded edge 168. The anti-rotation fastener 150 may further include a proximal end 153 including a head portion 155, and a distal end 154 opposite the proximal end 153. The head portion 155 may be configured to be received within the first slot 105 and/or the second slot 115. The head portion 155 may lack protruding features that are configured to engage with the plate 102. The threaded portion 160 may be larger than a width of the first slot 105 and/or the second slot 115 to prevent the anti-rotation fastener 150 from disengaging from the plate 102. The first threaded feature 110 and the second threaded feature 120 may each be configured to threadably engage the threaded portion 160 to allow the threaded portion 160 to pass through the first threaded feature 110 and the second threaded feature 120 respectively.

The shank portion 157 may be smaller than a width of the first slot 105 and/or the second slot 115 to allow the anti-rotation fastener 150 to translate along the length of the first slot 105 and/or the second slot 115 respectively. The tip portion 162 may be configured to ease insertion of the anti-rotation fastener 150 into a hole in a bone portion. The cannulation 165 may be configured to slidably receive a tether 60. The rounded edge 168 may reduce stress on the tether 60 when the tether 60 exerts a force on the anti-rotation fastener 150.

Figure 4A:
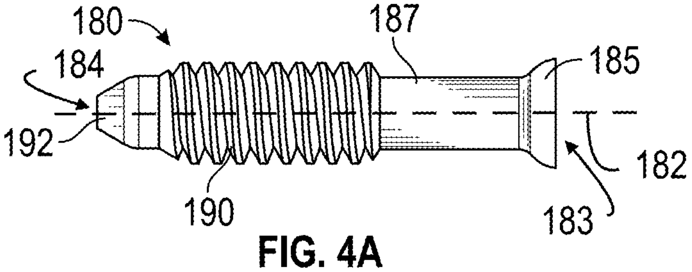
FIG. 4A is a front view of a circular head fastener of the fracture plating system of FIG. 1 according to an embodiment of the present disclosure.
Figure 4B:
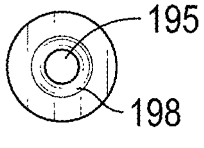
FIG. 4B is a side view of the circular head fastener of FIG. 4A.

FIG. 4A is a front view of a circular head fastener 180 of the fracture plating system 100 according to an embodiment of the present disclosure. FIG. 4B is a side view of the circular head fastener 180. The circular head fastener 180 may be configured to secure the plate 102 to a bone portion. The circular head fastener 180 may also be configured to be captively received within the plate 102 while still being allow to translate along the length of the first slot 105 and/or the second slot 115. The circular head fastener 180 may be configured so that, when a head portion 185 engages the first slot 105 and/or the second slot 115, the circular head fastener 180 is not prevented from rotating in relation to the plate 102.

The circular head fastener 180 may include a shank portion 187, a threaded portion 190, a tip portion 192, a cannulation 195, and a rounded edge 198. The circular head fastener 180 may include a proximal end 183 including a head portion 185, and a distal end 184 opposite the proximal end 183. The head portion 185 may be configured to be received within the first slot 105 and/or the second slot 115. The threaded portion 190 may be larger than a width of the first slot 105 and/or the second slot 115 to prevent the circular head fastener 180 from disengaging from the plate 102.

The shank portion 187 may be smaller than a width of the first slot 105 and/or the second slot 115 to allow the circular head fastener 180 to translate along the length of the first slot 105 and/or the second slot 115 respectively. The tip portion 192 may be configured to ease insertion of the circular head fastener 180 into a hole in a bone portion. The cannulation 195 may be configured to slidably receive a tether 60. The rounded edge 198 may reduce stress on the tether 60 when the tether 60 exerts a force on the circular head fastener 180.

The anti-rotation fastener 150 and/or the circular head fastener 180 may be configured within a range of lengths from 5 mm to 30 mm and within a range of diameters from 3 mm to 8 mm. The anti-rotation fastener 150 and/or the circular head fastener 180 may be one of a set of differently-sized implants, each having a different length and/or diameter.

The fracture plating system 100 may further include two or more locking nuts 30 and a two or more washers 50. The locking nut 30 may be configured to threadably engage the anti-rotation fastener 150 and/or the circular head fastener 180 to secure the plate 102 to a portion of a rib. The locking nut 30 may be configured to receive the anti-rotation fastener 150 and/or the circular head fastener 180 and to cooperate with the anti-rotation fastener 150 and/or the circular head fastener 180 to secure the plate 102 to the bone. The washer 50 may be configured to be place between the locking nut 30 and a surface of a portion of a rib. The washer 50 may reduce damage to the surface of the portion of the rib due to rotation of the locking nut 30. Additionally, or alternatively, the washer 50 may provide a greater contact area with the surface of the portion of the rib resulting in greater securing of the plate 102 with the portion of the rib.

Figure 5A:
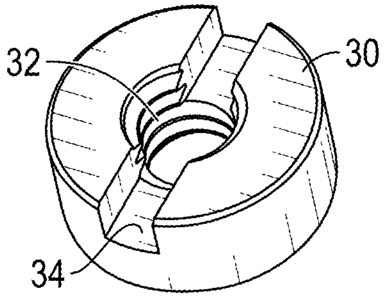
FIG. 5A is a perspective view of a locking nut of the fracture plating system of FIG. 1 according to an embodiment of the present disclosure.
Figure 5B:
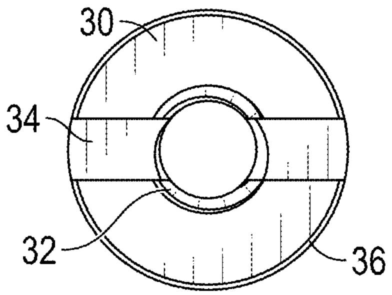
FIG. 5B is a top view of the locking nut of FIG. 5A.
Figure 5C:
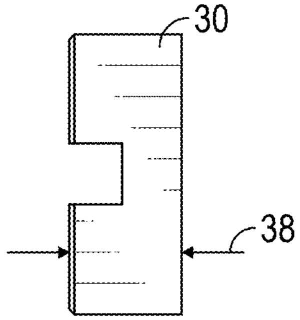
FIG. 5C is a side view of the locking nut of FIG. 5A.

FIG. 5A is a perspective view of a locking nut 30 of the fracture plating system 100 according to an embodiment of the present disclosure. FIG. 5B is a top view of the locking nut 30 and FIG. 5C is a side view of the locking nut 30. The locking nut 30 may include a threaded portion 32, a slot 34, an outside diameter 36, and a thickness 38. The threaded portion 32 may be configured to threadably engage the threaded portion 160 of the anti-rotation fastener 150 and/or the threaded portion 190 of the circular head fastener 180. The slot 34 may allow engagement of a driver (not shown) to threadably engage the locking nut 30 with the anti-rotation fastener 150 and/or the circular head fastener 180.

The outside diameter 36 may be larger than a hole sized to receive the anti-rotation fastener 150 and/or the circular head fastener 180. The thickness 38 may be configured so that there is sufficient thread engagement to secure the plate 102 to the portion of the bone.

Figure 6A:
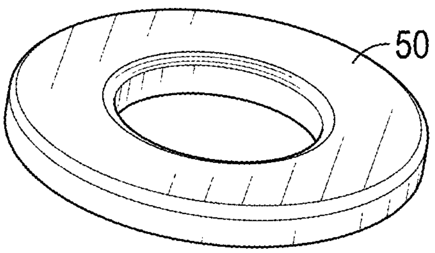
FIG. 6A is a perspective view of a washer of the fracture plating system of FIG. 1 according to an embodiment of the present disclosure.
Figure 6B:
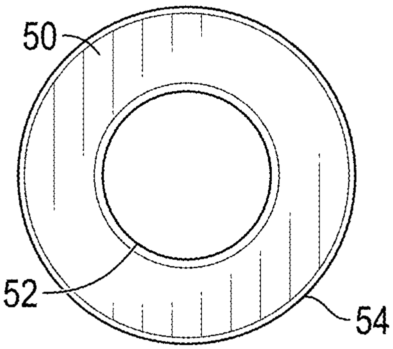
FIG. 6B is a top view of the washer of FIG. 6A.
Figure 6C:
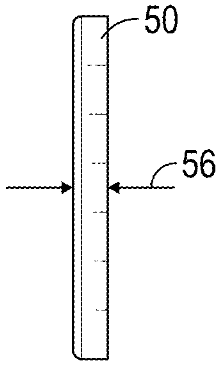
FIG. 6C is a side view of the washer of FIG. 6A.

FIG. 6A is a perspective view of a washer 50 of the fracture plating system 100 according to an embodiment of the present disclosure. FIG. 6B is a top view of the washer 50 and FIG. 6C is a side view of the washer 50. The washer 50 may include an inside diameter 52, an outside diameter 54, and a thickness 56. The inside diameter 52 may be configured to slidably receive the threaded portion 160 of the anti-rotation fastener 150 and/or the threaded portion 190 of the circular head fastener 180. The outside diameter 54 may be configured to be greater than or equal to the outside diameter 36 of the locking nut 30.

The thickness 56 may be configured so that when the washer 50 is placed between the surface of the portion of the rib and the locking nut 30, a sufficient length of the threaded portion 160 of the anti-rotation fastener 150 and/or the threaded portion 190 of the circular head fastener 180 is exposed to allow sufficient thread engagement between the locking nut 30 and the anti-rotation fastener 150 and/or the circular head fastener 180 to secure the plate 102 to the portion of the rib.

Figure 7:
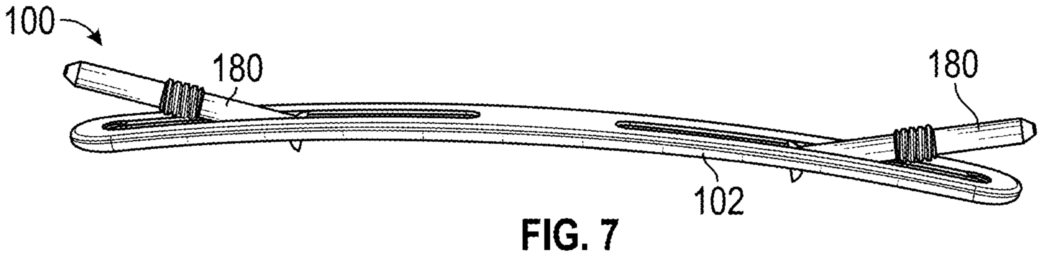
FIG. 7 is a perspective view of the fracture plating system of FIG. 1 in a lower profile configuration.

FIG. 7 is a perspective view of the fracture plating system 100 in a lower profile configuration. The fracture plating system 100 may advantageously be configured so that, when the anti-rotation fastener 150 and/or the circular head fastener 180 are captive received within the first slot 105 and/or the second slot 115, the anti-rotation fastener 150 and/or the circular head fastener 180 may be flattened against the plate 102 to make the construct lower profile and easier to insert into a patient.

Figure 8:
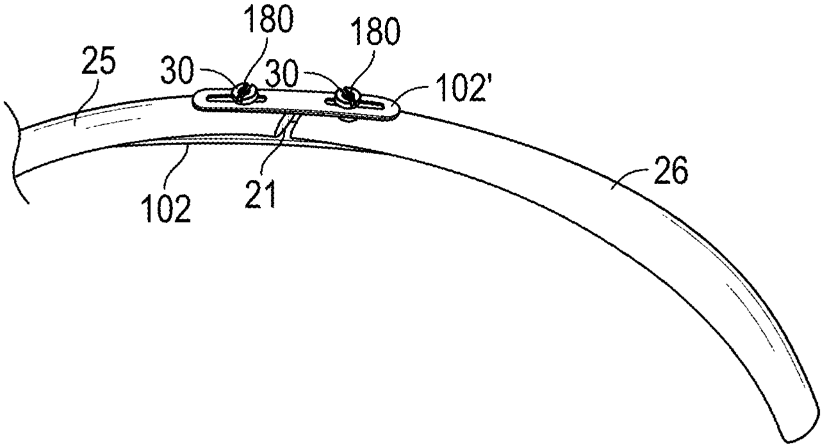
FIG. 8 is a perspective view of the fracture plating system of FIG. 1 spanning an exemplary bone fracture.

FIG. 8 is a perspective view of the fracture plating system of 100 spanning an exemplary bone first fracture 21. The fracture plating system 100 may include a second plate 102', securable to an exterior surface of a rib. The same fasteners may engage both a first plate 102 and a second plate 102'.

Figure 9:
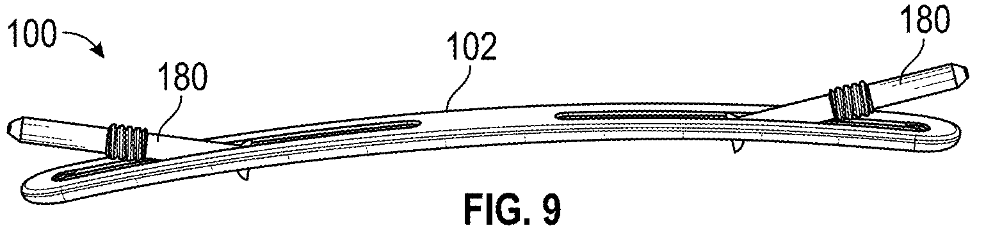
FIG. 9 is a perspective view of the fracture plating system of FIG. 1 in a lower profile configuration.
Figure 10A:
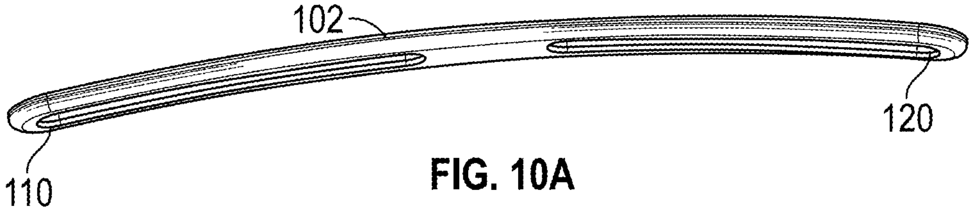
FIG. 10A is a perspective view of the plate of the fracture plating system of FIG. 1 according to an embodiment of the present disclosure.
Figure 10B:
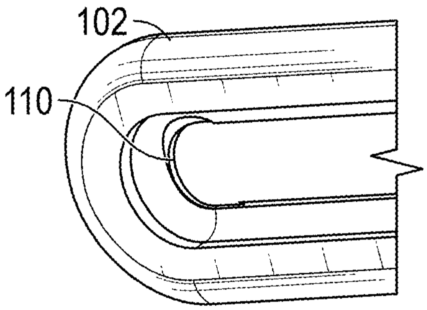
FIG. 10B is a top perspective partial view of the plate of FIG. 10A.

FIG. 9 is a perspective view of the fracture plating system 100 in a lower profile configuration. FIG. 10A is a perspective view of the plate 102 of the fracture plating system of 100 according to an embodiment of the present disclosure. FIG. 10B is a top perspective partial view of the plate 102. The first threaded feature 110 and the second threaded feature 120 may each be configured to threadably engage the threaded portion 190 to allow the threaded portion 190 to pass through the first threaded feature 110 and the second threaded feature 120 respectively. The circular head fastener 180 may be further configured so that, with the circular head fastener 180 captively received in the first slot 105 and/or the second slot 115, the circular head fastener 180 may be moveable relative to the plate 102 along a longitudinal axis 182 of the circular head fastener 180.

Figure 11:
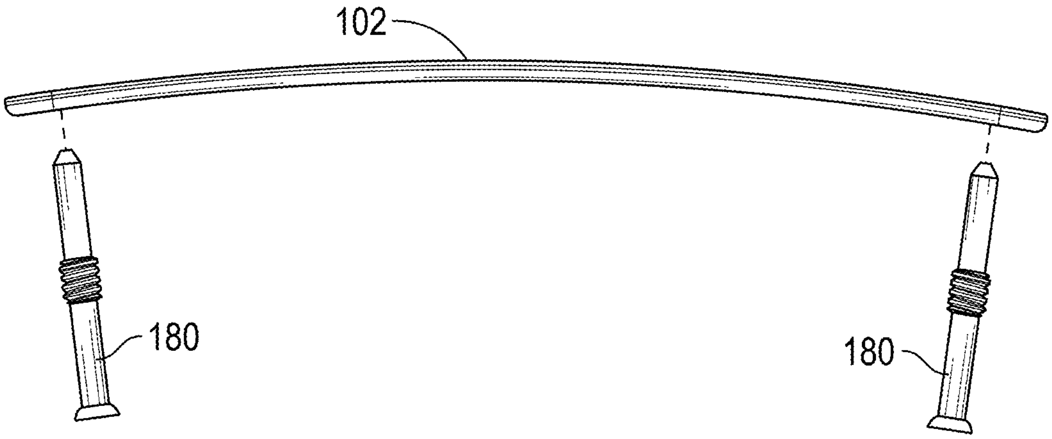
FIG. 11 is a front view of the fracture plating system of FIG. 1 in a first pre-assembled configuration.

FIG. 11 is a front view of the fracture plating system 100 in a first pre-assembled configuration. The anti-rotation fastener 150 and/or the circular head fastener 180 may be aligned with the first threaded feature 110 and/or the second threaded feature 120 of the plate 102.

Figure 12:
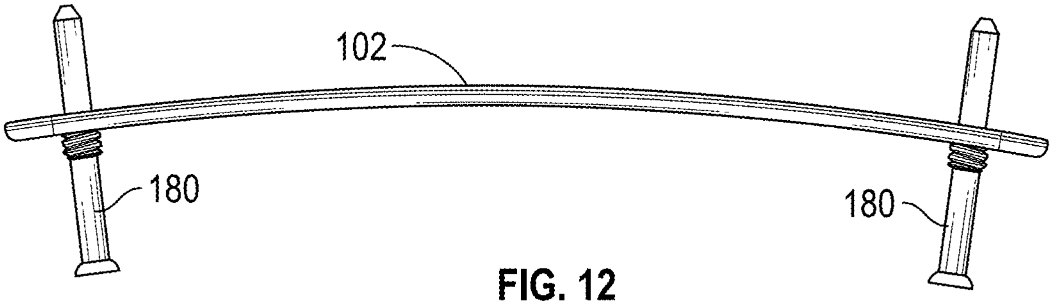
FIG. 12 is a front view of the fracture plating system of FIG. 1 in a second pre-assembled configuration.

FIG. 12 is a front view of the fracture plating system of 100 in a second pre-assembled configuration. The tip portion 162 of the anti-rotation fastener 150 and/or the tip portion 192 of the circular head fastener 180 may be slidably received within the first threaded feature 110 and/or the second threaded feature 120 of the plate 102.

Figure 13:
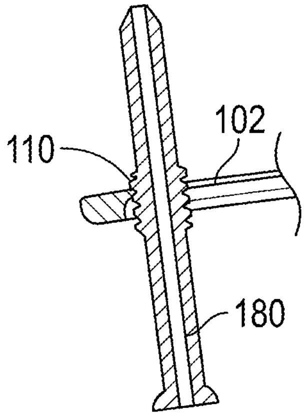
FIG. 13 is a front partial section view of the fracture plating system of FIG. 12.

FIG. 13 is a front partial section view of the fracture plating system 100. The threaded portion 160 of the anti-rotation fastener 150 and/or the threaded portion 190 of the circular head fastener 180 may threadably engage the first threaded feature 110 and/or the second threaded feature 120 of the plate 102.

Figure 14:
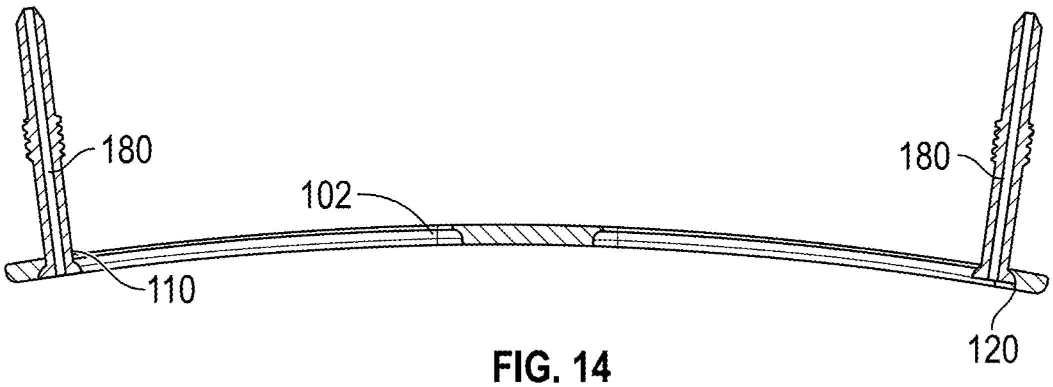
FIG. 14 is a front section view of the fracture plating system of FIG. 12 in a third pre-assembled configuration.

FIG. 14 is a front section view of the fracture plating system 100 in a third pre-assembled configuration. The head portion 155 of the anti-rotation fastener and/or the head portion 185 of the circular head fastener 180 may be configured to not pass through the first threaded feature 110 and/or the second threaded feature 120 of the plate 102 thereby capturing the anti-rotation fastener 150 and/or the circular head fastener 180 within the first slot 105 and/or the second slot 115 of the plate 102.

Figure 15:
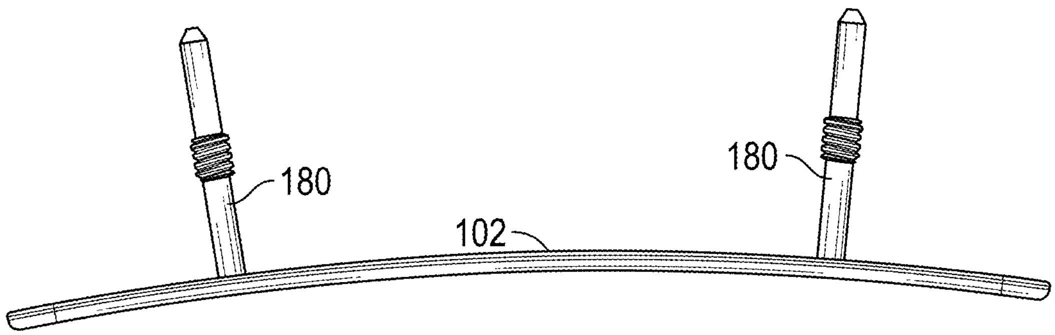
FIG. 15 is a front view of the fracture plating system of FIG. 1 in an assembled configuration.
Figure 16:
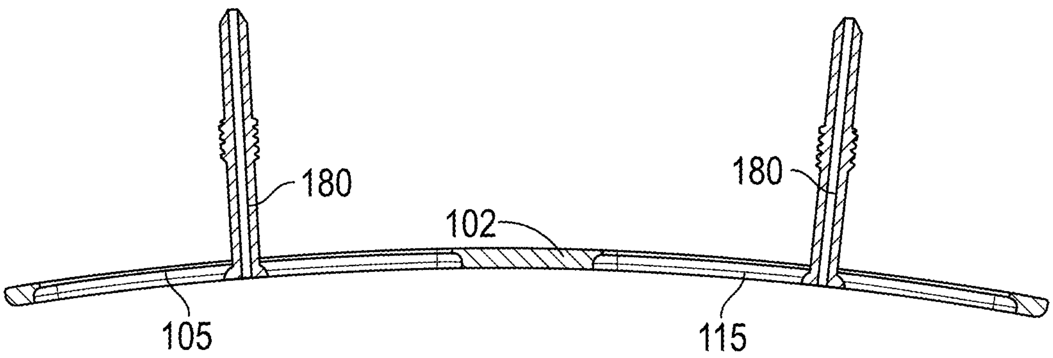
FIG. 16 is a front section view of the fracture plating system of FIG. 15.

FIG. 15 is a front view of the fracture plating system of 100 in an assembled configuration. FIG. 16 is a front section view of the fracture plating system 100 in an assembled configuration. In the assembled configuration, the fracture plating system 100 may include a plate assembly including a plate 102, a first fastener, and a second fastener, wherein each of the first fastener and the second fastener may be chosen from the anti-rotation fastener and/or the head portion 185 of the circular head fastener 180. The shank portion 157 of the anti-rotation fastener 150 and/or the shank portion 187 of the circular head fastener 180 may be configured to allow the anti-rotation fastener 150 and/or the circular head fastener 180 to translate along the first slot 105 and/or the second slot 115 of the plate 102.

Figure 17:
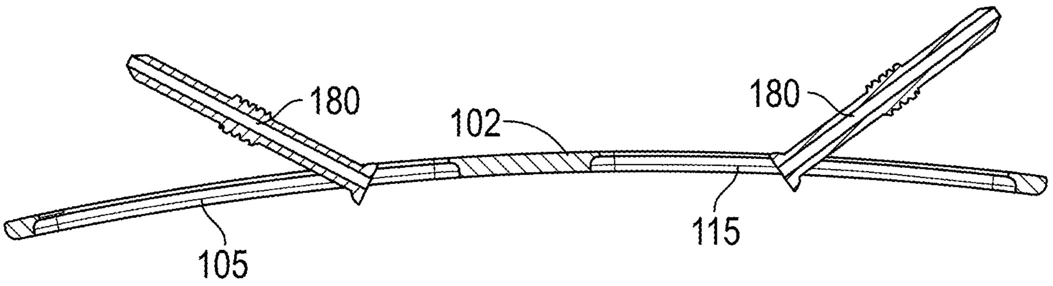
FIG. 17 is a front section view of the fracture plating system of FIG. 1 in a lower profile configuration.

FIG. 17 is a front section view of the fracture plating system 100 in a lower profile configuration. The plate 102, and the anti-rotation fastener 150 and/or the circular head fastener 180 may be configured so that the anti-rotation fastener 150 and/or the circular head fastener 180 may be flattened against the plate 102 to make the construct lower profile and easier to insert into an intra-thoracic cavity of a patient. The anti-rotation fastener 150 and/or the circular head fastener 180 may be configured to reside captive within the first slot 105 and/or the second slot 115 independently of engagement of any protruding feature of the head portion 155 and/or the head portion 185 with the plate 102.

Figure 18:
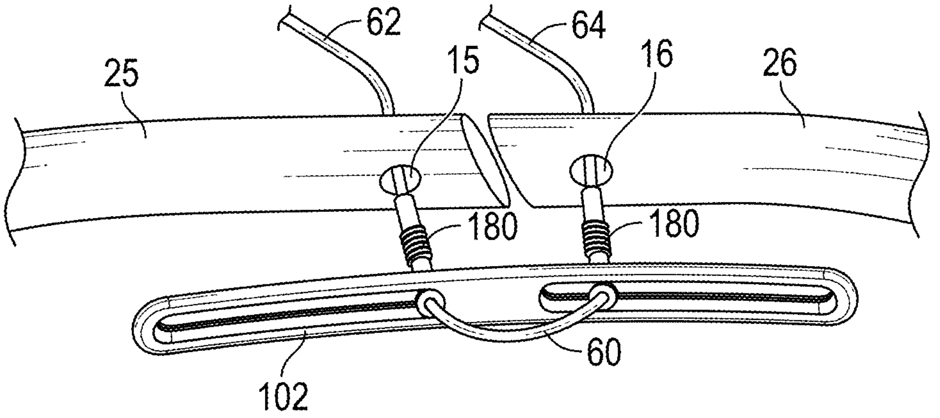
FIG. 18 is a perspective view of the fracture plating system of FIG. 1 in a partially deployed configuration spanning an exemplary bone fracture.
Figure 19:
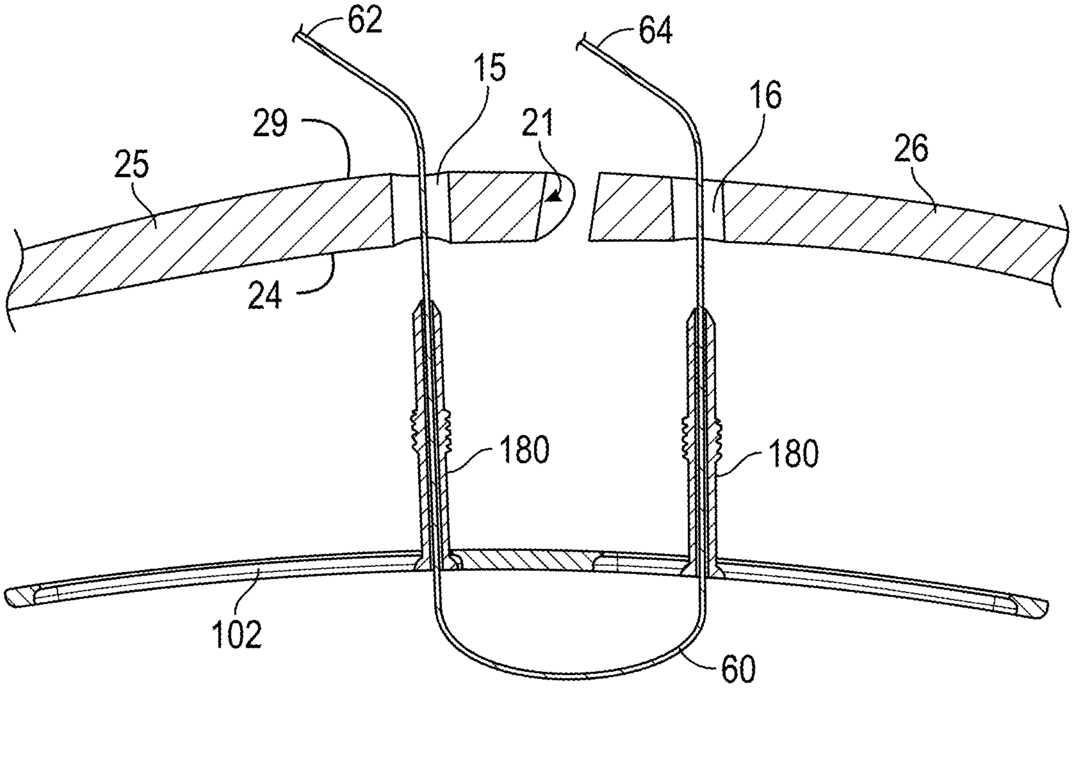
FIG. 19 is a front section view of the fracture plating system of FIG. 18 in a partially deployed configuration spanning an exemplary bone fracture.

FIG. 18 is a perspective view of the fracture plating system 100 in a partially deployed configuration spanning an exemplary bone first fracture 21. FIG. 19 is a front section view of the fracture plating system 100 in a partially deployed configuration spanning an exemplary bone first fracture 21. The bone may include an interior surface 24 facing toward an interior body cavity of a patient, and an exterior surface 29 facing away from the interior body cavity of the patient.

The cannulation 165 of the anti-rotation fastener 150 and/or the cannulation 195 of the circular head fastener 180 may be configured to slidably receive a tether 60. A tether 60 may be configured to apply a force directly to one or more fasteners to guide the one or more fasteners to the interior surface of the bone and through a hole in the interior surface of the bone.

A circular head fastener 180 length may be chosen from a range of fastener lengths such that the threaded portion 190 exposed beyond the exterior surface of the portion of bone may be greater than or equal to the thickness 38 of the locking nut 30. Alternatively, a circular head fastener 180 length may be chosen from a range of fastener lengths such that the threaded portion 190 exposed beyond the exterior surface of the portion of bone may be greater than or equal to the thickness 38 of the locking nut 30 plus the thickness 56 of the washer 50.

The tether 60 may be configured to guide the anti-rotation fastener 150 and/or the circular head fastener 180 through a first hole 15 and a second hole 16 from an interior side of a portion of a bone to an exterior side of a portion of a bone. The first hole 15 and the second hole 16 may be located on opposite sides of a first fracture 21. The distance between the first hole 15 and the second hole 16 may be greater than the central portion 125 of the plate 102.

Figure 20:
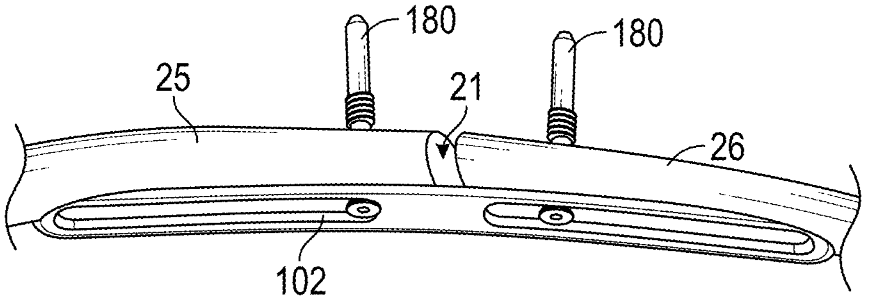
FIG. 20 is a perspective view of the fracture plating system of FIG. 18 in a partially deployed configuration spanning an exemplary bone fracture.
Figure 21:
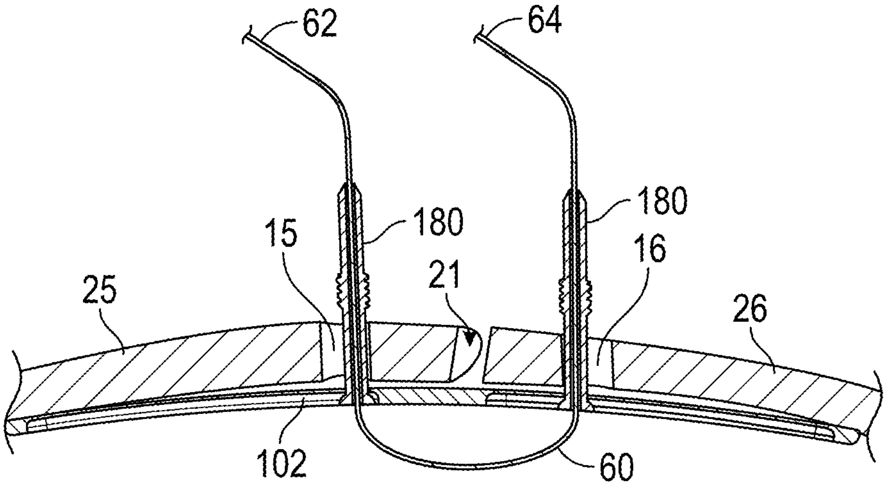
FIG. 21 is a front section view of the fracture plating system of FIG. 20 in a partially deployed configuration spanning an exemplary bone fracture.

FIG. 20 is a perspective view of the fracture plating system 100 in a partially deployed configuration spanning an exemplary bone first fracture 21. FIG. 21 is a front section view of the fracture plating system 100 in a partially deployed configuration spanning an exemplary bone first fracture 21. The tether 60 may be configured to pull the plate 102 against the interior side of a portion of a bone. The tether 60 may further be utilized to hold the plate 102 and the anti-rotation fastener 150 and/or the circular head fastener 180 in position so that the washer 50 and/or the locking nut 30 may be secured to the anti-rotation fastener 150 and/or the circular head fastener 180 to secure the fracture plating system 100 in place.

The fracture plating system 100 and the tether 60 may be configured so that a single tether 60 may be used to guide two fasteners through two holes in a portion of bone. The fracture plating system 100 and the tether 60 may further be configured so that a single tether 60 may be used to pull the plate 102 against an interior surface of a fractured rib.

Figure 22:
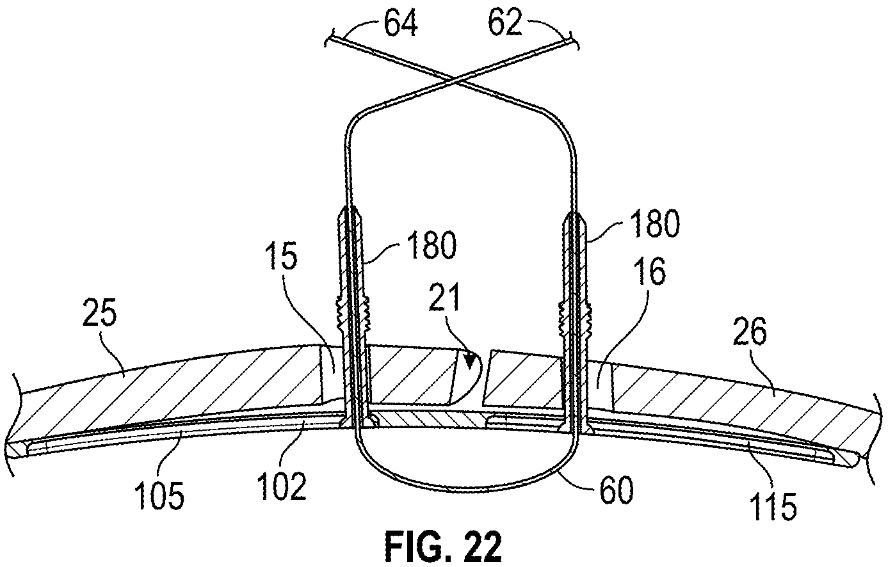
FIG. 22 is a front section view of the fracture plating system of FIG. 20 in a partially deployed configuration spanning an exemplary bone fracture.

FIG. 22 is a front section view of the fracture plating system 100 in a partially deployed configuration spanning an exemplary first fracture 21. The tether 60 may include a first tether end 62 and a second tether end 64. The first tether end 62 may be configured to be advanced through the cannulation 195 of a first circular head fastener 180 and the second tether end 64 may be configured to be advanced through the cannulation 195 of a second circular head fastener 180.

Figure 23:
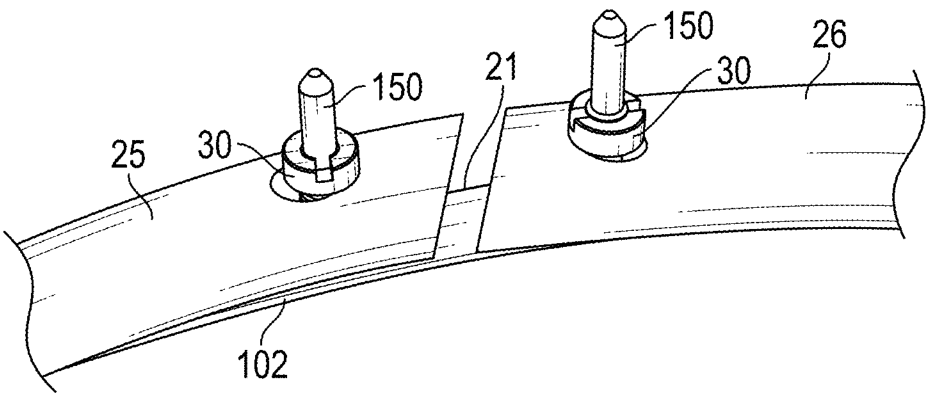
FIG. 23 is a perspective view of the fracture plating system of FIG. 20 in a partially deployed configuration spanning an exemplary bone fracture.

FIG. 23 is a perspective view of the fracture plating system 100 in a partially deployed configuration spanning an exemplary first fracture 21. The first tether end 62 may be pulled in the direction of the second circular head fastener 180 and the second tether end 64 may be pulled in the direction of the first circular head fastener, thereby applying compression to the first fracture 21 to facilitate reduction of the first fracture 21 by urging the first fastener and the second fastener towards each other. A locking nut 30 may be secured to each of the first and second circular head fastener 180 while compression is being applied to the fracture to secure the fracture plating system 100 in place.

Figure 24:
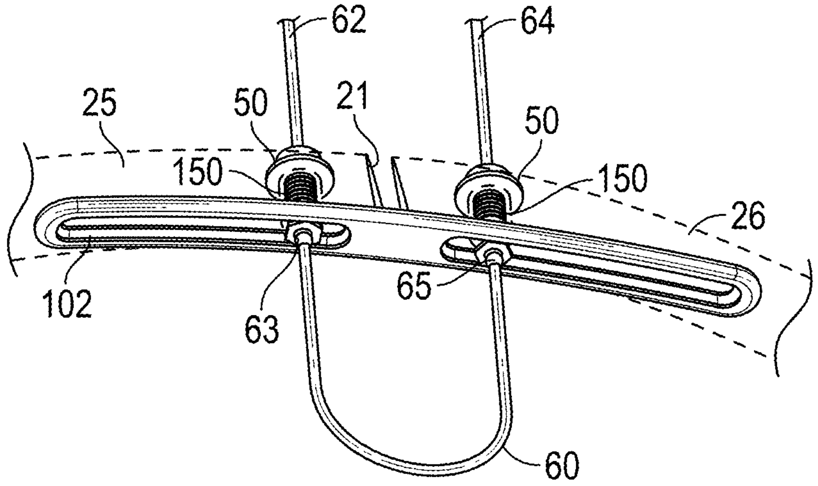
FIG. 24 is a perspective view of the fracture plating system of FIG. 1 in a partially deployed configuration spanning an exemplary bone fracture.
Figure 25:
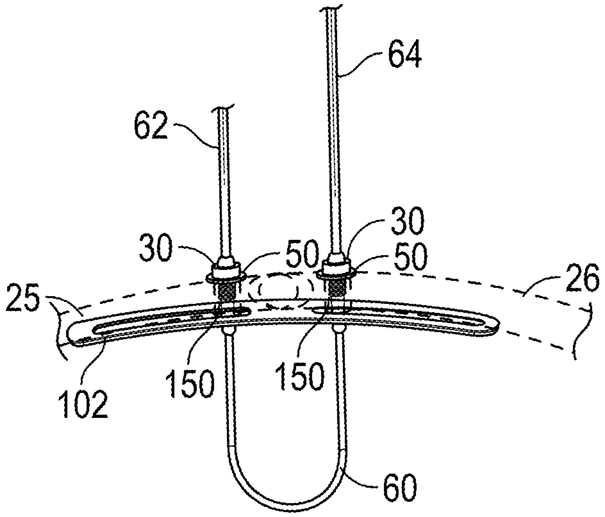
FIG. 25 is a front view of the fracture plating system of FIG. 24 in a partially deployed configuration spanning an exemplary bone fracture.

FIG. 24 is a perspective view of the fracture plating system 100 in a partially deployed configuration spanning an exemplary bone first fracture 21. FIG. 25 is a front view of the fracture plating system 100 in a partially deployed configuration spanning an exemplary bone first fracture 21. The tether 60 may include a first bead 63 and a second bead 65. The first bead 63 and the second bead 65 may be configured to engage the head portion 155 of the anti-rotation fastener 150 and/or the head portion 185 of the circular head fastener 180. The first bead 63 and the second bead 65 may be configured as a solid spherical section of larger diameter.

Additionally, the first bead 63 and the second bead 65 may be larger than the cannulation 165 of the anti-rotation fastener 150 and/or the cannulation 195 of the circular head fastener 180. The first bead 63 and the second bead 65 may not be received within the cannulation 165 of the anti-rotation fastener 150 and/or the cannulation 195 of the circular head fastener 180.

The first bead 63, the second bead 65, and the anti-rotation fastener and/or the circular head fastener 180 may be configured so that, when the first bead 63 engages a first fastener, a tension force applied to the first tether end 62 is translated as a compression force applied to the first fastener. Similarly, when the second bead 65 engages a second fastener, a tension force applied to the second tether end 64 is translated as a compression force applied to the second fastener.

Figure 26:
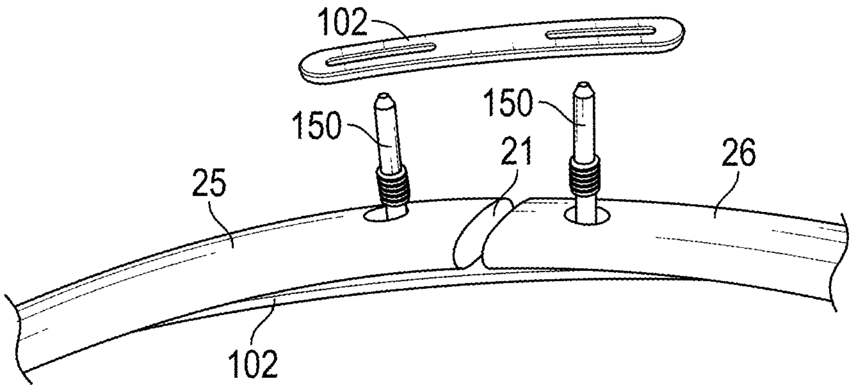
FIG. 26 is a perspective view of the fracture plating system of FIG. 1 in a partially deployed configuration spanning an exemplary bone fracture.

FIG. 26 is a perspective view of the fracture plating system 100 in a partially deployed configuration spanning an exemplary bone first fracture 21. In an embodiment, the fracture plating system 100 may include a second plate 102'. The second plate 102' may be configured as an outer buttress plate. The second plate 102' may be placed on an exterior surface of bone.

Figure 27:
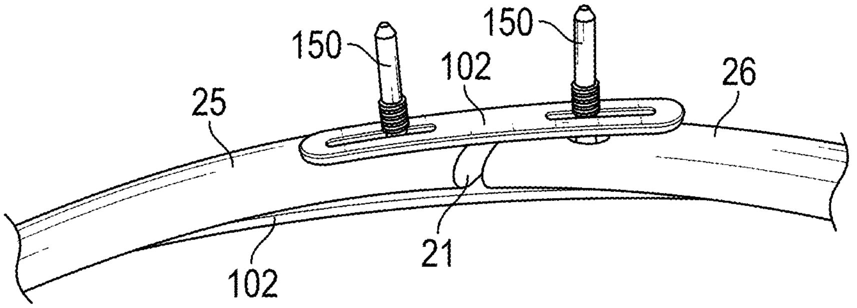
FIG. 27 is a perspective view of the fracture plating system of FIG. 26 in a partially deployed configuration spanning an exemplary bone fracture.

FIG. 27 is a perspective view of the fracture plating system 100 in a partially deployed configuration spanning an exemplary bone first fracture 21. The second plate 102' may span a first fracture 21 and may be secured to a portion of bone using the same fasteners that are used to secure the plate 102 to the interior surface of a bone.

Figure 28:
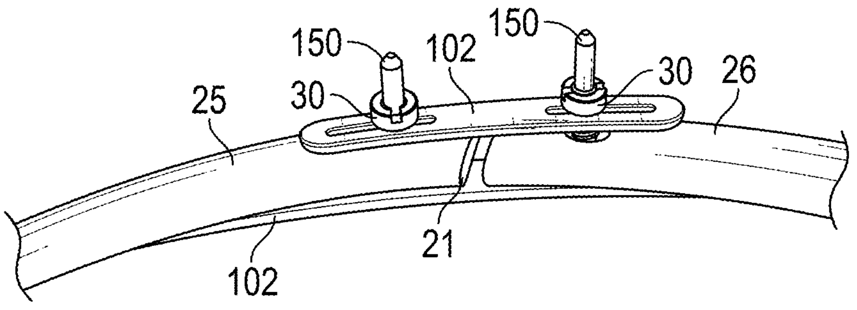
FIG. 28 is a perspective view of the fracture plating system of FIG. 26 in a deployed configuration spanning an exemplary bone fracture.

FIG. 28 is a perspective view of the fracture plating system 100 in a deployed configuration spanning an exemplary bone first fracture 21. The second plate 102' may be secured to the exterior surface of bone with one or more locking nuts 30. An anti-rotation fastener 150 length may be chosen from a range of fastener lengths such that, which the second plate 102' proximate the exterior surface of the portion of bone, the threaded portion 160 exposed beyond the second plate 102' may be greater than or equal to the thickness 38 of the locking nut 30. Alternatively, an anti-rotation fastener 150 length may be chosen from a range of fastener lengths such that, which the second plate 102' proximate the exterior surface of the portion of bone, the threaded portion 160 exposed beyond the second plate 102' may be greater than or equal to the thickness 38 of the locking nut 30 plus the thickness 56 of the washer 50.

Figure 29:
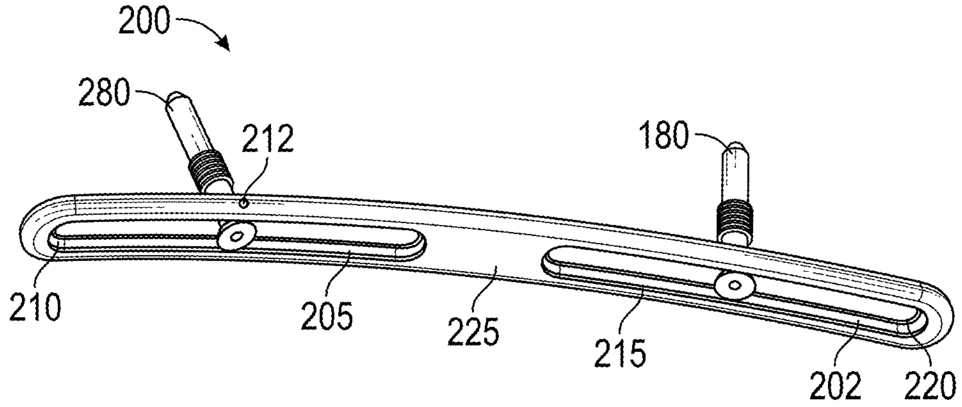
FIG. 29 is a perspective view of a fracture plating system according to an embodiment of the present disclosure.

FIG. 29 is a perspective view of a fracture plating system 200 according to an embodiment of the present disclosure. The fracture plating system 200 may include similar features as the fracture plating system 100 previously described. The fracture plating system 200 may include a fixed hinge fastener. The fixed hinge fastener may be configured to provide a lagging effect to facilitate compression of a fracture. The fracture plating system 200 may include a first fastener in a fixed location within a first slot of a plate and a second fastener that may be translated within a second slot of a plate.

The fracture plating system 200 may include a first fastener configured as one of a fixed hinge fastener 250 and a circular head fixed hinge fastener 280. And a second fastener configured as one of an anti-rotation fastener 150 and a circular head fastener 180. The first fastener may be captively received within a first slot 205 of a plate 202 so that the first fastener may be coupled to the first slot. The second fastener may be captively received within a second slot 215 of the plate 202 so that the second fastener may be coupled to the second slot.

The fracture plating system 200 may include a plate 202. The plate 202 may include a plate radius 204, a first slot 205, a second slot 215, a pin aperture 212, and a central portion 225. The first slot 205 may include a first threaded feature 210 and the second slot 215 may include a second threaded feature 220. The central portion 225 may be generally in the center of the plate 202 and may separate the first slot 205 and the second slot 215.

The first threaded feature 210 may be configured to threadably engage a threaded portion 260 of the fixed hinge fastener 250 and/or a threaded portion 290 of the circular head fixed hinge fastener 280 to allow the threaded portion 260 and/or the threaded portion 290 to pass through the first slot 205. The second threaded feature 220 may be configured to threadably engage a threaded portion 160 of the anti-rotation fastener 150 and/or a threaded portion 190 of the circular head fastener 180 to allow the threaded portion 160 and/or the threaded portion 190 to pass through the second slot 215.

The plate 202 may be configured such that a plate length is within a range of lengths from 30 mm to 300 mm. The plate 202 may be one of a set of differently-sized implants, each having a different plate length. The plate radius 204 may generally match a contour of an interior surface of a rib. The plate 202 may further be one of a set of differently-sized implants, each having a different plate radius 204.

Figure 30:
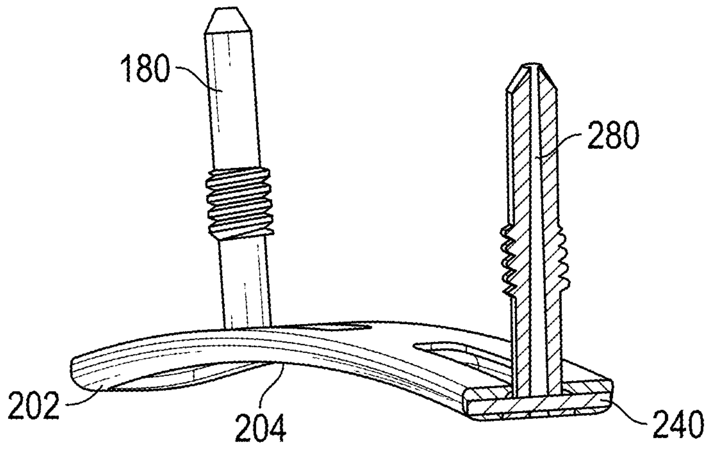
FIG. 30 is a perspective section view of the fracture plating system of FIG. 29.
Figure 31:
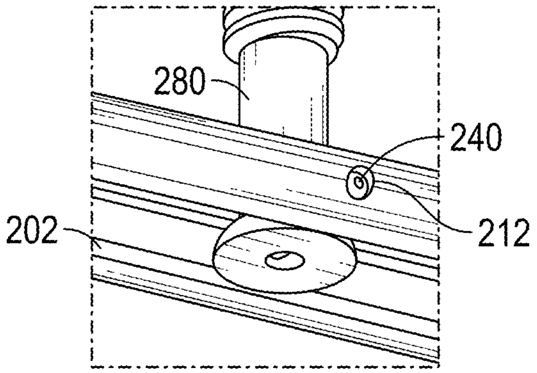
FIG. 31 is a partial bottom perspective view of the fracture plating system of FIG. 29.

FIG. 30 is a perspective section view of the fracture plating system 200. FIG. 31 is a partial bottom perspective view of the fracture plating system 200. The pin aperture 212 may span the width of the plate 202 and may be located within the first slot 205. The pin aperture 212 may further be configured to receive at least one hinge pin 240. The pin aperture 212 may be configured to receive the at least one hinge pin 240 as a press fit so that the at least one hinge pin 240 may be held in place within the pin aperture 212. Additionally, or alternatively, the at least one hinge pin 240 may be secured to the plate 202 within the pin aperture 212 by welding, solder, adhesive, or other suitable means.

Figure 32A:
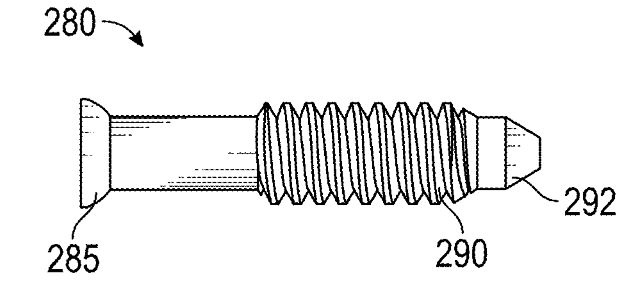
FIG. 32A is a top view of a circular head fixed hinge fastener of the fracture plating system of FIG. 29 according to an embodiment of the present disclosure.
Figure 32B:
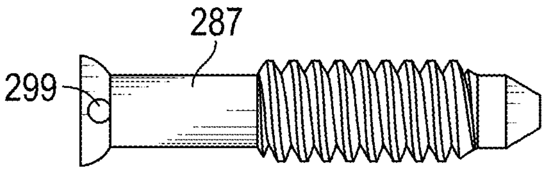
FIG. 32B is a front view of the circular head fixed hinge fastener of FIG. 32A.
Figure 32C:
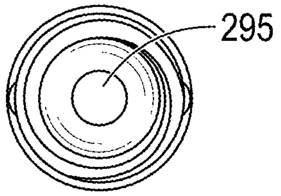
FIG. 32C is a side view of the circular head fixed hinge fastener of FIG. 32A.

FIG. 32A is a top view of a circular head fixed hinge fastener 280 of the fracture plating system 200 according to an embodiment of the present disclosure. FIG. 32B is a front view of the circular head fixed hinge fastener 280. FIG. 32C is a side view of the circular head fixed hinge fastener 280. The circular head fixed hinge fastener 280 may include a head portion 285, a shank portion 287, a threaded portion 290, a tip portion 292, a cannulation 295, and a pin aperture 299.

The head portion 285 may be configured to be received within the first slot 205. The threaded portion 290 may be larger than a width of the first slot 205 to prevent the circular head fixed hinge fastener 280 from disengaging from the plate 202. The head portion 285 may include the pin aperture 299. The pin aperture 299 may be configured to slidably receive at least one hinge pin 240. The at least one hinge pin 240 may also be received within the pin aperture 212 and may prevent translation of the circular head fixed hinge fastener 280 within the first slot 205.

The shank portion 287 may be smaller than a width of the first slot 205 to allow the circular head fixed hinge fastener

280 to translate along the length of the first slot 205. The tip portion 292 may be configured to ease insertion of the circular head fixed hinge fastener 280 into a hole in a bone portion. The cannulation 295 may be configured to slidably receive a tether 60.

The at least one hinge pin 240 may be configured to engage the pin aperture 212 of the plate 202 and a pin aperture 299 of the circular head fixed hinge fastener 280 so that the at least one hinge pin 240 is not received within the cannulation 295 and does not impede the tether 60 from passing through the cannulation 295.

The circular head fixed hinge fastener 280 may be configured within a range of lengths from 5 mm to 30 mm and within a range of diameters from 3 mm to 8 mm. The circular head fixed hinge fastener 280 may be one of a set of differently-sized implants, each having a different length and/or diameter.

Figure 33A:
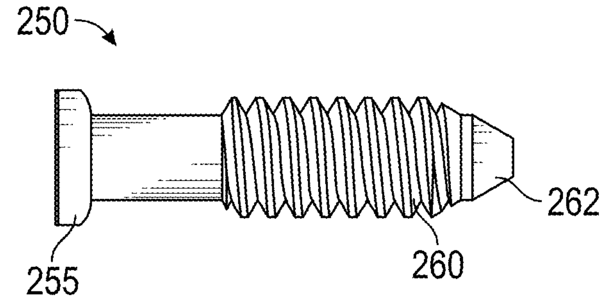
FIG. 33A is a top view of a fixed hinge fastener of the fracture plating system of FIG. 29 according to an embodiment of the present disclosure.
Figure 33B:
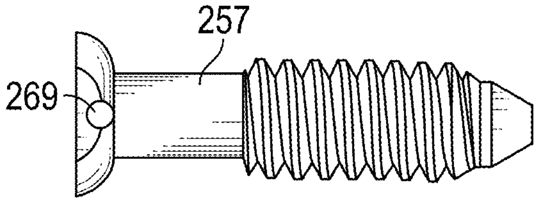
FIG. 33B is a front view of the fixed hinge fastener of FIG. 33A.
Figure 33C:
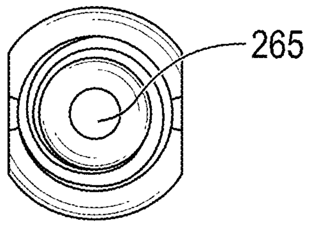
FIG. 33C is a side view of the fixed hinge fastener of FIG. 33A.

FIG. 33A is a top view of a fixed hinge fastener 250 of the fracture plating system 200 according to an embodiment of the present disclosure. FIG. 33B is a front view of the fixed hinge fastener 250. FIG. 33C is a side view of the fixed hinge fastener 250. The fixed hinge fastener 250 may include a head portion 255, a shank portion 257, a threaded portion 260, a tip portion 262, a cannulation 265, and a pin aperture 269.

The head portion 255 may be configured to be received within the first slot 205. The threaded portion 260 may be larger than a width of the first slot 205 to prevent the fixed hinge fastener 250 from disengaging from the plate 202. The head portion 255 may include the pin aperture 269. The pin aperture 269 may be configured to slidably receive at least one hinge pin 240. The at least one hinge pin 240 may also be received within the pin aperture 212 and may prevent translation of the fixed hinge fastener 250 within the first slot 205.

The shank portion 257 may be smaller than a width of the first slot 205 to allow the fixed hinge fastener 250 to translate along the length of the first slot 205. The tip portion 262 may be configured to ease insertion of the fixed hinge fastener 250 into a hole in a bone portion. The cannulation 265 may be configured to slidably receive a tether 60.

The at least one hinge pin 240 may be configured to engage the pin aperture 212 of the plate 202 and a pin aperture 269 of the fixed hinge fastener 250 so that the at least one hinge pin 240 is not received within the cannulation 265 and does not impede the tether 60 from passing through the cannulation 265.

The fixed hinge fastener 250 may be configured within a range of lengths from 5 mm to 30 mm and within a range of diameters from 3 mm to 8 mm. The fixed hinge fastener 250 may be one of a set of differently-sized implants, each having a different length and/or diameter.

Figure 34:
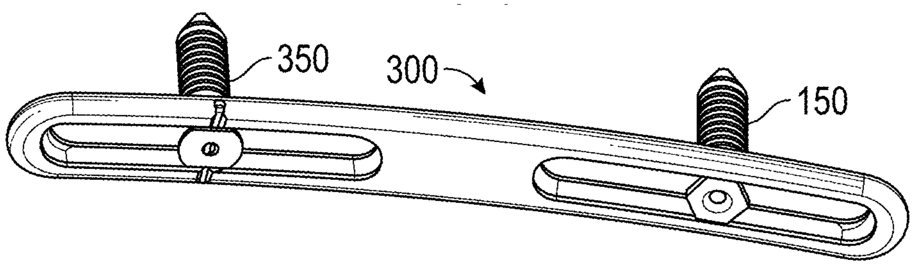
FIG. 34 is a perspective view of a fracture plating system according to an embodiment of the present disclosure.

FIG. 34 is a perspective view of a fracture plating system 300 according to an embodiment of the present disclosure. The fracture plating system 300 may include similar features as the fracture plating system 100 and the fracture plating system 200 previously described. The fracture plating system 300 may include a fixed hinge fastener. The fixed hinge fastener may be configured to provide a lagging effect to facilitate compression of a fracture. The fracture plating system 300 may include a first fastener in a fixed location within a first slot of a plate and a second fastener that may be translated within a second slot of a plate.

The fracture plating system 300 may include a first fastener configured as a fixed hinge fastener 350. And a second fastener configured an anti-rotation fastener 150. The first fastener may be captively received within a first slot 305 of a plate 302. The second fastener may be captively received within a second slot 315 of the plate 302.

The fracture plating system 300 may include a plate 302. The plate 302 may include a plate radius 304, a first slot 305, a second slot 315, a pin channel 312, and a central portion 325. The first slot 305 may include a first threaded feature 310 and the second slot 315 may include a second threaded feature 320. The central portion 325 may be generally in the center of the plate 302 and may separate the first slot 305 and the second slot 315.

Figure 35:
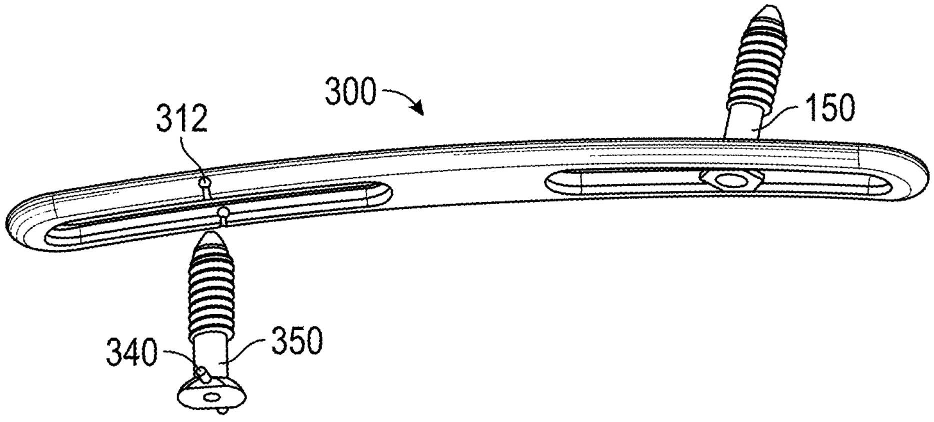
FIG. 35 is a bottom perspective view of the fracture plating system of FIG. 34 in a pre-assembled configuration.

FIG. 35 is a bottom perspective view of the fracture plating system 300 in a pre-assembled configuration. The first threaded feature 310 may be configured to threadably engage a threaded portion 360 of the fixed hinge fastener 350 to allow the threaded portion 360 to pass through the first slot 305. The second threaded feature 320 may be configured to threadably engage a threaded portion 160 of the anti-rotation fastener 150 and/or a threaded portion 190 of the circular head fastener 180 to allow the threaded portion 160 and/or the threaded portion 190 to pass through the second slot 315.

The pin channel 312 may span the width of the plate 302 and may be located within the first slot 305. The pin channel 312 may further be configured to receive at least one hinge pin 340. The pin channel 312 may be configured to receive the at least one hinge pin 340 as a snap fit so that the at least one hinge pin 340 may be held in place within the pin channel 312. The pin channel 312 may be configured so that a fixed hinge fastener 350 may be snapped into the plate 302 during a surgical procedure, and may allow a user to tailor the length of the fixed hinge fastener 350 based on an anatomy of a patient while still having the benefits of a fixed fastener for applying compression to a fracture. The fixed hinge fastener 350, the plate 302, and the pin channel 312 may be configured so that the, when the hinge pin 340 is snapped into the pin channel 312, the fixed hinge fastener 350 may rotate about the hinge pin 340 but may not translate along the first slot 305.

Figure 36A:
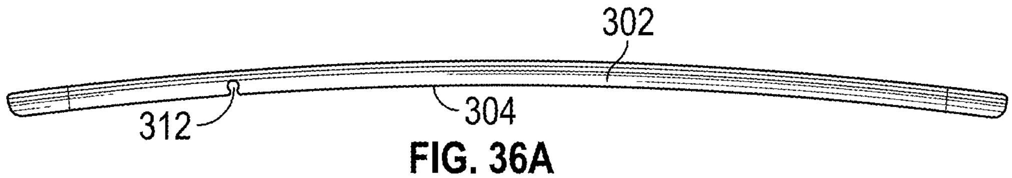
FIG. 36A is a front view of a plate of the fracture plating system of FIG. 34 according to an embodiment of the present disclosure.
Figure 36B:
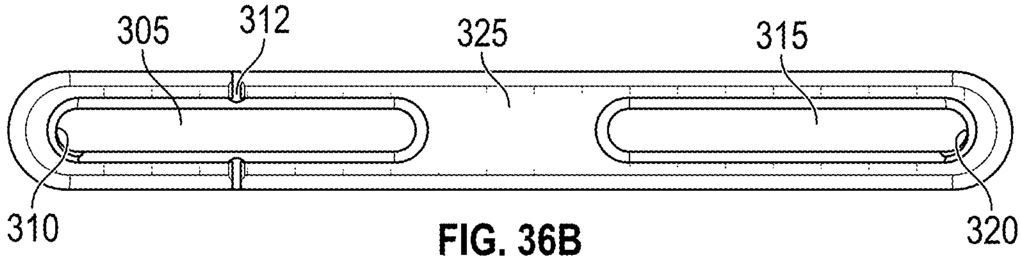
FIG. 36B is a bottom view of the plate of FIG. 36A.

FIG. 36A is a front view of a plate 302 of the fracture plating system 300 according to an embodiment of the present disclosure. FIG. 36B is a bottom view of the plate 302. The plate 302 may be configured such that a plate length is within a range of lengths from 30 mm to 300 mm. The plate 302 may be one of a set of differently-sized implants, each having a different plate length. A plate radius 304 may generally match a contour of an interior surface of a rib. The plate 302 may further be one of a set of differently-sized implants, each having a different plate radius 304.

Figure 37A:
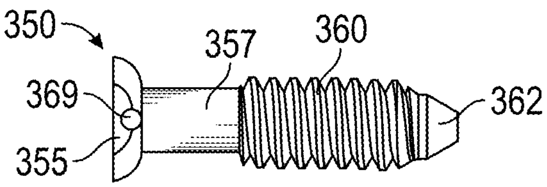
FIG. 37A is a front view of a fixed hinge fastener of the fracture plating system of FIG. 34 according to an embodiment of the present disclosure.
Figure 37B:
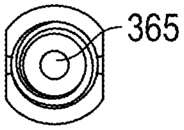
FIG. 37B is a side view of the fixed hinge fastener of FIG. 37A.
Figure 38A:
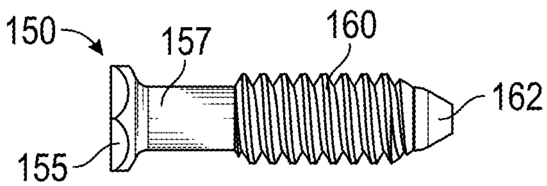
FIG. 38A is a front view of the anti-rotation fastener of FIG. 3A.
Figure 38B:
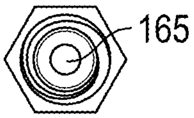
FIG. 38B is a side view of the anti-rotation fastener of FIG. 38A.

FIG. 37A is a front view of a fixed hinge fastener 350 of the fracture plating system 300 according to an embodiment of the present disclosure. FIG. 37B is a side view of the fixed hinge fastener 350. FIG. 38A is a front view of the anti-rotation fastener 150 and FIG. 38B is a side view of the anti-rotation fastener 150. The fixed hinge fastener 350 may include a head portion 355, a shank portion 357, a threaded portion 360, a tip portion 362, a cannulation 365, and a pin aperture 369.

The head portion 355 may be configured to be received within the first slot 305. The threaded portion 360 may be larger than a width of the first slot 305 to prevent the fixed hinge fastener 350 from disengaging from the plate 302. The head portion 355 may include the pin aperture 369. The pin aperture 369 may be configured to slidably receive at least one hinge pin 340. The at least one hinge pin 340 may also be received within the pin channel 312 and may prevent translation of the fixed hinge fastener 350 within the first slot 305.

The shank portion 357 may be smaller than a width of the first slot 305 to allow the fixed hinge fastener 350 to translate along the length of the first slot 305. The tip portion 362 may be configured to ease insertion of the fixed hinge fastener 350 into a hole in a bone portion. The cannulation 365 may be configured to slidably receive a tether 60.

The at least one hinge pin 340 may be configured to engage the pin channel 312 of the plate 302 and a pin aperture 369 of the fixed hinge fastener 350 so that the at least one hinge pin 340 is not received within the cannulation 365 and does not impede the tether 60 from passing through the cannulation 365. The at least one hinge pin 340 may be fabricated as a separate component from the fixed hinge fastener 350. Alternatively, the at least one hinge pin 340 and the fixed hinge fastener 350 may be fabricated as a single integral component.

The fixed hinge fastener 350 may be configured within a range of lengths from 5 mm to 30 mm and within a range of diameters from 3 mm to 8 mm. The fixed hinge fastener 350 may be one of a set of differently-sized implants, each having a different length and/or diameter.

Figure 39:
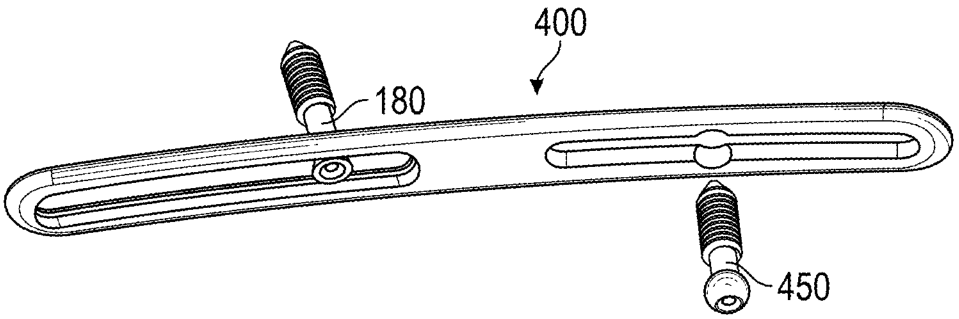
FIG. 39 is a perspective view of a fracture plating system according to an embodiment of the present disclosure.

FIG. 39 is a perspective view of a fracture plating system 400 according to an embodiment of the present disclosure. The fracture plating system 400 may include similar features as the fracture plating system 100, the fracture plating system 200, and the fracture plating system 300 previously described. The fracture plating system 400 may include a ball-headed fastener 450. The ball-headed fastener 450 may be configured to provide a lagging effect and/or poly-axial rotation of the ball-headed fastener 450 to facilitate compression of a fracture. The fracture plating system 400 may include a first fastener that may be translated within a first slot of a plate and a second fastener in a fixed location within a first slot of a plate.

Figure 40:
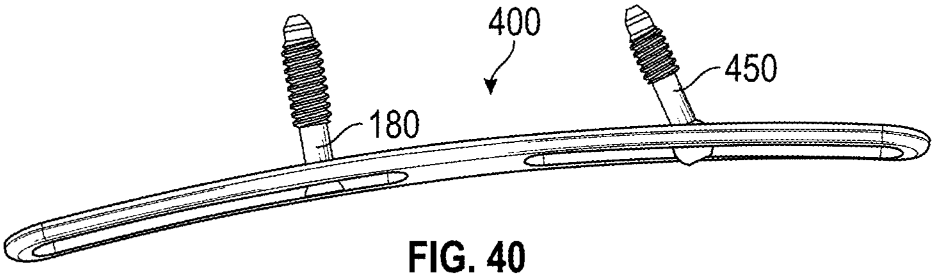
FIG. 40 is a bottom perspective view of the fracture plating system of FIG. 39.

FIG. 40 is a bottom perspective view of the fracture plating system 400. The fracture plating system 400 may include a first fastener configured as a circular head fastener 180 and a second fastener configured as a ball-headed fastener 450. The first fastener may be captively received within a first slot 405 of a plate 402. The second fastener may be captively received within a second slot 415 of the plate 402.

Figure 41A:
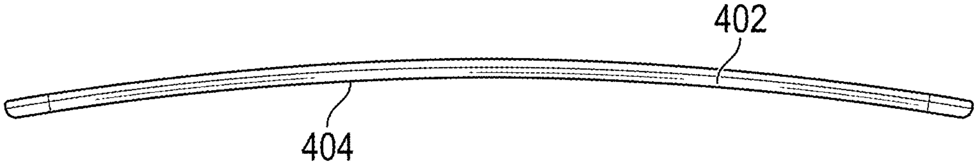
FIG. 41A is a front view of a plate of the fracture plating system of FIG. 39 according to an embodiment of the present disclosure.
Figure 41B:
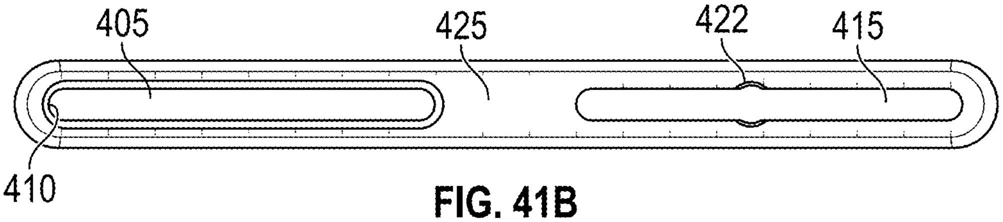
FIG. 41B is a bottom view of the plate of FIG. 41A.

FIG. 41A is a front view of a plate 402 of the fracture plating system 400 according to an embodiment of the present disclosure. FIG. 41B is a bottom view of the plate 402. The plate 402 may include a plate radius 404, a first slot 405, a second slot 415, a socket 422, and a central portion 425. The first slot 405 may include a first threaded feature 410 and the second slot 415 may include a socket 422. The central portion 425 may be generally in the center of the plate 402 and may separate the first slot 405 and the second slot 415.

The first threaded feature 410 may be configured to threadably engage a threaded portion 190 of the circular head fastener 180 to allow the threaded portion 190 to pass through the first slot 305.

The socket 422 may be located within the second slot 415. The socket 422 may further be configured to receive a head portion 455 of the ball-headed fastener 450. The socket 422 may be configured to receive the head portion 455 as a snap fit so that the head portion 455 may be held in place within the socket 422. The socket 422 may be configured so that a ball-headed fastener 450 may be snapped into the plate 402 during a surgical procedure, and may allow a user to tailor the length of the ball-headed fastener 450 based on an anatomy of a patient while still having the benefits of a fixed fastener for applying compression to a fracture. The ball-headed fastener 450, the plate 402, and the socket 422 may be configured so that the, when the head portion 455 is snapped into the socket 422, the ball-headed fastener 450 may rotate about the head portion 455 but may not translate along the second slot 415.

The plate 402 may be configured such that a plate length is within a range of lengths from 30 mm to 300 mm. The plate 402 may be one of a set of differently-sized implants, each having a different plate length. A plate radius 404 may generally match a contour of an interior surface of a rib. The plate 402 may further be one of a set of differently-sized implants, each having a different plate radius 404.

Figure 42A:
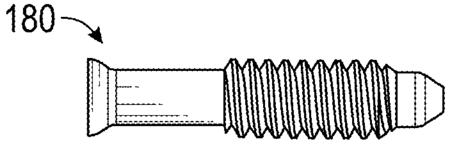
FIG. 42A is a front view of the circular head fastener of FIG. 4A.
Figure 42B:
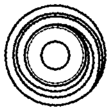
FIG. 42B is a side view of the circular head fastener of FIG. 42A
Figure 43A:
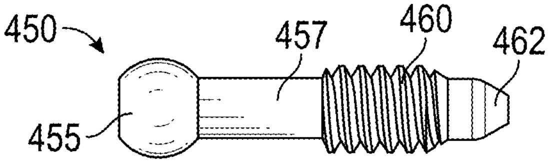
FIG. 43A is a front view of a ball-headed fastener of the fracture plating system of FIG. 39 according to an embodiment of the present disclosure.
Figure 43B:
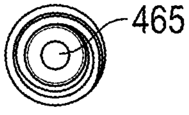
FIG. 43B is a side view of the ball-headed fastener of FIG. 43A.

FIG. 42A is a front view of the circular head fastener 180 and FIG. 42B is a side view of the circular head fastener 180. FIG. 43A is a front view of a ball-headed fastener 450 of the fracture plating system 400 according to an embodiment of the present disclosure. FIG. 43B is a side view of the ball-headed fastener 450. The ball-headed fastener 450 may include a head portion 455, a shank portion 457, a threaded portion 460, a tip portion 462, and a cannulation 465.

The head portion 455 may be configured to be received within the socket 422 and may prevent translation of the ball-headed fastener 450 within the second slot 415. The shank portion 457 may be smaller than a width of the second slot 415 to allow the ball-headed fastener 450 to rotate about the head portion 455. The tip portion 462 may be configured to ease insertion of the ball-headed fastener 450 into a hole in a bone portion. The cannulation 465 may be configured to slidably receive a tether 60.

The ball-headed fastener 450 may be configured within a range of lengths from 5 mm to 30 mm and within a range of diameters from 3 mm to 8 mm. The ball-headed fastener 450 may be one of a set of differently-sized implants, each having a different length and/or diameter.

Figure 44A:
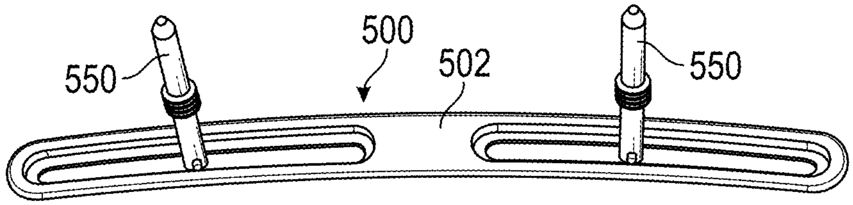
FIG. 44A is a perspective view of a fracture plating system according to an embodiment of the present disclosure.
Figure 44B:
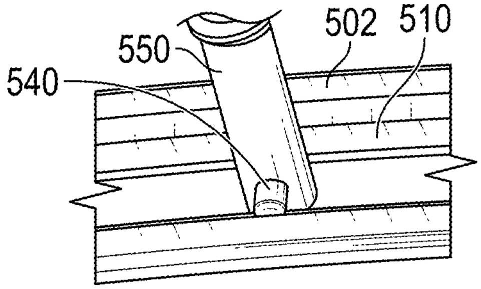
FIG. 44B is a partial perspective view of the fracture plating system of FIG. 44A.

FIG. 44A is a perspective view of a fracture plating system 500 according to an embodiment of the present disclosure. FIG. 44B is a partial perspective view of the fracture plating system 500. The fracture plating system 500 may include similar features as other fracture plating systems previously described within the present disclosure. The fracture plating system 500 may include a pin fastener. The pin fastener may be configured to translate along a length of a slot in a plate to facilitate compression of a fracture. The fracture plating system 500 may include a first fastener and a second fastener that each may be translated within a slot of a plate.

Figure 45:
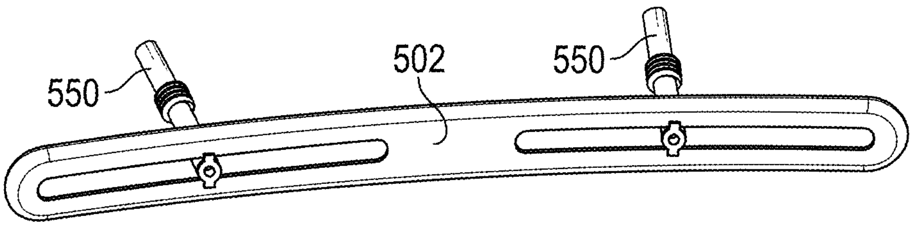
FIG. 45 is a bottom perspective view of the fracture plating system of FIG. 44A.

FIG. 45 is a bottom perspective view of the fracture plating system 500. The fracture plating system 500 may include a first fastener configured as a pin fastener 550. And a second fastener configured as a pin fastener 550. The first fastener and the second fastener may be captively received within a first slot 505 and a second slot 515 of a plate 502, respectively.

Figure 46A:
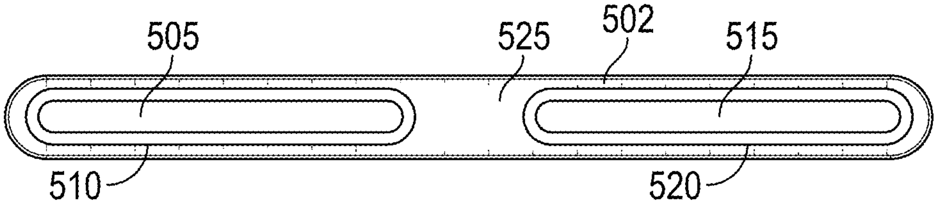
FIG. 46A is a top view of a plate of the fracture plating system of FIG. 44A according to an embodiment of the present disclosure.
Figure 46B:
FIG. 46B is a front view of the plate of FIG. 46A.

FIG. 46A is a top view of a plate 502 of the fracture plating system 500 according to an embodiment of the present disclosure. FIG. 46B is a front view of the plate 502. The plate 502 may include a plate radius 504, a first slot 505, a second slot 515, and a central portion 525. The first slot 505 may include a first pocket 510 and the second slot 515 may include a second pocket 520. The central portion 225 may be generally in the center of the plate 202 and may separate the first slot 205 and the second slot 215.

The first pocket 510 and the second pocket 520 may be configured to receive a pin 540 received within a pin fastener 550. The plate 502 may be one of a set of differently-sized implants, each having a different plate length. A plate radius 504 may generally match a contour of an interior surface of a rib. The plate 502 may further be one of a set of differently-sized implants, each having a different plate radius 504.

Figure 47A:
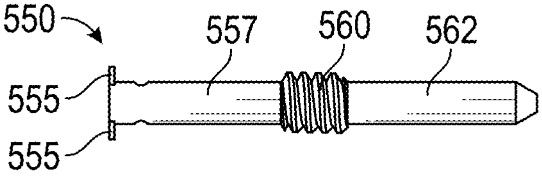
FIG. 47A is a top view of a pin fastener of the fracture plating system of FIG. 44A according to an embodiment of the present disclosure.
Figure 47B:
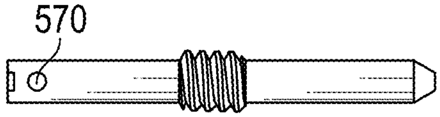
FIG. 47B is a front view of the pin fastener of FIG. 47A.
Figure 47C:
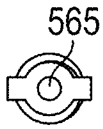
FIG. 47C is a side view of the pin fastener of FIG. 47A.

FIG. 47A is a top view of a pin fastener 550 of the fracture plating system 500 according to an embodiment of the present disclosure. FIG. 47B is a front view of the pin fastener 550 and FIG. 47C is a side view of the pin fastener 550. The pin fastener may include a tab portion 555, a shank portion 557, a threaded portion 560, a tip portion 562, a cannulation 565, and a pin aperture 570.

The pin aperture 570 may be configured to securably receive at least one pin 540 such that, when the pin fastener 550 is assembled with the plate 502, the at least one pin 540 is received within one of the first pocket 510 and the second pocket 520. The tab portion 555 may be configured so that, when the at least one pin 540 is received with one of the first pocket 510 and the second pocket 520 and is aligned generally perpendicular to a long axis of the plate 502, the tab portion 555 engages a bottom surface of the plate 502 to hold the pin fastener 550 captively received within one of the first slot 505 and the second slot 515 while allowing the pin fastener 550 to translate along a length of one of the first slot 505 and the second slot 515.

The shank portion 557 may be smaller than a width of the first slot 505 and/or the second slot 515 to allow the pin fastener 550 to translate along the length of the first slot 505 and/or the second slot 515. The tip portion 562 may be configured to ease insertion of the pin fastener 550 into a hole in a bone portion. The cannulation 565 may be configured to slidably receive a tether 60. The threaded portion 560 may be configured to threadably receive a locking nut 30.

The at least one pin 540 may be configured to be received within the first pocket 510 and/or the second pocket 520 of the plate 502 and a pin aperture 570 of the pin fastener 550 so that the at least one pin 540 is not received within the cannulation 565 and does not impede the tether 60 from passing through the cannulation 565.

The pin fastener 550 may be configured within a range of lengths from 5 mm to 30 mm and within a range of diameters from 3 mm to 8 mm. The pin fastener 550 may be one of a set of differently-sized implants, each having a different length and/or diameter.

Each of the previously described fracture plating systems of the present disclosure may be utilized to treat multiple fractures of a single portion of bone. Each of the previously described fracture plating systems of the present disclosure may be assemblable in a modular fashion whereby a plate may be selectable from a range of differently sized plates, a plurality of fasteners may be selectable from a range of differently sized fasteners, and a locking nut may be selectable from a range of differently sized locking nuts. The fracture plating system may be configured to be assembled prior to implantation within a patient. The fracture plating system may be configured to be assembled on a back table during a surgical procedure prior to implantation within a patient. The fracture plating system may be configured so that a plate, two or more fasteners, and two or more locking nuts may be selected based on patient anatomy and/or the location and/or severity of one or more fractures. Additionally, or alternatively, the fracture plating system may be configured so that a plate, two or more fasteners, and two or more locking nuts may be selected based surgical and/or radiographic assessment of the patient and/or the location and/or severity of the one or more fractures.

Figure 48A:
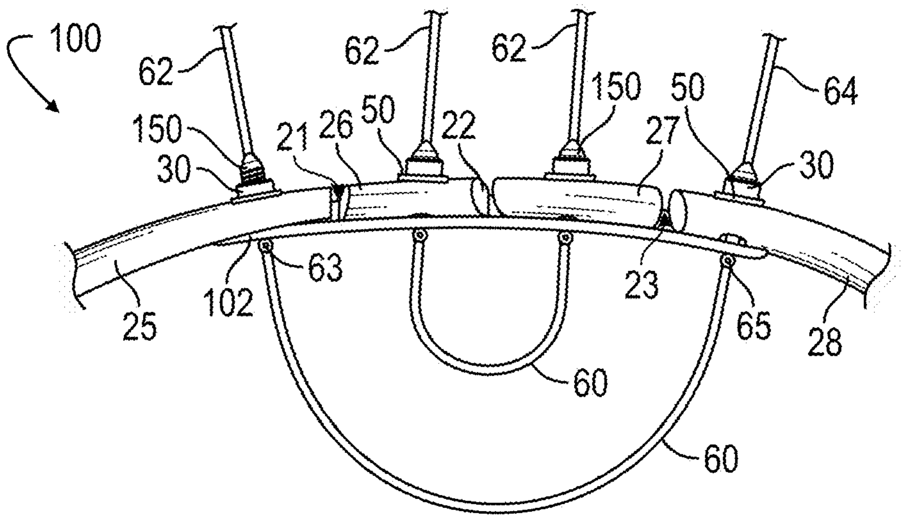
FIG. 48A is a front view of a fracture plating system in a partially deployed configuration according to an embodiment of the present disclosure spanning a plurality of exemplary bone fractures.
Figure 48B:
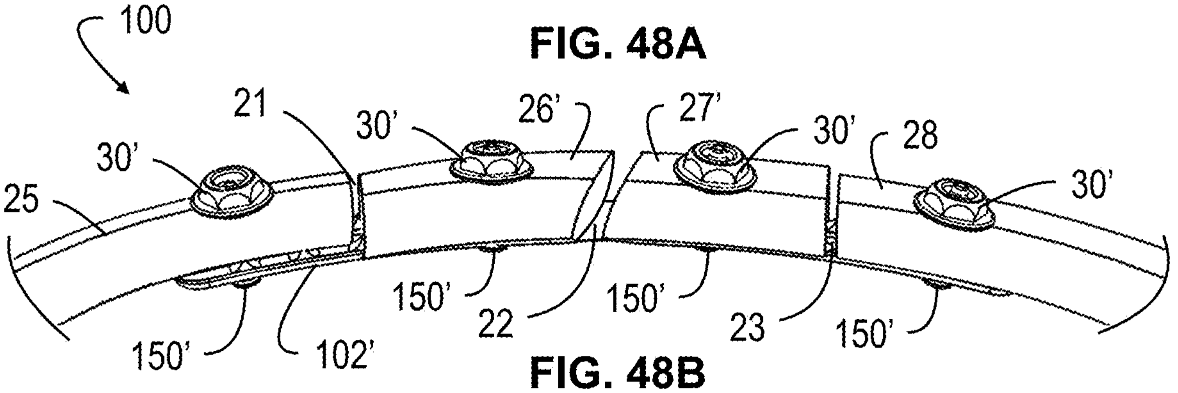
FIG. 48B is a perspective view of a fracture plating system secured to a bone with multiple fractures according to an embodiment of the present disclosure.
Figure 48C:
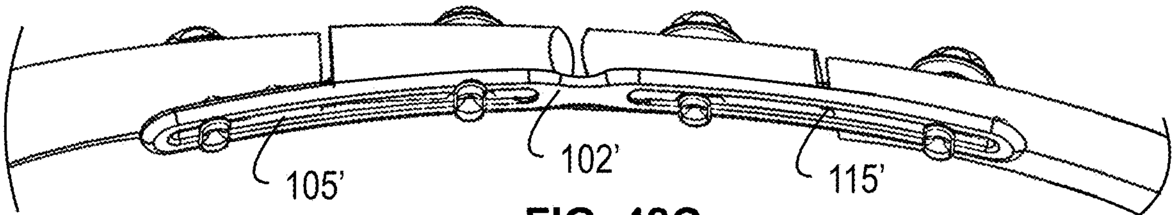
FIG. 48C is a perspective view of the fracture plating system of FIG. 48B.

FIG. 48A is a front view of a fracture plating system 100 in a partially deployed configuration according to an embodiment of the present disclosure spanning a plurality of exemplary bone fractures. FIG. 48B is a perspective view of a fracture plating system 100 secured to a bone with multiple fractures according to an embodiment of the present disclosure. FIG. 48C is a perspective view of the fracture plating system 100 of FIG. 48B. The fracture plating system 100 may include a plate 102', fasteners 150', and locking nuts 30'.

The fracture plating system 100 may be configured to stabilize a multiple fractures of a bone of a patient, wherein the multiple fractures define one or more flail segments. For example, the fracture plating system 100 may be configured to stabilize a first fracture 21, a second fracture 22 and a third fracture 23 of a bone, wherein the first fracture 21 and the second fracture 22 define a first flail segment 26' and the second fracture 22 and the third fracture 23 define a second flail segment 27'.

The fracture plating system may include a plate 102' having a first slot 105' and a second slot 115'. The plate 102' may span the first fracture 21, the second fracture 22, and the third fracture 23 so that at least one fastener 150' may be received in the first slot 105' or the second slot 115' and in the bone on both sides of each of the first fracture 21, the second fracture 22, and the third fracture 23. The first slot 105' may span one or more of the first fracture 21, the second fracture 22, and the third fracture 23. Additionally, the second slot 115' may also span one or more of the first fracture 21, the second fracture 22, and the third fracture 23.

Figure 48D:
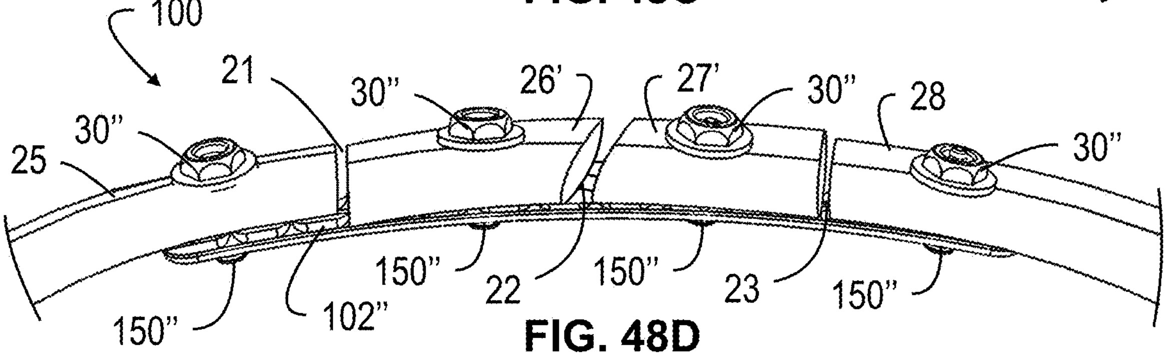
FIG. 48D is a perspective view of a fracture plating system secured to a bone with multiple fractures according to an embodiment of the present disclosure.
Figure 48E:
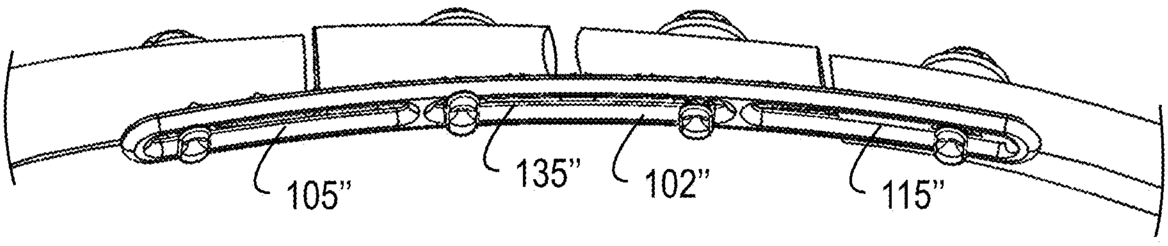
FIG. 48E is a perspective view of the fracture plating system of FIG. 48D.

FIG. 48D is a perspective view of a fracture plating system 100 secured to a bone with multiple fractures according to an embodiment of the present disclosure. FIG. 48E is a perspective view of the fracture plating system 100 of FIG. 48D. The fracture plating system 100 may include a plate 102", fasteners 150", and locking nuts 30".

The fracture plating system 100 may be configured to stabilize a multiple fractures of a bone of a patient, wherein the multiple fractures define one or more flail segments. For example, the fracture plating system 100 may be configured to stabilize a first fracture 21, a second fracture 22 and a third fracture 23 of a bone, wherein the first fracture 21 and the second fracture 22 define a first flail segment 26' and the second fracture 22 and the third fracture 23 define a second flail segment 27'.

The fracture plating system may include a plate 102" having a first slot 105", a second slot 115", and a third slot 135". The plate 102" may span the first fracture 21, the second fracture 22, and the third fracture 23 so that at least one fastener 150" may be received in the first slot 105", the second slot 115', or the third slot 135" and in the bone on both sides of each of the first fracture 21, the second fracture 22, and the third fracture 23. The first slot 105" may span one or more of the first fracture 21, the second fracture 22, and the third fracture 23. Additionally, the second slot 115" may also span one or more of the first fracture 21, the second fracture 22, and the third fracture 23. Additionally, the third slot 135" may also span one or more of the first fracture 21, the second fracture 22, and the third fracture 23.

Figure 49:
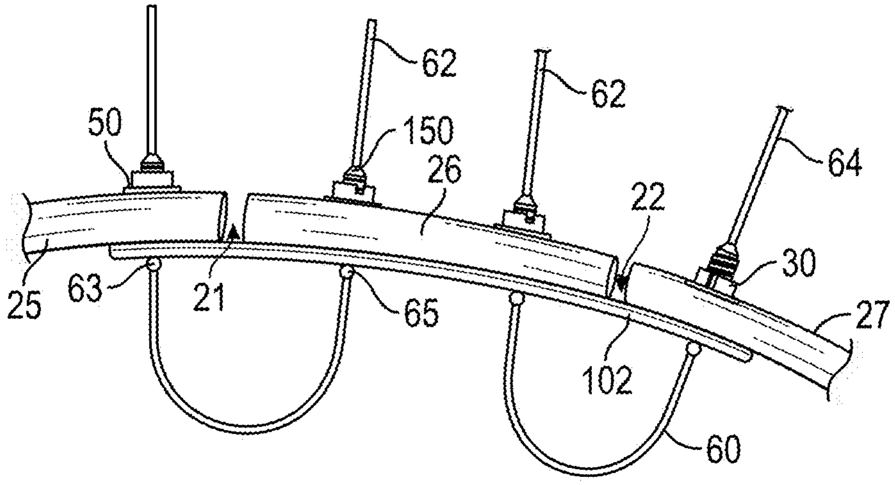
FIG. 49 is a front view of a fracture plating system in a partially deployed configuration according to an embodiment of the present disclosure spanning a plurality of exemplary bone fractures.
Figure 50:
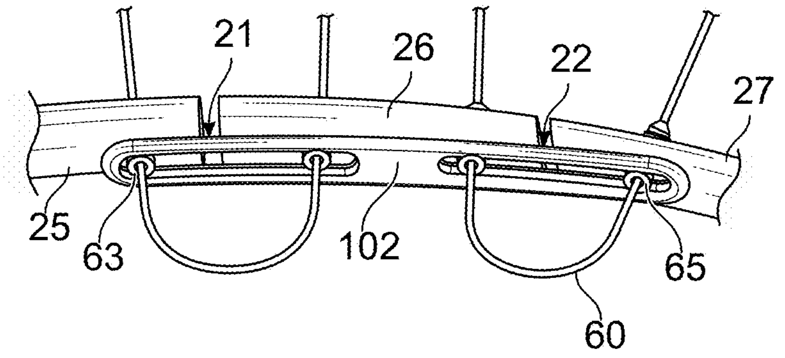
FIG. 50 is a bottom perspective view of the fracture plating system of FIG. 49 in a partially deployed configuration spanning a plurality of exemplary bone fractures.

FIG. 49 is a front view of a fracture plating system in a partially deployed configuration according to an embodiment of the present disclosure spanning a plurality of exemplary bone fractures. FIG. 50 is a bottom perspective view of the fracture plating system in a partially deployed configuration spanning a plurality of exemplary bone fractures.

The fracture plating system may be configured to stabilize a single fracture of a bone. Additionally, or alternatively, the fracture plating system may be configured to stabilize two fractures of a bone. Additionally, or alternatively, the fracture plating system may be configured to stabilize three or more fractures of a bone. Additionally, or alternatively, the fracture plating system may be configured to stabilize multiple fractures of a bone, wherein the multiple fractures define one or more flail segments. The fracture plating system may include multiple tethers, each configured to guide up to two fasteners to an interior surface of the bone and to one or more slots of the plate.

The fracture plating system previously described within the present disclosure may be used to stabilize multiple fractures of a bone. The multiple fractures may result in one or more flail segments and may result in flail chest. The fracture plating system previously described within the present disclosure may be used to stabilize one or more flail segments.

The fracture plating system previously described within the present disclosure may include a plate that may be configured to span the multiple fractures and four fasteners, each configured to be received in the bone and in one or more slots of the plate. The four fasteners may be configured to be received in the bone on opposite sides of each of the first fracture 21 and the second fracture 22. The fracture plating system may also include four locking nuts configured to receive one of the four fasteners and cooperate with one of the four fasteners to secure the plate to the interior surface of the bone.

Additionally, or alternatively, the fracture plating system previously described within the present disclosure may include a plate that may be configured to span a first fracture 21 and a second fracture 22 and at least three fasteners, each configured to be received in the bone and in one or more slots of the plate. The at least three fasteners may be configured to be received in the bone on opposite sides of each of the first fracture 21 and the second fracture 22. The fracture plating system may also include at least three locking nuts configured to receive one of the at least three fasteners and cooperate with one of the at least three fasteners to secure the plate to the interior surface of the bone.

The fracture plating system previously described within the present disclosure may be used to facilitate reduction of a first fracture 21, a second fracture 22, and a third fracture 23 whereby a first tether 60 may be received within a first fastener that is received within a first bone portion 25 and a fourth fastener that may be received within a fourth bone portion 28. A second tether 60 may be received within a second fastener that may be received within a second bone portion 26 and a third fastener that may be received within a third bone portion 27.

Applying a tension force to a first tether end 62 and a second tether end 64 of a first tether 60 and a first tether end 62 and a second tether end 64 of a second tether 60 may facilitate reduction of the first fracture 21, the second fracture 22, and the third fracture 23. The fracture plating system may then be secured by securing a locking nut to each of the fasteners.

The fracture plating system previously described within the present disclosure may be used to facilitate reduction of a first fracture 21 and a second fracture 22 whereby a first tether 60 is received within a first fastener that may be received within a first bone portion 25 and a second fastener that may be received within a second bone portion 26. A second tether 60 may be received within a third fastener that may be received within a third bone portion 27 and a fourth fastener that may be received within a fourth bone portion 28.

Applying a tension force to a first tether end 62 and a second tether end 64 of a first tether 60 and a first tether end 62 and a second tether end 64 of a second tether 60 may facilitate reduction of the first fracture 21 and the second fracture 22. The fracture plating system may then be secured by securing a locking nut to each of the fasteners.

Figure 51:
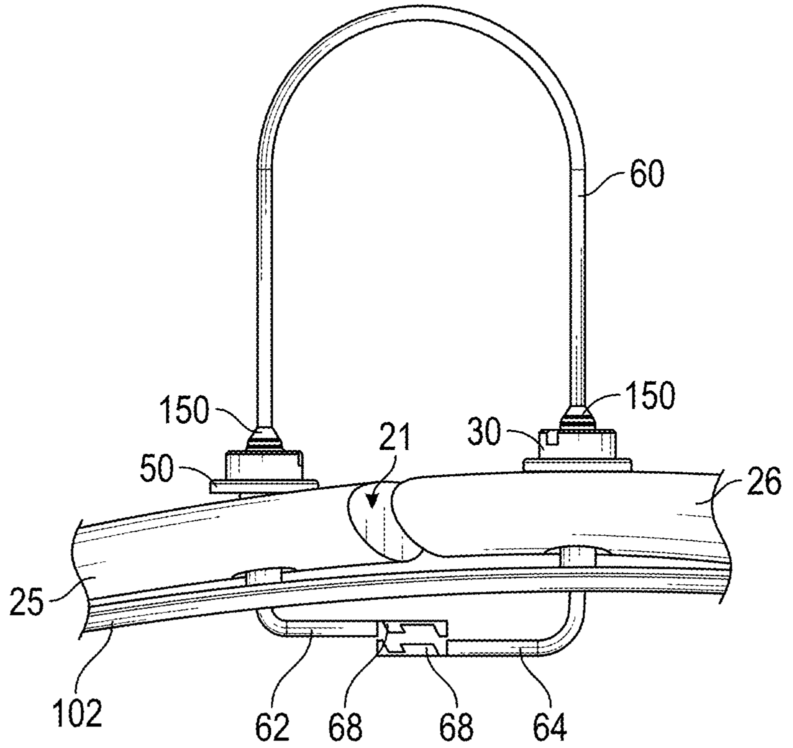
FIG. 51 is a bottom perspective view of a fracture plating system in a partially deployed configuration according to an embodiment of the present disclosure spanning an exemplary bone fracture.
Figure 52:
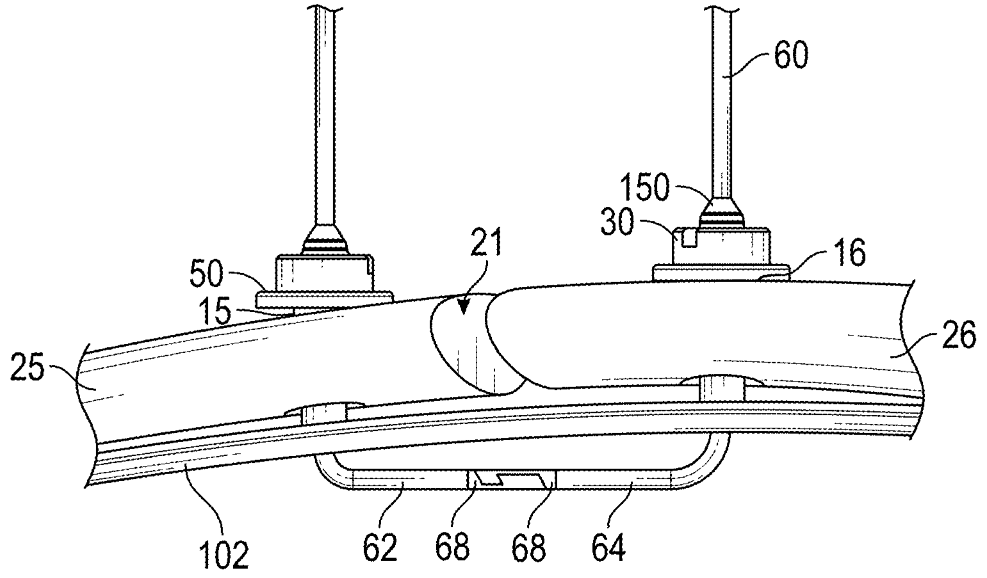
FIG. 52 is a partial bottom perspective view of the fracture plating system of FIG. 51 spanning an exemplary bone fracture.

FIG. 51 is a bottom perspective view of a fracture plating system in a partially deployed configuration according to an embodiment of the present disclosure spanning an exemplary bone fracture. FIG. 52 is a partial bottom perspective view of the fracture plating system of FIG. 51 spanning an exemplary bone fracture. A tether 60 may be configured so that a first tether end 62 may releasably connect to a second tether end 64. The tether 60 may fed through two fasteners and a plate in the opposite direction, i.e.: the first tether end 62 passing through a tip portion of a first fastener, the second tether end 64 passing through a tip portion of a second fastener, and the first tether end 62 releasably connecting to the second tether end 64 on the bottom side of the plate. The first tether end 62 and the second tether end 64 tether ends may then be releasably connected together to create a single continuous loop of tether. The first tether end 62 and the second tether end 64 may each include a connection feature 68.

A first hole 15 may be drilled in a first bone portion 25 and a second hole 16 may be drilled in a second bone portion 26. The first tether end 62 may be passed through the first hole 15 and the second tether end 64 may be passed through the second hole 16. The first tether end 62 and the second tether end 64 may then be grabbed with an endoscopic grasper and pulled out thru a VATS port. The first tether end 62 may then be passed through the first fastener and a first slot of a plate and the second tether end 64 may then be passed through the second fastener and a second slot of the plate. The first tether end 62 may then be connected to the second tether end 64 using the connection feature 68. Once the connection is made, the tether 60 may then be pulled to place the plate again the interior surface of a portion of bone.

Figure 53:
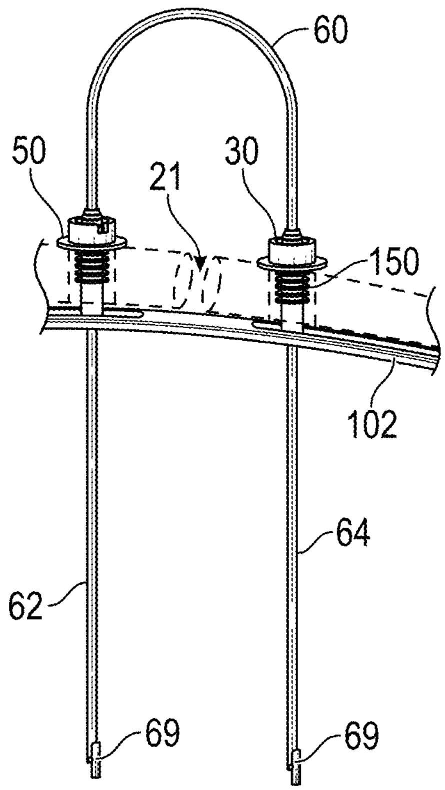
FIG. 53 is a front view of a fracture plating system in a partially deployed configuration according to an embodiment of the present disclosure spanning an exemplary bone fracture.
Figure 54:
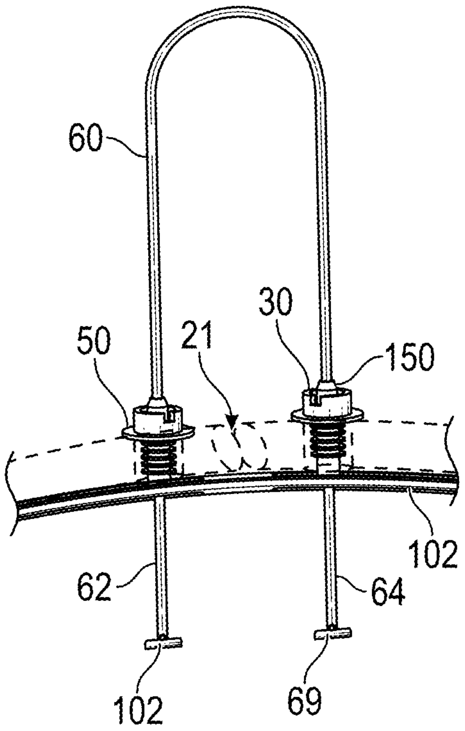
FIG. 54 is a partial front view of the fracture plating system of FIG. 53 spanning an exemplary bone fracture.
Figure 55:
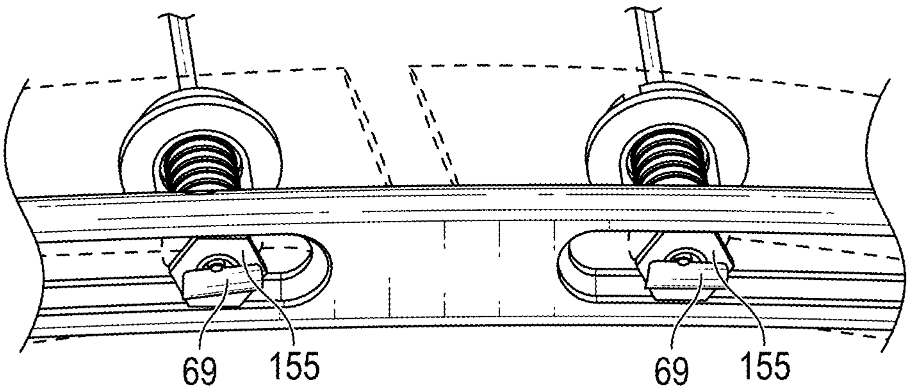
FIG. 55 is a partial bottom perspective view of the fracture plating system of FIG. 53 spanning an exemplary bone fracture.

FIG. 53 is a front view of a fracture plating system in a partially deployed configuration according to an embodiment of the present disclosure spanning an exemplary bone fracture. FIG. 54 is a partial front view of the fracture plating system of FIG. 53 spanning an exemplary bone fracture. FIG. 55 is a partial bottom perspective view of the fracture plating system of FIG. 53 spanning an exemplary bone fracture.

A tether 60 may be configured so that a first tether end 62 and a second tether end 64 may each include a toggle feature 69. The tether 60 may fed through two fasteners and a plate in the opposite direction, i.e.: the first tether end 62 passing through a tip portion of a first fastener, the second tether end 64 passing through a tip portion of a second fastener, a first toggle feature 69 may be deployed so that the first tether end 62 may not return through the first fastener, and a second toggle feature may be deployed so that the second tether end 64 may not return through the second fastener.

A first hole 15 may be drilled in a first bone portion 25 and a second hole 16 may be drilled in a second bone portion 26. The first tether end 62 may be passed through the first hole 15 and the second tether end 64 may be passed through the second hole 16. The first tether end 62 and the second tether end 64 may then be grabbed with an endoscopic grasper and pulled out thru a VATS port. The first tether end 62 may then be passed through the first fastener and a first slot of a plate and the second tether end 64 may then be passed through the second fastener and a second slot of the plate. The toggle feature 69 of the first tether end 62 and the toggle feature 69 of the second tether end 64 may then be deployed. The tether 60 may then then be pulled to place the plate again the interior surface of a portion of bone.

Figure 56:
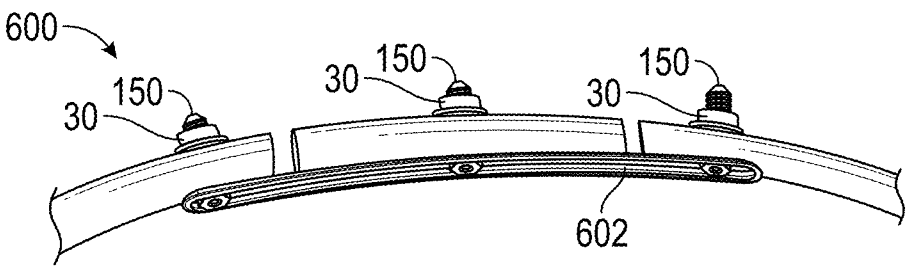
FIG. 56 is a front view of a fracture plating system according to an embodiment of the present disclosure spanning a plurality of exemplary bone fractures.
Figure 57:
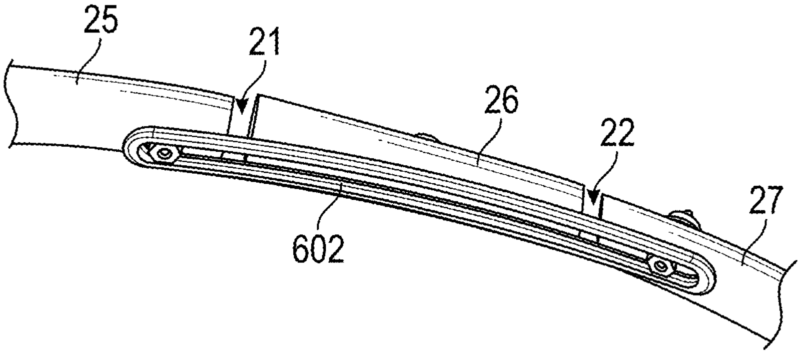
FIG. 57 is a bottom perspective view of the fracture plating system of FIG. 56 spanning a plurality of exemplary bone fractures.

FIG. 56 is a front view of a fracture plating system 600 according to an embodiment of the present disclosure spanning a plurality of exemplary bone fractures. FIG. 57 is a bottom perspective view of the fracture plating system 600 spanning a plurality of exemplary bone fractures. The fracture plating system 600 may include similar features as other fracture plating systems previously described within the present disclosure. The fracture plating system 600 may include a plate 602 and may include two or more of an anti-rotation fastener 150 and/or a circular head fastener 180.

Figure 58A:
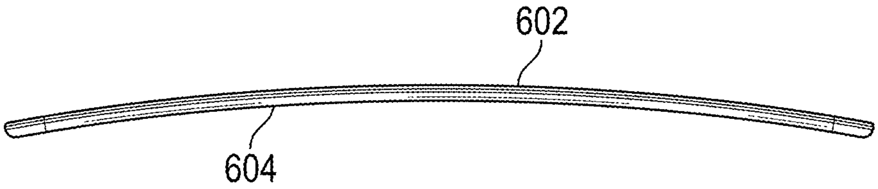
FIG. 58A is a front view of a plate of the fracture plating system of FIG. 56 according to an embodiment of the present disclosure.
Figure 58B:
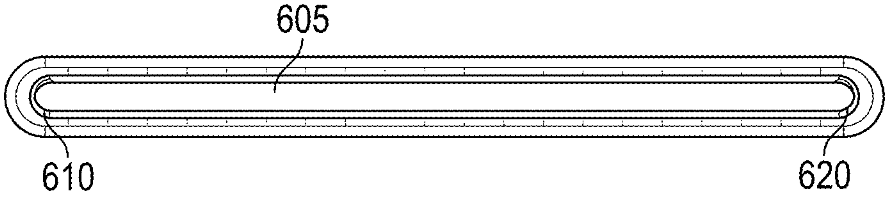
FIG. 58B is a bottom view of the plate of FIG. 58A.

FIG. 58A is a front view of a plate 602 of the fracture plating system 600 according to an embodiment of the present disclosure. FIG. 58B is a bottom view of the plate 602. The plate 602 may include a plate radius 604, a slot 605, a first threaded feature 610, and a second threaded feature 620. Alternatively, the plate 602 may include a plate radius 604, a slot 605, and a first threaded feature 610 whereby a plurality of fasteners may threadably engage the first threaded feature 610 to allow the plurality of fasteners to be slidably received within the slot 605.

The plate 602 may have one continuous slot 605 that allows the user to choose the number of fasteners to be added to the fracture plating system 600 and may allow for more intraoperative flexibility of where a fastener may be located relative to the plate 602 and relative to a fracture. The number of fasteners may be customized to each patient to match their individual facture pattern. Similar to fracture plating system previously described in the present disclosure, the fasteners may be connected to the plate 602 during a surgical procedure by threading the two or more fasteners through the first threaded feature 610 and/or the second threaded feature 620 of the plate 602. Multiple lengths of fasteners may be selected and attached to the plate 602 to match the thickness of the rib in that region. Additional points of fixation (a 3 or more fasteners as shown) may accommodate for variations in curvature and/or thickness of a portion of bone.

The plate 602 may be one of a set of differently-sized implants, each having a different plate length. A plate radius 604 may generally match a contour of an interior surface of a rib. The plate 602 may further be one of a set of differently-sized implants, each having a different plate radius 604.

Figure 59:
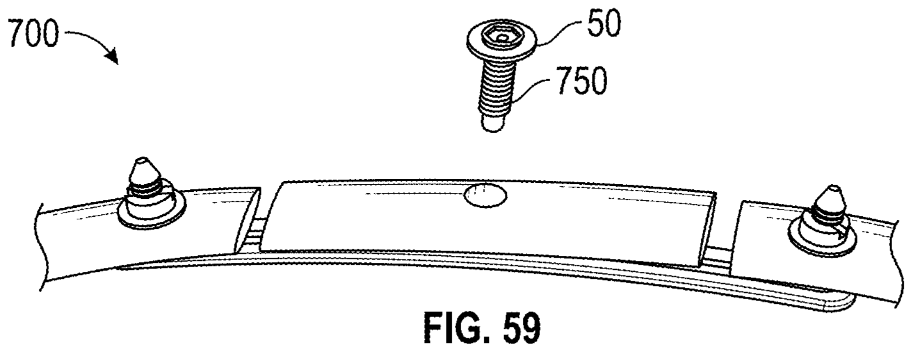
FIG. 59 is a perspective view of a fracture plating system according to an embodiment of the present disclosure spanning a plurality of exemplary bone fractures.
Figure 60:
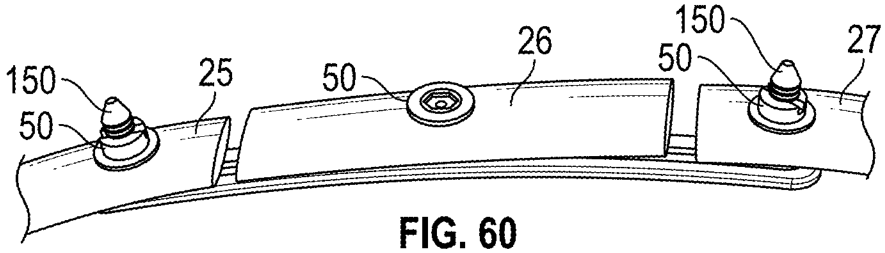
FIG. 60 is a perspective view of the fracture plating system of FIG. 59 spanning a plurality of exemplary bone fractures.

FIG. 59 is a perspective view of a fracture plating system 700 according to an embodiment of the present disclosure spanning a plurality of exemplary bone fractures. FIG. 60 is a perspective view of the fracture plating system 700 spanning a plurality of exemplary bone fractures. The fracture plating system 700 may include similar features as other fracture plating systems previously described within the present disclosure. The fracture plating system 700 may include a plate 702, a threaded fastener 750, and an anti-rotation fastener 150 and/or a circular head fastener 180. The fracture plating system 700 may allow a user to use a single plate 702 and a single tether 60 to stabilize two fractures in a single portion of bone.

Figure 61:
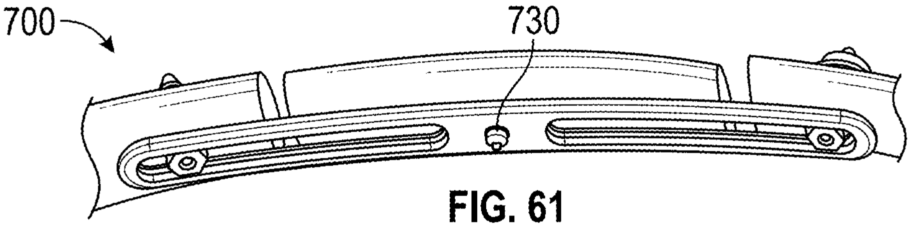
FIG. 61 is a bottom perspective view of the fracture plating system of FIG. 59 spanning a plurality of exemplary bone fractures.

FIG. 61 is a bottom perspective view of the fracture plating system 700 spanning a plurality of exemplary bone fractures. The plate 702 may be secured to a first bone portion 25 and a third portion 27 using components and methods previously described. The user may then drill a hole through the second bone portion 26 and through a central portion 725 of the plate 702 creating a central aperture 730 in the plate 702. A threaded fastener 750 may then be threadably inserted through the drilled hole and into central aperture 730 to secure the second bone portion to the plate 702.

Figure 62A:
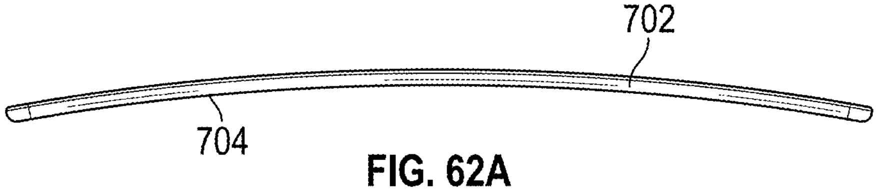
FIG. 62A is a front view of a plate of the fracture plating system of FIG. 59 according to an embodiment of the present disclosure.
Figure 62B:
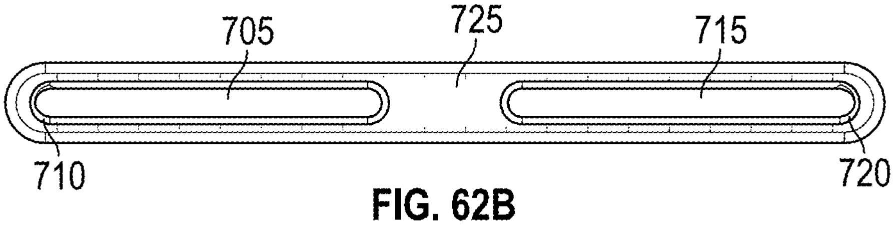
FIG. 62B is bottom view of the plate of FIG. 62A.

FIG. 62A is a front view of a plate 702 of the fracture plating system 700 according to an embodiment of the present disclosure. FIG. 62B is bottom view of the plate 702. The plate 702 may include a plate radius 704, a first slot 705, a second slot 715, and a central portion 725. The first slot 705 may include a first threaded feature 710 and the second slot 715 may include a second threaded feature 720. The central portion 725 may be generally in the center of the plate 702 and may separate the first slot 705 and the second slot 715.

The first threaded feature 710 may be configured to threadably engage a threaded portion 190 of a circular head fastener 180 and/or the threaded portion 160 of an anti-rotation fastener 150 to allow the threaded portion 190 and/or the threaded portion 160 to pass through the first slot 705. The second threaded feature 720 may be configured to threadably engage a threaded portion 190 of a circular head fastener 180 and/or the threaded portion 160 of an anti-rotation fastener 150 to allow the threaded portion 190 and/or the threaded portion 160 to pass through the second slot 715.

The plate 702 may be configured such that a plate length is within a range of lengths from 30 mm to 300 mm. The plate 702 may be one of a set of differently-sized implants, each having a different plate length. A plate radius 704 may generally match a contour of an interior surface of a rib. The plate 702 may further be one of a set of differently-sized implants, each having a different plate radius 704.

Figure 63A:
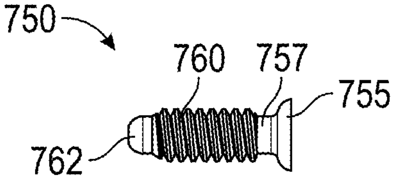
FIG. 63A is a front view of a threaded fastener of the fracture plating system of FIG. 59 according to an embodiment of the present disclosure.
Figure 63B:
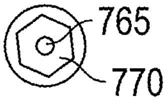
FIG. 63B is a side view of the threaded fastener of FIG. 63A.

FIG. 63A is a front view of a threaded fastener 750 of the fracture plating system 700 according to an embodiment of the present disclosure. FIG. 63B is a side view of the threaded fastener 750. The threaded fastener 750 may include a head portion 755, a shank portion 757, a threaded portion 760, a tip portion 762, a cannulation 765, and a drive portion 770.

The head portion 755 may include the drive portion 770. The drive portion may be configured to receive a driver instrument (not shown) configured to impart a torque to the threaded fastener 750. The drive portion 770 may be configured as a hex, a hexalobe, a square, a slot, or other drive geometry known in the art.

The cannulation 765 may be configured to receive a guide wire (not shown) to assist in placement location of the threaded fastener 750. The threaded portion 760 and the shank portion 757 may be configured to receive a washer 50. The tip portion 762 may be configured to guide the threaded fastener 750 into a hole drilled into a portion of bone. The threaded portion 760 may be configured to threadably engage the second bone portion 26 and the central aperture 730. Alternatively, a diameter of the hole drilled onto a portion bone may be larger than a thread diameter of the threaded fastener 750 and the threaded portion 760 may be configured to threadably engage the central aperture 730.

The threaded fastener 750 may be configured within a range of lengths from 5 mm to 20 mm and within a range of diameters from 3 mm to 8 mm. The threaded fastener 750 may be one of a set of differently-sized implants, each having a different length and/or diameter.

FIG. 64A front view of a toggle fastener 850 in an insertion configuration of a fracture plating system 800 according to an embodiment of the present disclosure. FIG. 64B is a front view of the toggle fastener 850 in a deployed configuration. The fracture plating system 800 may include similar features as other fracture plating systems previously described within the present disclosure. The fracture plating system 800 may include at least one toggle fastener 850, at least one locking nut 30 and a plate.

In an embodiment, at least one toggle fastener 850 may be inserted thru at least one hole in a bone. The at least one toggle fastener 850 may then be grabbed with an endoscopic grasper and pulled out a VATS port. The at least one toggle fastener 850 may then be inserted thru at least one slot in a properly configured plate and the at least one toggle fastener 850 may then be deployed to engage the plate. At least one tether 60 tethers may be pre-attached to a top of the toggle fastener. A user may pull the at least one tether 60 to tension the plate against the bone.

The toggle fastener 850 may include a head portion 855, a shank portion 857, a threaded portion 860, a tip portion 862, at least one toggle 880, and a pin 890. The head portion 855 may be configured to guide a washer 50 and/or a locking nut 30 onto the toggle fastener 850. The shank portion 857 may be configured to receive at least on toggle 880 when the at least one toggle is in an insertion configuration. The threaded portion 860 may be configured to threadably reactive a locking nut 30. The pin may be configured to rotatably secure at least one toggle 880 to the shank portion 857. The at least one toggle 880 may be configured so that, in a deployed configuration, the at least one toggle 880 extends beyond the threaded portion 860.

FIG. 65 is a perspective view of a pair of toggle fasteners 850 in a partially deployed configuration spanning an exemplary bone fracture. FIG. 66 is a perspective view of a pair of toggle fasteners 850 in a partially deployed configuration spanning an exemplary bone fracture. FIG. 67 is a perspective view of a pair of toggle fasteners 850 in a partially deployed configuration spanning an exemplary bone fracture. A first hole 15 may be drilled in a first bone portion 25 and a second hole 16 may be drilled in a second bone portion 26.

FIG. 68 is a perspective view of a pair of toggle fasteners 850 in a partially deployed configuration spanning an exemplary bone fracture. The toggle fastener 850 may include an insertion configuration in which a first toggle 880 and a second toggle 880 may be aligned generally parallel with a long axis of the toggle fastener 850. The toggle fastener 850 may include a deployed configuration in which a first toggle 880 and a second toggle 880 may be generally perpendicular to a long axis of the toggle fastener 850.

FIG. 69 is a perspective view of a fracture plating system 800 including the toggle fastener 850 according to an embodiment of the present disclosure spanning an exemplary bone fracture. A first toggle fastener 850, in an insertion configuration, may be inserted through the first hole, until the first toggle 880 and the second toggle 880 are past the inner surface of the bone. The first toggle fastener 850 may then translate from the insertion configuration to the deployed configuration and the toggle fastener 850 may be drawn upward and the toggle fastener 850 contacts the inside surface of the bone.

FIG. 70 is a bottom perspective view of the fracture plating system 800 spanning an exemplary bone fracture. The steps may be repeated for a second toggle fastener 850 being inserted into a second hole 16. The first toggle fastener 850 and the second toggle fastener 850 may be urged towards each other to reduce the facture.

FIG. 71 is a bottom view of the plate 102. A plate 102 may be applied to the tops of the first toggle fastener 850 and the second toggle fastener 850 fastener to provide rigid fixation that bridges the gap of the fracture. A washer 50 a locking nut 30 may be secured to each of the first toggle fastener 850 and the second toggle fastener 850 to tighten the construct in place.

FIG. 72 is a perspective view of a fracture plating system 900 according to an embodiment of the present disclosure in a partially assembled configuration. FIG. 73 is a perspective view of the fracture plating system 900 in a partially assembled configuration. The fracture plating system 900 may include similar features as other fracture plating systems previously described within the present disclosure.

The fracture plating system 900 may include a post fastener 950, a locking nut 30, and one of any of the plates previously described, for example, plate 102. The post fastener 950 may be received in a first slot 105 and/or a second slot 115 of the plate 102. A nut 970 may then be threadably engaged with a second threaded portion 955 of the post fastener 950 to hold the post fastener 950 captively received within the plate 102 while still allowing translation of the post fastener 950 along a longitudinal axis of a first slot 105 and/or a second slot 115.

FIG. 74A is a front view of a post fastener 950 of the fracture plating system 900 according to an embodiment of the present disclosure. FIG. 74B is a side view of the post fastener 950. The post fastener 950 may include a first threaded portion 960, a second threaded portion 955, a shank portion 957, a tip portion 962, and a cannulation 965.

The shank portion 957 may be smaller than a width of the first slot 105 and/or the second slot 115 to allow the post fastener 950 to translate along the length of the first slot 105 and/or the second slot 115. The tip portion 962 may be configured to ease insertion of the post fastener 950 into a hole in a bone portion. The cannulation 965 may be configured to slidably receive a tether 60. The first threaded portion 960 may be configured to threadably receive a locking nut 30. The second threaded portion 955 may be configured to receive a nut 970.

FIG. 75A is a front view of a nut 970 of the fracture plating system 900 according to an embodiment of the present disclosure. FIG. 75B is a side view of the nut 970 and FIG. 75C is a perspective view of the nut 970. The nut 970 may include a third threaded portion 975, a height 980, and an outer portion 985. The third threaded portion 975 may be configured to threadably engage the second threaded portion 955 to capture the post fastener 950 within the first slot 105 and/or the second slot 115 of the plate 102 while still allowing translation of the post fastener 950 along the first slot 105 and/or the second slot 115.

The height 980 may be configured to maximize threaded engagement between the second threaded portion 955 and the third threaded portion 975. The outer portion 985 may be configured as a not circular geometry to prevent rotation of the nut 970 when the nut 970 is received within the first slot 105 and/or the second slot 115.

FIG. 76A is top view of a pin fastener 1050 of a fracture plating system 1000 according to an embodiment of the present disclosure. FIG. 76B is a perspective view of the pin fastener 1050, FIG. 76C is a front view of the pin fastener 1050, and FIG. 76D is a side view of the pin fastener 1050.

The fracture plating system 1000 may include similar features as other fracture plating systems previously described within the present disclosure. The fracture plating system 1000 may include a pin fastener 1050. The pin fastener 1050 may be configured to translate along a length of a first slot 1005 and/or a second slot 1015 in a plate 1002 to facilitate compression of a fracture. The fracture plating system 1000 may include a first pin fastener 1050 and a second pin fastener 1050 that each may translate within the first slot 1005 and/or the second slot 1015 of the plate 1002.

The pin fastener 1050 may include a head portion 1053, a threaded portion 1060, a tip portion 1062, and a cannulation 1065. The head portion 1053 may include at least one pin portion 1055. The head portion 1053 may be configured to be received within the first slot 1005 and/or the second slot 1015. The head portion 1053 may have a non-circular profile so that, when the head portion 1053 is received within the first slot 1005 and/or the second slot 1015, the pin fastener 1050 is prevented form rotating around the long axis of the pin fastener 1050, specifically when a locking nut 30 is threadably engaging the threaded portion 1060.

The pin portion 1055 may be configured to be received within a first groove 1012 and/or a second groove 1022 of the plate 1002. The pin portion 1055 may have a generally circular profile so that the pin fastener 1050 may translate along the length of the first slot 1005 and/or the second slot 1015 and the pin fastener 1050 may rotate about a long axis of the pin portion 1055.

The tip portion 1062 may be configured to ease insertion of the pin fastener 1050 into a hole in a bone portion. The cannulation 1065 may be configured to slidably receive a tether 60. The threaded portion 1060 may be configured to threadably receive a locking nut 30.

The pin fastener 1050 may be configured within a range of lengths from 5 mm to 30 mm and within a range of diameters from 3 mm to 8 mm. The pin fastener 1050 may be one of a set of differently-sized implants, each having a different length and/or diameter.

FIG. 77A is a top view of a plate 1002 of the fracture plating system 1000 according to an embodiment of the present disclosure. FIG. 77B is a front view of the plate 1002. The plate 1002 may include a plate radius 1004, a first slot 1005, a second slot 1015, and a central portion 1025. The first slot 1005 may include a first pocket 1010 and a first groove 1012. The second slot may include a second pocket 1020 and a second groove 1022.

FIG. 78 is a partial top view of the fracture plating system 1000 in a partially assembled configuration. FIG. 79 is a partial perspective view of the fracture plating system 1000 in a partially assembled configuration. FIG. 80 is a perspective section view of the fracture plating system 1000. The central portion 1025 may be generally in the center of the plate 1002 and may separate the first slot 1005 and the second slot 1015.

FIG. 81 is a perspective view of a fracture plating system 1000 according to an embodiment of the present disclosure. FIG. 82 is a partial perspective view of the fracture plating system 1000. FIG. 83 is a partial perspective view of the fracture plating system 1000.

The first pocket 1010 may be configured to receive the head portion 1053 and the pin portion 1055 of the pin fastener 1050. After the pin portion 1055 is received within the first pocket 1010, the pin portion 1055 may be slidably received into the first groove 1012. The second pocket 1020 may be configured to receive the head portion 1053 and the pin portion 1055 of the pin fastener 1050. After the pin portion 1055 is received within the second pocket 1020, the pin portion 1055 may be slidably received into the second groove 1022.

The plate 1002 may be one of a set of differently-sized implants, each having a different plate length. A plate radius 1004 may generally match a contour of an interior surface of a rib. The plate 1002 may further be one of a set of differently-sized implants, each having a different plate radius 1004.

FIG. 102 is a perspective view of a fracture plating system 1100 according to an embodiment of the present disclosure spanning an exemplary bone fracture. FIG. 103 is a perspective view of a fracture plating system 1100. The fracture plating system 900 may include similar features as other fracture plating systems previously described within the present disclosure.

The fracture plating system 1100 may include an anti-rotation fastener 1150, a locking nut 1170, and one of any of the plates previously described, for example, plate 102. The anti-rotation fastener 1150 may be received in a first slot 105 and/or a second slot 115 of the plate 102. A locking nut 1170 may then be threadably engaged with a threaded portion 1160 of the anti-rotation fastener 1150 to hold the anti-rotation fastener 1150 captively received within the plate 102 while still allowing translation of the anti-rotation fastener 1150 along a longitudinal axis of the first slot 105 and/or a second slot 115. The anti-rotation fastener 1150 may include a head portion 1155, a shank portion 1157, a threaded portion 1160, a tip portion 1162, a cannulation 1165, and a rounded edge 1168.

FIG. 104A is a front view of an anti-rotation fastener 1150 of the fracture plating system 1100 according to an embodiment of the present disclosure. FIG. 104B is a side view of the anti-rotation fastener 1150. The head portion 1155 may be configured to be received within the first slot 105 and/or the second slot 115. The threaded portion 1160 may be larger than a width of the first slot 105 and/or the second slot 115 to prevent the anti-rotation fastener 1150 from disengaging from the plate 102.

The shank portion 1157 may be smaller than a width of the first slot 105 and/or the second slot 115 to allow the anti-rotation fastener 1150 to translate along the length of the first slot 105 and/or the second slot 115. The tip portion 1162 may be configured to ease insertion of the anti-rotation fastener 1150 into a hole in a bone portion. The cannulation 1165 may be configured to slidably receive a tether 60. The threaded portion 1160 may be configured to threadably receive a locking nut 1170. The rounded edge 1168 may reduce stress on the tether 60 when the tether 60 exerts a force on the anti-rotation fastener 1150.

The anti-rotation fastener 1150 may be configured within a range of lengths from 5 mm to 30 mm and within a range of diameters from 2 mm to 8 mm. The anti-rotation fastener 1150 may be one of a set of differently-sized implants, each having a different length and/or diameter.

FIG. 105A is a front view of a locking nut 1170 of the fracture plating system 1100 according to an embodiment of the present disclosure. FIG. 105B is a side view of the locking nut 1170. The locking nut 1170 may be configured to threadably engage the anti-rotation fastener 1150 to secure the plate 102 to a portion of a rib.

The locking nut 1170 may include a threaded portion 1172, a body 1174, a body diameter 1176, a head profile 1178, and a body length 1180. The threaded portion 1172 may be configured to threadably engage the threaded portion 1160 of the anti-rotation fastener 1150. The head profile 1178 may allow engagement of a driver 1200 to threadably engage the locking nut 1170 with the anti-rotation fastener 1150. The head profile 1178 may be configured as a hex, a square, or other non-circular geometry.

The body diameter 1176 may be configured to be received in a hole drilled into a portion of bone. The body length 1180 may be configured to be less than a thickness of a portion of the bone.

FIG. 106A is a perspective view of a driver 1200 of the fracture plating system 1100 according to an embodiment of the present disclosure. FIG. 106B is a side view of the driver 1200 and FIG. 106C is a front view of the driver 1200. The driver 1200 may be configured to engage a locking nut 1170 and may transfer torque from a handle (not shown) to the locking nut 1170 thereby threadably securing the locking nut 1170 to an anti-rotation fastener 1150.

The driver 1200 may include a quick connect feature 1210, a head portion 1260, and a shaft configured to connect the quick connect feature 1210 and the head portion 1260. The shaft 1220 may include a cannulation 1250. The head portion 1260 may include a socket portion 1230 that may include a drive portion 1240. The cannulation 1250 may be configured to receive a guide wire (not shown) to assist in alignment of the driver 1200 with the anti-rotation fastener 1150.

The quick connect feature 1210 may be configured to be removably received by a handle (not shown) having a compatible quick connect feature. The quick connect feature 1210 may be configured as one of: AO connector, Hudson connector, trilobe connector, square connector, hex connector, Stryker connector, Stryker-Hall connector, or other quick connect mechanism known in the art.

The socket portion 1230 may be configured to receive the head profile 1178 of the locking nut 1170. The drive portion 1240 may be configured to engage the head profile 1178 and may be configured as a hex, a double hex, a square or other non-circular geometry that may engage the head profile 1178 of the locking nut 1170 in order to transfer torque from the driver 1200 to the locking nut 1170.

FIG. 107 is a front perspective view of a spinal fixation plating system 1300, secured to an exemplary portion of a spine, according to an embodiment of the present disclosure. The spinal fixation plating system 1300 may include a plate 1302, an anti-rotation fastener 1350, and a locking nut 1370. The plate 1302 may span an intervertebral space 14 and may be secured to a first vertebra 10 and a second vertebra 12.

The spinal fixation plating system 1300 may be configured to provide immobilization and stabilization of spinal segments. The spinal fixation plating system 1300 may be used as an adjunct to fusion in the treatment of the cervical, thoracic, lumbar, and/or sacral spine. Additionally, or alternatively, the spinal fixation plating system 1300 may be used in conjunction with other devices to support fusion of one or more spinal segments. The spinal fixation plating system 1300 may be implanted through an interior approach (ALIF), a posterior transforaminal approach (TLIF), a lateral approach (DLIF/XLIF), and/or an oblique approach (OLIF).

One or more spinal fixation plating system 1300 constructs may be used on a single spinal segment. The one or more spinal fixation plating system 1300 constructs may be implanted on opposite side of the spinal column. Additionally, or alternatively, a single spinal fixation plating system 1300 construct may span one or more spinal segments. Additionally, or alternatively, one or more spinal fixation plating system 1300 constructs may be configured to prevent expulsion and/or subsidence of one or more intervertebral implants. Additionally, or alternatively, the spinal fixation plating system 1300 may be configured to be implanted as an adjunct to a posterior rod/pedicle screw construct.

FIG. 108 is a rear perspective view of the spinal fixation plating system 1300 secured to an exemplary portion of a spine. Similar to the fracture plating systems previously described, the spinal fixation system may be configured to be deployed using a single tether 60 to pull the plate against the first vertebra 10 and the second vertebra 12. The tether 60 may be used to guide a first anti-rotation fastener 1350 through a hole in the first vertebra 10 and a second anti-rotation fastener 1350 through a hole in the second vertebra 12. A first locking nut 1370 may be guided along a first tether end 62 to threadably engage the first anti-rotation fastener 1350. A second locking nut 1370 may be guided along a second tether end 64 to threadably engage the second anti-rotation fastener 1350.

FIG. 109 is a front perspective view of the spinal fixation plating system 1300 secured to an exemplary portion of a spine. FIG. 110 is a rear perspective view of the spinal fixation plating system 1300 secured to an exemplary portion of a spine. After the first locking nut 1370 threadably engages the first anti-rotation fastener 1350 and the second locking nut 1370 threadably engages the second anti-rotation fastener, the tether 60 may be removed.

FIG. 111A is a front view of a plate 1302 of the spinal fixation plating system 1300 according to an embodiment of the present disclosure. FIG. 111B is a bottom view of the plate 1302. The plate 1302 may include a plate length 1303 and a plate radius 1304. The plate length 1303 may be configured to span one or more spinal segments.

The plate 1302 may be configured such that the plate length 1303 is within a range of lengths from 30 mm to 300 mm. The plate 1302 may be one of a set of differently-sized implants, each having a different plate length 1303. The plate radius 1304 may generally match a contour of a lateral and/or anterior portion of a vertebra. The plate 1302 may further be one of a set of differently-sized implants, each having a different plate radius 1304.

The plate 1302 may further include a central portion 1325 and a first slot 1305 having a first slot width 1307 and a first threaded feature 1310. The plate 1302 may also include a second slot 1315 having a second slot width 1317 and a second threaded feature 1320. The central portion 1325 may be generally in the center of the plate 1302 and may separate the first slot 1305 and the second slot 1315.

The first slot width 1307 and the second slot width 1317 may each be configured to receive an anti-rotation fastener 1350. The first slot width 1307 and the second slot width 1317 may further be configured to allow translation of the anti-rotation fastener 1350 along the length of the first slot 1305 and the second slot 1315 respectively.

FIG. 112A is a perspective view of a locking nut 1370 of the spinal fixation plating system 1300 according to an embodiment of the present disclosure. FIG. 112B is a front view of the locking nut 1370 and FIG. 112C is a side view of the locking nut 1370. The locking nut 1370 may be configured to threadably engage the anti-rotation fastener 1350 to secure the plate 1302 to a vertebra.

The locking nut 1370 may include a threaded portion 1372, a body 1374, a body diameter 1376, a head profile 1378, and a body length 1380. The threaded portion 1372 may be configured to threadably engage the threaded portion 1360 of the anti-rotation fastener 1350. The head profile 1378 may allow engagement of a driver 1200 to threadably engage the locking nut 1370 with the anti-rotation fastener 1350. The head profile 1378 may be configured as a hex, a square, or other non-circular geometry.

The body diameter 1376 may be configured to be received in a hole drilled into a vertebra. The body length 1380 may be configured to be less than a thickness of a vertebra.

FIG. 113A is a perspective view of an anti-rotation fastener 1350 of the spinal fixation plating system 1300 according to an embodiment of the present disclosure. FIG. 113B is a front view of the anti-rotation fastener 1350 and FIG. 113C is a side view of the anti-rotation fastener 1350. The anti-rotation fastener 1350 may include a head portion 1355, a shank portion 1357, a threaded portion 1360, a tip portion 1362, a cannulation 1365, and a rounded edge 1368.

The anti-rotation fastener 1350 may be configured to secure the plate 1302 to a vertebra. The anti-rotation fastener 1350 may also be configured to be captively received within the plate 1302 while still being allow to translate along a longitudinal axis of the first slot 1305 and/or the second slot 1315. The anti-rotation fastener 1350 may be configured so that, when a head portion 1355 engages the first slot 1305 and/or the second slot 1315, the anti-rotation fastener 1350 is prevented from rotating in relation to the plate 1302.

The head portion 1355 may be configured to be received within the first slot 1305 and/or the second slot 1315. The threaded portion 1360 may be larger than a width of the first slot 1305 and/or the second slot 1315 to prevent the anti-rotation fastener 1350 from disengaging from the plate 1302. The first threaded feature 1310 and the second threaded feature 1320 may each be configured to threadably engage the threaded portion 1360 to allow the threaded portion 1360 to pass through the first slot 1305 and the second slot 1315 respectively.

The shank portion 1357 may be smaller than a width of the first slot 1305 and/or the second slot 1315 to allow the anti-rotation fastener 1350 to translate along the length of the first slot 1305 and/or the second slot 1315 respectively. The tip portion 1362 may be configured to ease insertion of the anti-rotation fastener 1350 into a hole in a vertebra. The cannulation 1365 may be configured to slidably receive a tether 60. The rounded edge 1368 may reduce stress on the tether 60 when the tether 60 exerts a force on the anti-rotation fastener 1350.

FIG. 114 is a front view of a fracture plating system 1400 according to an embodiment of the present disclosure spanning an exemplary bone fracture. FIG. 115 is a partial perspective view of the fracture plating system 1400. FIG. 116 is a partial section view of the fracture plating system 1400. FIG. 117 is a front section view of the fracture plating system 1400.

The fracture plating system 1400 may include similar features as other fracture plating systems previously described within the present disclosure. The fracture plating system 1400 may include a ratchet fastener 1450, a ratchet cap 1470, and one of any of the plates previously described, for example, plate 102.

The ratchet fastener 1450 may be received in a first slot 105 and/or a second slot 115 of the plate 102. A ratchet cap 1470 may then be engaged with a ratchet portion 1460 of the ratchet fastener 1450 to hold the ratchet fastener 1450 captively received within the plate 102 while still allowing translation of the ratchet fastener 1450 along a longitudinal axis of a first slot 105 and/or a second slot 115.

FIG. 118A is a bottom perspective view of a ratchet cap 1470 of the fracture plating system 1400 according to an embodiment of the present disclosure. FIG. 118B is front perspective view of the ratchet cap 1470, FIG. 118C is a front view of the ratchet cap 1470, and FIG. 118D is a side view of the ratchet cap 1470. The ratchet portion 1472 may be configured to engage the ratchet portion 1460 of the ratchet fastener 1450 to secure the plate 102 to a portion of a rib.

The ratchet cap 1470 may include a ratchet portion 1472, a body 1474, a body diameter 1476, a head diameter 1478, a body length 1480, and one or more slots 1485. The ratchet portion 1472 may be configured to engage the ratchet portion 1460 of the ratchet fastener 1450. The body diameter 1476 may be configured to be received in a hole drilled into a portion of bone. The body length 1480 may be configured to be less than a thickness of a portion of the bone.

The head diameter 1478 may be configured to be larger than a hole drilled into a portion of bone. The ratchet portion 1472 may include a plurality of grooves. Each of the plurality of grooves may have a leading angle 1481 and a trailing angle 1482. The leading angle 1481 may be within a range of 15° to 45°. More specifically, the leading angle 1481 may be within a range of 20° to 40°. More specifically, the leading angle 1481 may be 30°. The trailing angle 1482 may be generally perpendicular to a long axis of the body 1474. The one or more slots 1485 may be configured to allow the body diameter 1476 to temporarily increase as the ratchet portion 1472 of the ratchet cap 1470 engages and the ratchet portion 1460 of the ratchet fastener 1450.

FIG. 119A is a perspective view of a ratchet fastener 1450 of the fracture plating system 1400 according to an embodiment of the present disclosure. FIG. 119B is a front view of the ratchet fastener 1450 and FIG. 119C is a side view of the ratchet fastener 1450. The ratchet fastener 1450 may include a head portion 1455, a shank portion 1457, a ratchet portion 1460, a tip portion 1462, a cannulation 1465, and a rounded edge 1468. The head portion 1455 may be configured to be received within the first slot 105 and/or the second slot 115. The ratchet portion 1460 may be larger than a width of the first slot 105 and/or the second slot 115 to prevent the ratchet fastener 1450 from disengaging from the plate 102.

The shank portion 1457 may be smaller than a width of the first slot 105 and/or the second slot 115 to allow the ratchet fastener 1450 to translate along the length of the first slot 105 and/or the second slot 115. The tip portion 1462 may be configured to ease insertion of the ratchet fastener 1450 into a hole in a bone portion. The cannulation 1465 may be configured to slidably receive a tether 60. The ratchet portion 1460 may be configured to receive a ratchet cap 1470. The rounded edge 1468 may reduce stress on the tether 60 when the tether 60 exerts a force on the ratchet fastener 1450.

The ratchet portion 1460 may include a plurality of grooves. Each of the plurality of grooves may have a leading angle 1458 and a trailing angle 1459. The leading angle 1458 may be within a range of 15° to 45°. More specifically, the leading angle 1458 may be within a range of 20° to 40°. More specifically, the leading angle 1458 may be 30°. The trailing angle 1459 may be generally perpendicular to a long axis of the shank portion 1457.

The ratchet fastener 1450 may be configured within a range of lengths from 5 mm to 30 mm and within a range of diameters from 3 mm to 8 mm. The ratchet fastener 1450 may be one of a set of differently-sized implants, each having a different length and/or diameter. The ratchet cap 1470 may be one of a set of differently-sized implants, each having a different diameter configured to engage each of the differently sized ratchet fasteners 1450.

The ratchet fastener 1450 may be configured to receive the ratchet cap 1470 so that the ratchet portion 1460 of the ratchet fastener 1450 engages the ratchet portion 1472 of the ratchet cap 1470. More specifically, the leading angle 1481 of the ratchet cap 1470 and the leading angle 1458 of the ratchet fastener 1450 may be configured to allow the ratchet cap 1470 to advance along a length of the ratchet fastener 1450 from the tip portion 1462 towards the head portion 1455.

Moreover, the trailing angle 1482 of the ratchet cap 1470 and the trailing angle of the ratchet fastener 1450 may be configured to prevent translation of the ratchet cap 1470 along a length of the ratchet fastener 1450 from the head portion 1455 towards the tip portion 1462.

The ratchet cap 1470 may create compression at the interface similar to the locking nut 1370, but the advantage may be that it the ratchet cap 1470 may not require a drive feature to install the ratchet cap 1470 and secure the construct. The drive feature on the previous concepts may require the cap to have some thickness to engage with. The ratchet cap 1470 may not require a non-circular drive feature to apply torque. Thus, the ratchet cap 1470 may be much thinner than the locking nut 1370. A thinner cap may result in a lower profile construct on the bone and thus may reduce irritation of the surrounding soft tissues.

FIG. 120A is a perspective view of a fracture repair system 1500 in an undeformed configuration 1520 according to an embodiment of the present disclosure. FIG. 120B is a front view of the fracture repair system 1500 in an undeformed configuration 1520. FIG. 120C is a side view of the fracture repair system 1500 in an undeformed configuration 1520. The fracture repair system 1500 may be configured as a staple.

The fracture repair system 1500 may be configured to span a fracture in a portion of a bone. The fracture repair system 1500 may further be configured to provide compression of the fracture after implantation.

The fracture repair system 1500 may include a bridge portion 1550, a first leg 1555 having a first tip 1557, a second leg 1560 having a second tip 1562, a plurality of retaining features 1570, and a bridge apex 1580. The bridge portion 1550 may connect the first leg 1555 and the second leg 1560. Each of the first leg 1555 and the second leg 1560 may include a plurality of retaining features 1570. The plurality of retaining features 1570 may be configured to inhibit subsidence or back-out of the fracture repair system 1500 from a bone portion after implantation.

The first tip 1557 and the second tip 1562 may each be configured with a sharp point configured to penetrate a portion of bone. The fracture repair system 1500 may be configured to be embedded directly into a portion of bone. Additionally, or alternatively, the fracture repair system 1500 may be configured to be embedded into one or more apertures in a portion of bone and/or a portion of cartilage.

The fracture repair system 1500 may be fabricated from NITINOL, titanium, titanium alloy, stainless steel, cobalt-chrome, PEEK, PEAK, UHMWPE, a resorbable polymer, or any other biocompatible material with sufficient tensile strength and shape memory properties.

The fracture repair system 1500 may include an undeformed configuration 1520 and an expanded configuration 1540. FIG. 121 is a front view of the fracture repair system 1500 in an undeformed configuration 1520. The FIG. 122 is a front view of the fracture repair system 1500 in an expanded configuration 1540 according to an embodiment of the present disclosure.

In the undeformed configuration 1520 the bridge portion 1550 may include a bridge apex 1580. The bridge apex 1580 may be centrally located along the bridge portion 1550. In the undeformed configuration 1520 the fracture repair system 1500 may include a first leg spacing 1590. In the expanded configuration 1540 the fracture repair system 1500 may include a second leg spacing 1592. The first leg spacing 1590 may be less than the second leg spacing 1592.

The fracture repair system 1500 may be configured so that an external force is required to transition from the undeformed configuration 1520 to the expanded configuration 1540. Additionally, when the external force is removed, the fracture repair system 1500 will return from the expanded configuration 1540 to the undeformed configuration 1520 with no other externally applied forces.

An instrument/tool (not shown) may be used to elastically deform the fracture repair system 1500 from the undeformed configuration 1520 to the expanded configuration 1540. Once inserted into the tissue (bone and/or cartilage) the force of the instrument may be removed and the fracture repair system 1500 may return to the undeformed configuration 1520. The fracture repair system 1500 may be inserted to bridge a rib fracture in the expanded configuration 1540, and then may be used to compress the fractured bones back together as it moves back towards the undeformed configuration 1520.

FIG. 123 is a front section view of an exemplary rib cage with the fracture repair system 1500 spanning exemplary fractures. FIG. 124 is a front section view of an exemplary rib cage with the fracture repair system 1500 compressing exemplary fractures. FIG. 125 is a front section view of an exemplary rib cage with the fracture repair system 1500 compressing exemplary fractures. The fracture repair system 1500 may be utilized to bridge fractures in ribs, in the costal cartilage, between sternum-to-costal cartilage, rib-to-costal cartilage, bone-to-cartilage, bone-to-bone, and/or cartilage-to-cartilage. One or more of the fracture repair systems 1500 may be applied to a single fracture and may provide additional stabilization and/or additional compression.

A fracture repair system 1600 may include a balloon 1610, cement, and an application instrument 1620. Human rib bones are generally hollow, similar to long bones, and may have an intramedullary canal. The balloon 1610 may be configured for repairing a fracture of any bone having an intramedullary canal. The balloon 1610 may be configured to be inserted into an intramedullary canal and span a fracture from an inside of a portion of bone. The balloon 1610 may then be filled with a bone cement 1650 know in the orthopedic arts. After a period of time and/or application of a hardening agent the bone cement 1650 may harden. The hardened bone cement 1650 and balloon may stabilize the fracture.

FIG. 126A is a perspective view of an application instrument 1620 of a fracture repair system 1600 according to an embodiment of the present disclosure. FIG. 126B is a side view of the application instrument 1620 and FIG. 126C is a front view of the application instrument 1620. The application instrument may include a funnel 1622, a shank 1625, an aperture 1630, and an end portion 1635.

The shank 1625 may be hollow and may connect the funnel 1622 with the aperture 1630. The funnel 1622 may be configured to ease insertion of the balloon 1610 and/or bone cement 1650. The end portion 1635 may be configured to prevent discharge from the shank 1625 through the end portion 1635. The application instrument 1620 may be configured so that the balloon 1610 and/or the bone cement 1650 may be introduced into the funnel, travel through the interior of the shank 1625 and exit through the aperture 1630. The aperture 1630 may be configured so that the balloon 1610 and/or the bone cement 1650 exit at a generally right angle with respect to an axis of the shank 1625.

FIG. 127 is a balloon 1610 of the fracture repair system 1600 according to an embodiment of the present disclosure.

The balloon 1610 may be configured to be deployed through the application instrument 1620 into an intramedullary canal of a bone portion. The balloon 1610 may include an opening 1612 and a body 1614. The opening 1612 may be sized generally the same as, or slightly larger than, the aperture 1630 to facilitate introduction of bone cement 1650 through the aperture into the interior of the balloon 1610. The circumference of the balloon 1610 may be generally equal to or larger than the circumference of the intramedullary canal of the fractured bone portion.

The body 1614 may be configured to receive bone cement 1650 through the opening 1612 and expand upon introduction of the bone cement 1650. The balloon 1610 may be configured within a range of outer profiles from 8 mm to 25 mm and within a range of lengths from 5 mm to 500 mm. The balloon 1610 may be one of a set of differently-sized implants, each having a different outer profile and/or length. The balloon 1610 may be impregnated with barium sulfate or similar contrast agent. The outer profile may be generally equal to an outside perimeter of the balloon 1610. In one embodiment, the balloon 1610 may be circular in cross-section and the outer profile may equal the circumference of the cross-section.

A method for stabilizing one or more fractures of a portion of bone may include using a balloon 1610 and bone cement 1650. A method for stabilizing one or more fractures of a portion of bone may include the following steps:

FIG. 128 is a partial perspective view of an exemplary rib cage 20 with an exemplary bone first fracture 21.

Step 1 may include finding a fracture 21 using ultrasound or other radiographic means.

FIG. 129 is a partial perspective view of the exemplary rib cage 20 illustrating a step in a method of deploying a fracture repair system 1600 according to an embodiment of the present disclosure.

Step 2 may include drilling a first hole 15 through the proximal cortex of the bone portion adjacent to the first fracture 21.

FIG. 130 is a partial perspective view of the exemplary rib cage 20 illustrating a step in a method of deploying a fracture repair system 1600 according to an embodiment of the present disclosure.

Step 3 may include inserting the application instrument 1620 into the hole 15 and orienting the aperture 1630 towards the first fracture 21.

FIG. 131 is a partial perspective view of the exemplary rib cage 20 illustrating a step in a method of deploying a fracture repair system 1600 according to an embodiment of the present disclosure.

Step 4 may include pressurizing the balloon 1610 with air, other gas, and/or saline through the application instrument 1620 into the intramedullary canal towards the first fracture 21. Verifying that the balloon 1610 has bridged the fracture and entered the opposite portion of the bone using fluoroscopy.

FIG. 132 is a partial perspective view of the exemplary rib cage 20 illustrating a step in a method of deploying a fracture repair system 1600 according to an embodiment of the present disclosure.

Step 5 may include pressurizing the balloon 1610 with bone cement 1650 introduced through the application instrument 1620.

FIG. 133 is a partial perspective view of the exemplary rib cage 20 illustrating a step in a method of deploying a fracture repair system 1600 according to an embodiment of the present disclosure.

Step 6 may include continuing to expand the balloon 1610 until the balloon 1610 if fully expanded and spans the first fracture 21, and using fluoroscopy to verify the position of the balloon 1610 in relation to the first fracture 21.

FIG. 134 is a partial perspective view of the exemplary rib cage 20 illustrating a step in a method of deploying a fracture repair system 1600 according to an embodiment of the present disclosure. The balloon 1610 is shown fully expanded within the intramedullary canal and spanning the fracture.

Step 7 may include removing the application instrument 1620 and allowing the bone cement 1650 to harden.

FIG. 135 is a partial perspective section view of the exemplary rib cage 20 illustrating a step in a method of deploying a fracture repair system 1600 according to an embodiment of the present disclosure. The section view of the balloon 1610 shows the bone cement 1650 spanning the first fracture 21.

FIG. 136 is a partial perspective view of the exemplary rib cage 20 illustrating a step in a method of deploying a fracture repair system 1600 according to an embodiment of the present disclosure. The final construct is shown with the balloon 1610 within the intramedullary canal of a portion of bone and spanning the first fracture 21.

A method for stabilizing one or more fractures of a bone may include using a single tether to advance a plate to an interior surface of a bone, using a single tether to advance a first fastener and/or a second fastener to the interior surface of the bone, and/or using a single tether to compress or reduce one or more fractures of a bone. Additionally, or alternatively, the method may include using a second tether to advance a third fastener and/or a fourth fastener to the interior surface of the bone.

A method for stabilizing one or more fractures of a bone may also include introducing a fracture plating system through a VATS portal. A method for stabilizing one or more fractures of a bone may also include introducing a fracture plating system, with a first fastener captive in a first slot of the plate and/or a second fastener captive in a second slot of the plate, through a VATS portal.

A method for stabilizing one or more fractures of a bone may also include receiving fasteners through the bone on opposite sides of each of the one or more fractures. Additionally, or alternatively, the method may include receiving two or more fasteners in a slot of the plate.

A method for stabilizing one or more fractures of a portion of bone may include the following steps:

FIG. 84 is a perspective view of an exemplary rib cage 20 with an exemplary bone first fracture 21. FIG. 85 is a partial perspective view of the exemplary rib cage 20.

Step 1 may include identifying one or more fractures of a bone.

FIG. 86 is a partial perspective view of the exemplary rib cage 20 illustrating a step in a method of deploying a fracture plating system according to an embodiment of the present disclosure.

Step 2 may include drilling a first hole 15 and a second hole 16 wherein the first hole 15 and the second hole 16 are separated by a first fracture 21.

FIG. 87 is a partial perspective view of the exemplary rib cage 20 illustrating a step in a method of deploying a fracture plating system according to an embodiment of the present disclosure. FIG. 88 is a partial perspective view of the exemplary rib cage 20 illustrating a step in a method of deploying a fracture plating system according to an embodiment of the present disclosure.

Step 3 may include inserting a first end 72 of a first flexible guide tube 70 through the first hole 15. Inserting a first end 72 of a second flexible guide tube 70 through the second hole 16. Pulling the first end 72 of the first flexible guide tube 70 and the first end of the second flexible guide tube out 70 through a VATS portal using an endoscopic grasper or similar instrument. Ensuring that a second end 74 of the first flexible guide tube 70 does not pass through the first hole 15 and ensuring that a second end 74 of the second flexible guide tube 70 does not pass through the second hole 16. The flexible guide tube 70 may be fabricated of silicone rubber or other biocompatible elastomeric material.

FIG. 89A is a front view of a set of differently sized plates 102 according to an embodiment of the present disclosure. The fracture plating system 100 may be configured as a kit including a plurality of plates each having a different size and/or configuration, for example different plate length, different plate radius, different plate width, different number of slots, and/or different configuration of slots. The fracture plating system 100 may include a first plate **102*a* having a first plate length 103*a*, and a second plate 102*b* having a second plate length 103*b*, different from the first plate length 103*a***.

FIG. 89B is a front view of a set of differently sized fasteners 180 according to an embodiment of the present disclosure. The fracture plating system kit described above may further include a plurality of fasteners 180 each having a different size and/or configuration, for example, different length, different diameter, different thread configuration, and/or different head configuration. The fracture plating system 100 may include a first fastener **180*a* having a first fastener length 181*a*, and a second fastener 180*b* having a second fastener length 181*b*, different than the first fastener length 181*a***.

FIG. 89C is a front view of a set of differently sized locking nuts 1170 according to an embodiment of the present disclosure. The fracture plating system kit described above may further include a plurality of locking nuts 1170 each having a different size and/or configuration, for example, different length, different diameter, different thread configuration, and/or different head configuration. The fracture plating system 100 may include a first locking nut **1170*a* having a first body length 1180*a*, and a second locking nut 1170*b* having a second body length 1180*b*, different than the first body length 1180*a*. The first locking nut 1170*a* and the second locking nut 1170*b* are interchangeably securable to the first fastener 180*a* and the second fastener 180*b***.

FIG. 89D is a partial perspective view of an exemplary rib cage 20 showing an exemplary bone first fracture 21.

Step 4 may include measuring the rib thickness and other features of the portion of rib near the first fracture 21. Selecting a plate from a range of available sizes based on patient anatomy and a location of the fracture. Selecting two or more fasteners from a range of available sizes based on patient anatomy and a location of the fracture.

FIG. 90 is a front view of a fracture plating system illustrating a step in a method of deploying the fracture plating system according to an embodiment of the present disclosure. FIG. 91 is a front view of the fracture plating system of FIG. 90 illustrating a step in a method of deploying the fracture plating system according to an embodiment of the present disclosure. FIG. 92 is a front view of the fracture plating system of FIG. 90 illustrating a step in a method of deploying the fracture plating system according to an embodiment of the present disclosure.

Step 5 may include assembling the selected fasteners to the selected plate.

FIG. 93 is a partial perspective view of the exemplary rib cage 20 illustrating a step in a method of deploying a fracture plating system according to an embodiment of the present disclosure.

Step 6 may include inserting a first tether end 62 through a first fastener and a second tether end 64 through a second fastener.

FIG. 94 is a partial perspective view of the exemplary rib cage 20 illustrating a step in a method of deploying a fracture plating system according to an embodiment of the present disclosure.

Step 7 may include inserting a first tether end 62 into a second end 74 of the first flexible guide tube 70 and inserting the second tether end 64 into a second end 74 of the second flexible guide tube 70.

FIG. 95 is a partial perspective view of the exemplary rib cage 20 illustrating a step in a method of deploying a fracture plating system according to an embodiment of the present disclosure.

Step 8 may include feeding the first tether end 62 and the second tether end 64 through the first flexible guide tube 70 and the second flexible guide tube 70, respectively until the first tether end 62 and the second tether end 64 protrude through the first end 72 of the first flexible guide tube 70 and the first end 72 of the second flexible guide tube 70.

FIG. 96 is a partial perspective view of the exemplary rib cage 20 illustrating a step in a method of deploying a fracture plating system according to an embodiment of the present disclosure.

Step 9 may include removing the first flexible guide tube 70 and the second flexible guide tube 70 from the surgical site by pulling the first end 72 of the first flexible guide tube 70 and the first end 72 of the second flexible guide tube 70.

FIG. 97 is a partial perspective view of the exemplary rib cage 20 illustrating a step in a method of deploying a fracture plating system according to an embodiment of the present disclosure.

Step 10 may include pull the first tether end 62 and the second tether end 64 until the first fastener protrudes through the first hole 15 and the second fastener protrudes through the second hole 16. Optionally, continuing to pull until the fracture is reduced.

FIG. 98 is a partial perspective view of the exemplary rib cage 20 illustrating a step in a method of deploying a fracture plating system according to an embodiment of the present disclosure.

Step 11 may include placing a first washer over the first tether end 62 and then over the tip portion of the first fastener and placing a second washer over the second tether end 64 and then over the tip portion of the second fastener.

FIG. 99 is a partial perspective view of the exemplary rib cage 20 illustrating a step in a method of deploying a fracture plating system according to an embodiment of the present disclosure. FIG. 100 is a partial perspective view of the exemplary rib cage 20 illustrating a step in a method of deploying a fracture plating system according to an embodiment of the present disclosure.

Step 12 may include placing a first locking nut 30 over the first tether end 62 and threading and tightening the first locking nut onto the threaded portion of the first fastener. Placing a second locking nut 30 over the second tether end 64 and threading and tightening the second locking nut onto the threaded portion of the second fastener.

FIG. 101 is a partial perspective view of the exemplary rib cage 20 illustrating a step in a method of deploying a fracture plating system according to an embodiment of the present disclosure.

Step 13 may include removing the single tether 60 by pulling it with an endoscopic grasper, or similar instrument, through the VATS portal.

A method for stabilizing one or more fractures of a bone may include using a tether to advance a first fastener and/or a second fastener to the interior surface of the bone. The method may further include introducing the first fastener and/or the second fastener through a VATS portal. The method may also include introducing the plate to an exterior surface of the bone. The method may include advancing the fasteners through a hole in the bone so that a head portion contacts the interior surface and a distal end extends from the exterior surface of the bone. The method may further include receiving the distal end within a slot of the plate, and, using the fastener, securing the plate to the exterior surface of the bone.

A method for stabilizing one or more fractures of a portion of bone may include the following steps:

Step 1 may include identifying one or more fractures of a bone.

Step 2 may include drilling a first hole 15 and a second hole 16 wherein the first hole 15 and the second hole 16 are separated by a first fracture 21. The step may further include drilling additional holes through the bone on opposite sides of additional fractures, so that each fracture is between two holes in the bone.

Step 3 may include inserting a first end 72 of a first flexible guide tube 70 through the first hole 15. Inserting a first end 72 of a second flexible guide tube 70 through the second hole 16. Pulling the first end 72 of the first flexible guide tube 70 and the first end of the second flexible guide tube out 70 through a VATS portal using an endoscopic grasper or similar instrument. Ensuring that a second end 74 of the first flexible guide tube 70 does not pass through the first hole 15 and ensuring that a second end 74 of the second flexible guide tube 70 does not pass through the second hole 16. The flexible guide tube 70 may be fabricated of silicone rubber or other biocompatible elastomeric material.

Step 4 may include measuring the rib thickness and other features of patient anatomy and a location of the fracture. Selecting two or more fasteners from a range of available sizes based on patient anatomy and a location of the fracture. Selecting a plate from a range of available sizes based on patient anatomy and location/quantity of one or more fractures.

Step 5 may include inserting a first tether end 62 through a first fastener and a second tether end 64 through a second fastener.

Step 6 may include inserting a first tether end 62 into a second end 74 of the first flexible guide tube 70 and inserting the second tether end 64 into a second end 74 of the second flexible guide tube 70.

Step 7 may include feeding the first tether end 62 and the second tether end 64 through the first flexible guide tube 70 and the second flexible guide tube 70, respectively until the first tether end 62 and the second tether end 64 protrude through the first end 72 of the first flexible guide tube 70 and the first end 72 of the second flexible guide tube 70.

Step 8 may include removing the first flexible guide tube 70 and the second flexible guide tube 70 from the surgical site by pulling the first end 72 of the first flexible guide tube 70 and the first end 72 of the second flexible guide tube 70.

Step 9 may include pulling the first tether end 62 and the second tether end 64 until the first fastener is received in the first hole 15 and the second fastener is received in the second hole 16.

Step 10 may optionally include repeating Step 3 through Step 9 to introduce additional fasteners through additional holes in the bone.

Step 11 may include placing the plate on an exterior surface of the bone so that the plate spans the one or more fractures and the fasteners are received within one or more slots of the plate. The plate may be guided to the exterior surface by receiving the first tether end 62 and the second tether end 64 through one or more slots of the plate. The plate may be placed on the exterior surface of the bone through an open incision and/or through a transverse skin tunnel connecting two vertical soft tissue tunnels.

Step 12 may include securing the plate to the exterior surface of the bone by placing a first locking nut 30 over the first tether end 62 and threading and tightening the first locking nut onto the threaded portion of the first fastener and placing a second locking nut 30 over the second tether end 64 and threading and tightening the second locking nut onto the threaded portion of the second fastener. Optionally, additional locking nuts 30 may be used to engage additional fasteners.

Step 13 may include removing the single tether 60 by pulling it with an endoscopic grasper, or similar instrument, through the VATS portal and/or a trans-intercostal incision.

Those of skill in the art will recognize that this is only one of many potential methods that may be used to stabilize one or more fractures of a bone. In alternative embodiments, different methods may be used to implant the fracture plating system 100 or other fracture plating systems described above. Further, the method set forth in FIG. 84 though FIG. 101 may be used to implant other fracture plating systems besides those specifically disclosed herein.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

The invention claimed is:

1. A fracture plating system configured to stabilize a first fracture of a bone of a patient, the bone comprising an interior surface facing toward an interior body cavity of the patient, and an exterior surface facing away from the interior body cavity, the fracture plating system comprising:

a plate comprising one or more slots and configured to span the first fracture;

a first fastener configured to be received in one of the one or more slots and secure the plate to the interior surface of the bone;

a second fastener configured to be received in one of the one or more slots and secure the plate to the interior surface of the bone; and a single tether comprising a flexible material and configured to guide the plate, the first fastener, and the second fastener through the interior body cavity to the interior surface of the bone;

wherein with the single tether received in the first fastener and the second fastener, a tension on the single tether is uniform along its length during guidance of the plate, the first fastener, and the second fastener to the interior surface.

2. The fracture plating system of claim 1, wherein the single tether is further configured to facilitate reduction of the first fracture by, with the first fastener and the second fastener secured to the interior surface on opposite sides of the first fracture, urging the first fastener and the second fastener towards each other.

3. The fracture plating system of claim 1, wherein the single tether is further configured to guide the first fastener through a first hole in the bone and to guide the second fastener through a second hole in the bone, wherein the first hole and the second hole are on opposite sides of the first fracture.

4. The fracture plating system of claim 1, wherein:

the bone further comprises a second fracture; and the plate is further configured to stabilize the second fracture via attachment of the plate to the bone such that the plate spans the first fracture and the second fracture; and the fracture plating system further comprises:

a third fastener configured to be received in one of the one or more slots and secure the plate to the interior surface of the bone; and a fourth fastener configured to be received in one of the one or more slots and secure the plate to the interior surface of the bone.

5. The fracture plating system of claim 4, further comprises a second tether, wherein the second tether is configured to guide the third fastener to a first slot of the one or more slots and to guide the fourth fastener to a second slot of the one or more slots.

6. The fracture plating system of claim 1, further configured to stabilize three or more fractures of the bone, wherein the plate is further configured to span the three or more fractures and the single tether is configured to guide two fasteners to the interior surface of the bone and to one of the one or more slots.

7. The fracture plating system of claim 1, wherein:

the bone comprises a rib; and the single tether is further configured to draw the plate, the first fastener, and the second fastener through the interior body cavity to an interior surface of the rib.

8. A fracture plating system configured to stabilize a first fracture of a bone of a patient, the bone comprising an interior surface facing toward an interior body cavity of the patient, and an exterior surface facing away from the interior body cavity, the fracture plating system comprising:

a plate comprising one or more slots and configured to span the first fracture;

a first fastener configured to be received in one of the one or more slots and secure the plate to the interior surface of the bone;

a first nut comprising a first body length and configured to engage the first fastener;

a second fastener configured to be received in one of the one or more slots and secure the plate to the interior surface of the bone;

a second nut comprising a second body length and configured to engage the second fastener; and one or more tethers configured to apply a force to the first fastener and the second fastener to guide the plate, the first fastener, and the second fastener through the interior body cavity to the interior surface of the bone;

wherein:

the first nut and the second nut are selected from a set of nuts, each having a different body length to accommodate a different thickness of the bone;

the first body length is configured to extend into the bone a first depth;

the second body length is configured to extend into the bone a second depth different from the first depth; and with the first fastener and the second fastener captive within a first slot and a second slot, respectively, of the one or more slots, the first fastener is rotatable within the first slot and the second fastener is rotatable within the second slot.

9. The fracture plating system of claim 8, wherein the one or more tethers are further configured to facilitate reduction of the first fracture by, with the first fastener and the second fastener secured to the interior surface on opposite sides of the first fracture, urging the first fastener and the second fastener towards each other.

10. The fracture plating system of claim 8, wherein:

the bone comprises a rib; and the one or more tethers are further configured to draw the plate, the first fastener, and the second fastener through the interior body cavity to an interior surface of the rib.

11. The fracture plating system of claim 8, wherein:

the bone further comprises a second fracture; and the plate is further configured to stabilize the second fracture via attachment of the plate to the bone such that the plate spans the first fracture and the second fracture; and the fracture plating system further comprises:

a third fastener configured to be received in one of the one or more slots and secure the plate to the interior surface of the bone; and a fourth fastener configured to be received in one of the one or more slots and secure the plate to the interior surface of the bone.

12. The fracture plating system of claim 8, wherein the first fastener comprises a first cannulation configured to receive a first end of one of the one or more tethers, and the second fastener comprises a second cannulation configured to receive a second end of the one of the one or more tethers.

13. The fracture plating system of claim 8, further comprising a solid bead secured to one of the one or more tethers and configured to convey the force to one of the first fastener and the second fastener.

14. The fracture plating system of claim 8, wherein the one or more tethers comprises a single tether.

15. A fracture plating system configured to stabilize a first fracture of a bone of a patient, the bone comprising an interior surface facing toward an interior body cavity of the patient, and an exterior surface facing away from the interior body cavity, the fracture plating system comprising:

a plate assembly comprising:

a plate comprising one or more slots and configured to span the first fracture;

a first fastener configured to be coupled to one of the one or more slots and to secure the plate to the interior surface of the bone; and a second fastener configured to be coupled to one of the one or more slots and to secure the plate to the interior surface of the bone; and one or more tethers configured to apply a force directly to the first fastener and the second fastener to guide the plate assembly through the interior body cavity to the interior surface of the bone;

wherein the first fastener comprises a first head, a first threaded portion, and a first shank extending between the first head and the first threaded portion, with the first head and the first threaded portion enlarged relative to the first shank such that the first shank is captive in one of the one or more slots.

16. The fracture plating system of claim 15, wherein one of the one or more tethers are further configured to draw the first fastener through a first hole in a first portion of the bone proximate a first side of the first fracture; and draw the second fastener through a second hole in a second portion of the bone proximate a second side of the first fracture.

17. The fracture plating system of claim 15, wherein:

the bone further comprises a second fracture; and the plate is further configured to stabilize the second fracture via attachment of the plate to the bone such that the plate spans the first fracture and the second fracture; and the fracture plating system further comprises:

a third fastener configured to be received in one of the one or more slots and secure the plate to the interior surface of the bone; and a fourth fastener configured to be received in one of the one or more slots and secure the plate to the interior surface of the bone.

18. The fracture plating system of claim 15, wherein the one or more tethers are further configured to facilitate reduction of the first fracture by, with the first fastener and the second fastener secured to the interior surface on opposite sides of the first fracture, urging the first fastener and the second fastener towards each other.

19. The fracture plating system of claim 15, wherein:

the bone comprises a rib; and the one or more tethers are further configured to draw the plate assembly through the interior body cavity to an interior surface of the rib.

20. The fracture plating system of claim 15, wherein the first fastener comprises a first cannulation configured to receive a first end of one of the one or more tethers, and the second fastener comprises a second cannulation configured to receive a second end of the one of the one or more tethers.

21. The fracture plating system of claim 15, further comprising a first nut configured to receive the first fastener and to cooperate with the first fastener to secure the plate to the interior surface of the bone, and a second nut configured to receive the second fastener and to cooperate with the second fastener to secure the plate to the interior surface of the bone.

22. The fracture plating system of claim 15, wherein the one or more tethers comprises a single tether.

23. A fracture plating system configured to stabilize a first fracture of a bone of a patient, the bone comprising an interior surface facing toward an interior body cavity of the patient, and an exterior surface facing away from the interior body cavity, the fracture plating system comprising:

a plate comprising one or more slots and configured to span the first fracture;

a first fastener comprising a first threaded portion and configured to be received in one of the one or more slots and to secure the plate to the interior surface of the bone;

a first nut configured to engage the first fastener;

a second fastener comprising a second threaded portion and configured to be received in one of the one or more slots and to secure the plate to the interior surface of the bone;

a second nut configured to engage the second fastener; and one or more tethers configured to apply a force to the first fastener and the second fastener to guide the plate, the first fastener, and the second fastener through the interior body cavity to the interior surface of the bone;

wherein:

with the first nut engaged with the first fastener, the first threaded portion does not extend beyond the first nut;

with the second nut engaged with the second fastener, the second threaded portion does not extend beyond the second nut;

the first fastener, the second fastener, and at least one of the one or more tethers are configured to be provided in a pre-assembled state in which:

the first fastener and the second fastener are each captively retained within a respective one of the one or more slots through contact between a head of each fastener and the plate; and the at least one tether extends through a first cannulation of the first fastener and through a second cannulation of the second fastener such that the plate, the first fastener, the second fastener, and the at least one tether are guidable to the interior surface as a single integrated unit.

24. The fracture plating system of claim 23, wherein the one or more tethers are further configured to facilitate reduction of the first fracture by, with the first fastener and the second fastener secured to the interior surface on opposite sides of the first fracture, urging the first fastener and the second fastener towards each other.

25. The fracture plating system of claim 23, further comprising a solid bead secured to one of the one or more tethers and configured to convey the force to one of the first fastener and the second fastener.

26. The fracture plating system of claim 23, wherein the one or more tethers comprises a single tether.

* * * * *